United States Patent
Lahusen et al.

(10) Patent No.: US 11,242,527 B1
(45) Date of Patent: *Feb. 8, 2022

(54) COMBINATION VECTORS AND METHODS FOR TREATING CANCER

(71) Applicant: AMERICAN GENE TECHNOLOGIES INTERNATIONAL INC., Rockville, MD (US)

(72) Inventors: Tyler Lahusen, Rockville, MD (US); Mei-Ling Liou, Rockville, MD (US); Lingzhi Xiao, Rockville, MD (US); Haishan Li, Rockville, MD (US); Charles David Pauza, Rockville, MD (US)

(73) Assignee: American Gene Technologies International Inc., Rockville, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/198,017

(22) Filed: Mar. 10, 2021

Related U.S. Application Data

(63) Continuation of application No. 16/943,800, filed on Jul. 30, 2020, now Pat. No. 10,975,374, which is a continuation of application No. 16/083,384, filed as application No. PCT/US2017/021639 on Mar. 9, 2017, now Pat. No. 10,767,183.

(60) Provisional application No. 62/305,944, filed on Mar. 9, 2016.

(51) Int. Cl.
| | |
|---|---|
| *C12N 15/113* | (2010.01) |
| *C12N 15/86* | (2006.01) |
| *A61P 35/00* | (2006.01) |
| *C12N 15/62* | (2006.01) |
| *C12N 15/85* | (2006.01) |

(52) U.S. Cl.
CPC ......... *C12N 15/1135* (2013.01); *A61P 35/00* (2018.01); *C12N 15/1137* (2013.01); *C12N 15/1138* (2013.01); *C12N 15/62* (2013.01); *C12N 15/85* (2013.01); *C12N 15/86* (2013.01); *C12Y 205/01001* (2013.01); *C12Y 205/0101* (2013.01); *C12N 2320/31* (2013.01); *C12N 2830/48* (2013.01)

(58) Field of Classification Search
None
See application file for complete search history.

(56) References Cited

U.S. PATENT DOCUMENTS

| | | | |
|---|---|---|---|
| 8,124,752 B2 | 2/2012 | Bumcrot et al. | |
| 8,287,857 B2 | 10/2012 | Dudley et al. | |
| 9,834,790 B1 | 12/2017 | Pauza et al. | |
| 9,914,938 B2 | 3/2018 | Pauza et al. | |
| 10,023,880 B2 | 7/2018 | Pauza et al. | |
| 10,036,040 B2 | 7/2018 | Pauza et al. | |
| 10,137,144 B2 | 11/2018 | Pauza et al. | |
| 10,420,789 B2 | 9/2019 | Pauza et al. | |
| 10,472,649 B2 | 11/2019 | Pauza et al. | |
| 2004/0192629 A1 | 9/2004 | Xu et al. | |
| 2004/0248296 A1 | 12/2004 | Beresford et al. | |
| 2004/0265306 A1 | 12/2004 | Arthos et al. | |
| 2005/0019927 A1 | 1/2005 | Markus et al. | |
| 2006/0057553 A1 | 3/2006 | Aguilar-Cordova | |
| 2006/0073576 A1 | 4/2006 | Barnett et al. | |
| 2006/0246520 A1 | 11/2006 | Champagne et al. | |
| 2007/0141679 A1 | 6/2007 | Sodroski | |
| 2008/0003225 A1 | 1/2008 | Vie et al. | |
| 2008/0003682 A1 | 1/2008 | Lois-Caballe et al. | |
| 2008/0153737 A1 | 6/2008 | Lieberman et al. | |
| 2008/0199961 A1 | 8/2008 | Rasko et al. | |
| 2008/0227736 A1 | 9/2008 | Chen et al. | |
| 2008/0293142 A1 | 11/2008 | Liu et al. | |
| 2009/0148936 A1 | 6/2009 | Stout et al. | |
| 2009/0304688 A1 | 12/2009 | Fournie et al. | |
| 2010/0316676 A1 | 12/2010 | Sanders | |
| 2011/0008803 A1 | 1/2011 | Stockwell et al. | |
| 2012/0027725 A1 | 2/2012 | Galvin et al. | |
| 2013/0090371 A1 | 4/2013 | Lu et al. | |
| 2013/0122380 A1 | 8/2013 | Aquino et al. | |
| 2014/0155468 A1 | 6/2014 | Gregory et al. | |
| 2014/0178340 A1 | 6/2014 | Robbins et al. | |
| 2014/0348794 A1 | 11/2014 | Chiorini et al. | |
| 2015/0010578 A1 | 1/2015 | Balazs et al. | |

(Continued)

FOREIGN PATENT DOCUMENTS

| | | |
|---|---|---|
| CN | 101516365 | 8/2009 |
| CN | 101679466 | 3/2010 |

(Continued)

OTHER PUBLICATIONS

Oleg Tolmachov, Tanya Tolmachova and Faisal A. Al-Allaf (2011). Designing Lentiviral Gene Vectors, Viral Gene Therapy, Dr. Ke Xu (Ed.), ISBN: 978-953-307-539-6, InTech, Available from: http://www.intechopen.com/books/viral-gene-therapy/designing-lentiviral-gene-vectors.*

(Continued)

*Primary Examiner* — Sean McGarry
(74) *Attorney, Agent, or Firm* — DLA Piper LLP (US)

(57) ABSTRACT

A composition for treating cancer is disclosed. The composition includes a lentiviral particle and an aminobisphosphonate drug. The lentiviral particle is capable of infecting a target cell, such as a cancer cell, and includes an envelope protein optimized for targeting such target cell and a viral vector. The viral vector includes a small RNA optimized to target an FDPS mRNA sequence. The aminobisphosphonate drug includes zoledronic acid.

19 Claims, 11 Drawing Sheets

Specification includes a Sequence Listing.

(56) References Cited

U.S. PATENT DOCUMENTS

| | | |
|---|---|---|
| 2015/0018539 A1 | 1/2015 | Fellmann |
| 2015/0126580 A1 | 5/2015 | DePinho et al. |
| 2016/0060707 A1 | 3/2016 | Goldenberg et al. |
| 2016/0243169 A1 | 8/2016 | Chen et al. |
| 2017/0015976 A1 | 1/2017 | Nelson |
| 2017/0335344 A1 | 11/2017 | Pauza et al. |
| 2018/0142257 A1 | 5/2018 | Pauza |
| 2018/0142258 A1 | 5/2018 | Pauza |
| 2018/0195050 A1 | 7/2018 | Szalay |
| 2018/0256624 A1 | 9/2018 | Pauza |
| 2018/0305716 A1 | 10/2018 | Pauza et al. |
| 2018/0355032 A1 | 12/2018 | Roberts |
| 2019/0062786 A1 | 2/2019 | Pauza et al. |
| 2019/0078096 A1 | 3/2019 | Lahusen et al. |
| 2019/0083523 A1 | 3/2019 | Pauza |
| 2019/0218573 A1 | 7/2019 | Pauza et al. |
| 2019/0388456 A1 | 12/2019 | Pauza et al. |
| 2020/0063161 A1 | 2/2020 | Pauza |
| 2020/0181645 A1 | 6/2020 | Pauza |
| 2021/0047644 A1 | 2/2021 | Lahusen |

FOREIGN PATENT DOCUMENTS

| | | |
|---|---|---|
| CN | 101805750 | 8/2010 |
| CN | 105112370 | 12/2015 |
| CN | 108883100 | 11/2018 |
| EP | 3402483 | 11/2018 |
| EP | 3426777 | 1/2019 |
| JP | 2007-527240 | 9/2007 |
| JP | 2008-538174 | 10/2008 |
| JP | 2013-530152 | 7/2013 |
| JP | 2015-518838 | 7/2015 |
| JP | 2016-502404 | 1/2016 |
| WO | 2002020554 | 3/2002 |
| WO | 2005033282 | 4/2005 |
| WO | 2006039721 | 4/2006 |
| WO | 2007000668 | 1/2007 |
| WO | 2007015122 | 2/2007 |
| WO | 2007132292 | 11/2007 |
| WO | 2008025025 | 2/2008 |
| WO | 2009100928 | 8/2009 |
| WO | 2009147445 | 12/2009 |
| WO | 2010051521 | 5/2010 |
| WO | 2010117974 | 10/2010 |
| WO | 2010127166 | 11/2010 |
| WO | 2011008348 | 1/2011 |
| WO | 2012048303 | 4/2012 |
| WO | 2012061075 | 5/2012 |
| WO | 2012145624 | 10/2012 |
| WO | 2013096455 | 6/2013 |
| WO | 2014117050 | 7/2014 |
| WO | 2014187881 | 11/2014 |
| WO | 2015017755 | 2/2015 |
| WO | 2015078999 | 6/2015 |
| WO | 2015164759 | 10/2015 |
| WO | 20170068077 | 4/2017 |
| WO | 2017123918 | 7/2017 |
| WO | 2017156311 | 9/2017 |
| WO | 20170173453 | 10/2017 |
| WO | 2018009246 | 1/2018 |
| WO | 20180148443 | 8/2018 |
| WO | 2018232359 | 12/2018 |
| WO | 2020011247 | 1/2020 |
| WO | 2020097049 | 5/2020 |
| WO | 2021178571 | 9/2021 |

OTHER PUBLICATIONS

Li et al., "Reduced Expression of the Mevalonate Pathway Enzyme Farnesyl Pyrophosphate Synthase Unveils Recognition of Tumor Cells by Vγ2Vδ2 T Cells," J. of Immunology, 2009, vol. 182, pp. 8118-8124.

Wang et al., "Indirect Stimulation of Human Vγ2Vδ2 T Cells through Alterations in Isoprenoid Metabolism," J. of Immunology, vol. 187 pp. 5099-5113, (Nov. 15, 2011).

Dieli et al., "Targeting Human γδ T Cells with Zoledronate and Interleukin-2 for lmmunotherapy of Hormone-Refractory Prostate Cancer," Europe PMC Funders Group, Cancer Research, vol. 67(15), pp. 7450-1451, (Aug. 1, 2007).

Jiang et al., "A Novel EST-Derived RNAi Screen Reveals a Critical Role for Farnesyl Diphosphate Synthase in Beta2-Adrenergic Receptor Internalization and Down-Regulation," FASEB Journal, vol. 26(5), pp. 1-13, (Jan. 25, 2012).

Miettinen et al., "Mevalonate Pathway Regulates Cell Size Homeostasis and Proteostasis Through Autophagy," Cell Reports, vol. 13(11), pp. 2610-2620, (Dec. 2015).

Tolmachov, "Designing Lentiviral Gene Vectors," Viral Gene Therapy, Chapter 13, pp. 263-284, (2011).

Tracey, "Human DNA Sequence from Clone RP1-288M22 on Chromosome 6q 12-13," Complete Sequence, National Center for Biotechnology. GenBank Entry. Retrieved from the internet: <https://www.ncbi.nlm.nih.gov/nucleotide/AL035467.23?report=genbank&log$=nucltop&blast_rank=1&RID=UUD4GX2D014>; pp. 1-34, (Jan. 24, 2013).

Z. Li, "Inhibition of farnesyl pyrophosphate synthase prevents angiotensin II-induced cardiac fibrosis in vitro," Clinical & Experimental Immunology, (2014).

Xiaofeng Jiang, "A novel EST-derived RNAi screen reveals a critical role for farnesyl diphophate in B2-adrenerigic receptor internalization and down-regulation," The FASEB Journal, vol. 26, pp. 1-13(1995).

Jian Yang, "Lentiviral-Mediated Silencing of Farnelsyl Pyrophosphate Synthase through RNA Interference in Mice," Biomed Research International, vol. 2015, Article ID 914026, 6 pages, (2015).

Yang Ye, "Knockdown of farnesyl pyrophosphate synthase prevents angiotensin II-medicated cardiac hypertrophy," The International Journal of Biochemistry & Cell Biology, vol. 42, pp. 2056-2064, (2010).

Jianqiang Li, "Reduced Expression of Mevalonate Pathway Enzyme Farnesyl Pyrophosphate Synthase Unveils Recognition of Tumor Cells by V9V2 Cells," The Journal of Immunology, pp. 8118-8124, (2019).

Nada et al, "Enhancing adoptive cancer immunotherapy with Vγ2Vδ2 T cells through pulse zoledronate stimulation", Journal for Immunotherapy of Cancer, vol. 5, No. 1, (Feb. 21, 2017), pp. 1-23, (2017) DOI 10.1186/s40425-017-0209-6 *the whole document*.

Benyamine et al., "BTN3A molecules considerably improve Vγ9Vδ2T cells-based immunotherapy in acute myeloid leukemia," Oncolmmunology, vol. 5, No. 10, 10 pages, (Oct. 2, 2016), E1146843 *the whole document*.

Harly et al., "Key implication of CD277/butyrophilin-3 (BTN3A) in cellular stress sensing by a major human γδ T-cell subset," American Society of Hematology , vol. 120, No. 11, (Sep. 13, 2012), pp. 2269-2279, XP055081172, ISSN: 0006-4971, DOI: 10.1182/blood-2012-05-430470 *the whole document*.

Wang et al., "Intravenous Delivery of SiRNA Targeting CD47 Effectively Inhibits Melanoma Tumor Growth and Lung Metastasis", Molecular Therapy, pp. 1919-1929, vol. 21, No. 10, Oct. 2013.

Ostertag et al., "Brain Tumor Eradication and Prolonged Survival from Intratumoral Conversion of 5-Fluorocytosine to 5-fluorouracil Using a Nonlytic Retroviral Replicating Vector," Neoro-Oncology 14(2), pp. 145-159, Feb. 2012.

Twitty et al., "Retroviral Replicating Vectors Deliver Cytosine Deaminase Leading to Targeted 5-Fluorouracil-Mediated Cytotoxicity in Multiple Human Cancer Types, Human Gene Therapy Methods", 27(1), pp. 17-31, Feb. 1, 2016.

Hassan et al., "Isolation of umbilical cord mesenchymal stem cells using human blood derivative accompanied with explant method," Stem Cell Investigation, pp. 1-8, (2019).

Huang et al., "An Efficient protocol to generate placental chorionic plate-derived mesenchymal stem cells with superior proliferative and immunomodulatory properties," Stem Cell Research & Therapy, pp. 1-15, (2019).

(56) References Cited

OTHER PUBLICATIONS

Thompson et al., "Alkylamines cause Vγ9Vδ2 T-cell activation and proliferation by inhibiting the mevalonate pathway," Blood, Jan. 15, 2006, vol. 107, pp. 651-654.
Gober et al., "Human T Cell Receptor γδ Cells Recognize Endogenous Mevalonate Metabolites in Tumor Cells," J. of Experimental Med., Jan. 20, 2003, vol. 197, pp. 163-168.
Human papillomavirus type 16 (HPV16), complete genome; GenBank: K02718.1; Publication [online], Mar. 18, 1994, https://www.ncbi.nlm.nih.gov/nucleotide/333031?report=genbank&log$=nucltop&blast_rank=22&RID=H3E1THFU014; pp. 1-4.
{Long control region} [human papillomavirus, type 16, Genomic, 860 nt]; Accession 560559. Publication [online]. May 7, 1993, https://www.ncbi.nlm.nih.gov/nucleotide/237343?report=genbank&log$=nucltop&blast_rank=1&RID=H3FCKA00014; pp. 1.
Stunkel et al., "The Chromatin Structure of the Long Control Region of Human Papillomavirus Type 16 Repress Viral Oncoprotein Expression," Journal of Virology, vol. 73, No. 3, pp. 1918-1930 (Mar. 1999).
Lu et al., "Anti-Sense-Mediated Inhibition of Human Immunodeficiency Virus (HIV) Replication by Use of an HIV Type 1-Based Vector Results in Severely Attenuated Mutants Incapable of Developing Resistance," Journal of Virology, vol. 79, No. 13, pp. 7079-7088 (Jul. 2004).
GenBank Accession No. JG619773, MNESC1NG-T3-001_L15_6FEB2009_054 MNESC1NG cell culture from Mahonia nervosa Berberis nervosa cDNA, mRNA sequence, Feb. 13, 2014 (online). [Retrieved on Dec. 5, 2017]. Retrieved from the internet:<URL: https://www.ncbi.nlm.nih.gov/nucest/JG619773 > entire document.
Moser et al., "yd T cells: novel initiators of adaptive immunity," Immunological Reviews, vol. 215, pp. 89-102 (Feb. 2, 2007).
Capietto, A. H. et al., "Stimulated yδ T Cells Increase the in Vivo Efficacy of Trastuzumab in Her-2+ Breast Cancer," J Immunology, vol. 187(2), pp. 1031-1038, (2011).
Chen, Z. and M. S. Freedman, "CD16+ yδ T Cells Mediate Antibody Dependent Cellular Cytotoxicity: Potential Mechanism in the Pathogenesis of Multiple Sclerosis," Clin Immunology, vol. 128(2), pp. 219-227, (2008).
Couzi, L. et al., "Antibody-Dependent Anti-Cytomegalovirus Activity of Human yδ T Cells Expressing CD16 (FcγRIIIa)," Blood, vol. 119(6), pp. 1418-1427, (2012).
Fisher, J. P. et al., "Effective Combination Treatment of GD2-Expressing Neuroblastoma and Ewing's Sarcoma Using Anti-GD2 ch14.18/CHO Antibody with Vγ9Vδ2+ yδT Cells," OncoImmunology, vol. 5(1), pp. e1025194, (2016).
Gertner-Dardenne, J. et al., "Bromohydrin pyrophosphate enhances antibody-dependent cell-mediated cytotoxicity induced by therapeutic antibodies," Blood 113(20): 4875-4884, (2009).
Poonia, B. and C. D. Pauza, "Gamma delta T cells from HIV+ donors can be expanded in vitro by zoledronate/interleukin-2 to become cytotoxic effectors for antibody-dependent cellular cytotoxicity," Cytotherapy 14(2): 173-181, (2012).
Schiller, C. B. et al., "CD19-Specific Triplebody SPM-1 Engages NK and yδ T Cells for Rapid and Efficient Lysis of Malignant B-Lymphoid Cells," Oncotarget, vol. 7(50), pp. 83392-83408, (2016).
Tokuyama, H. et al., "Vγ9Vδ2 T Cell Cytotoxicity Against Tumor Cells is Enhanced by Monoclonal Antibody Drugs—Rituximab and Trastuzumab," Int J Cancer, vol. 122(11), pp. 2526-2534, (2008).
Oh et al. "Lentiviral Vector Design Using Alternative RNA Export Elements," Retrovirology, vol. 4:38, pp. 1-10, (2007).
Ding et al., "Administration-Route and Gender-Independent Longterm Therapeutic Correction of Phenylketonuria (PKU) in a Mouse Model by Recombinant Adeno-Associated Virus 8 Pseudotyped Vector-Mediated Gene Transfer," Gene Therapy, vol. 13, pp. 583-587, (Dec. 1, 2005).
Nowacki et al., "The PAH Mutation Analysis Consortium Database: Update 1996," Nucleic Acid Research, vol. 25(1), pp. 139-142, (Jan. 1, 1997).
Condiotti et al., "Prolonged Liver-Specific Transgene Expression by a Non-Primate Lentiviral Vector," Biochemical and Biophysical Research Communications, vol. 320(3), pp. 998-1006, (Jul. 30, 2004).
Wang et al., "Butyrophilin 3A1 Plays an Essential Role in Prenyl Pyrophosphate Stimulation of Human Vg2Vd2 T Cells," Journal of Immunology, vol. 191(3), pp. 1029-1042, (Jul. 5, 2013).
Hee Yeon Kim., "Farnesyl diphosphate synthase is important for the maintenance of glioblastoma stemness," Experimental & Molecular Medicine, (2018).
Hong Wang., "Indirect Stimulation of Human V2V2 Cells Through Aleterations in Isoprenoid Metabolism," The Journal of Immunology, (2011).
Daryl S. Schiller, "Parameters Influencing Measurement of the Gag Antigen-Specific T-Proliferative Response to HIV Type 1 Infection," AIDS Research and Human Retroviruses, vol. 16, No. 3, pp. 259-271, (2000).
Selbach et al., "Widespread changes in protein synthesis induced by microRNAs," Nature, vol. 455, Sep. 4, 2008, pp. 58-63, doi:10.1038/nature07228.
Roden et al., "Novel determinants of mammalian primary microRNA processing revealed by systematic evkuation of hairpin-containing transcripts and human genetic variation," Cold Spring Harbor Laboratory Press, vol. 27, pp. 374-384, ISSN 1088-9051/17; www.genome.org.
PCT; International Search Report and Written Opinion in the PCT Application No. PCT/US2019/059828 dated Feb. 14, 2020.
PCT: International Search Report dated May 26, 2017 in Application No. PCT/US2017/013399.
PCT: Written Opinion dated May 26, 2017 in Application No. PCT/US2017/013399.
PCT: International Search report dated Aug. 25, 2017 in Application No. PCT/US2017/021639.
PCT: Written Opinion dated Aug. 25, 2017 Application No. PCT/US2017/021639.
PCT; International Search Report dated Nov. 9, 2018 in Application No. PCT/US2018/037924.
PCT; Written Opinion dated Nov. 9, 2018 in Application No. PCT/US2018/037924.
USPTO; Notice of Allowance dated Oct. 13, 2017 in U.S. Appl. No. 14/706,481.
USPTO; Notice of Allowance dated Nov. 2, 2017 in U.S. Appl. No. 15/652,080.
USPTO; Non-Final Office Action dated Feb. 22, 2018 in U.S. Appl. No. 15/850,937.
USPTO; Non-Final Office Action dated Feb. 22, 2018 in U.S. Appl. No. 15/849,062.
USPTO; Notice of Allowance dated Apr. 23, 2018 in U.S. Appl. No. 15/850,937.
USPTO; Notice Allowance dated Apr. 26, 2018 in U.S. Appl. No. 15/849,062.
USPTO; Non-Final Office Action dated Jun. 15, 2018 in U.S. Appl. No. 15/904,131.
USPTO; Non-Final Office Action dated Dec. 31, 2018 in U.S. Appl. No. 16/182,443.
USPTO; Final Office Action dated May 2, 2019 in U.S. Appl. No. 16/182,443.
USPTO; Non-Final Office Action dated May 7, 2019 in U.S. Appl. No. 16/008,991.
USPTO; Non-Final Office Action dated May 16, 2019 in U.S. Appl. No. 16/132,247.
USPTO; Notice of Allowance dated Jun. 18, 2019 in the U.S. Appl. No. 16/182,443.
USPTO; Notice of Allowance dated Jul. 3, 2019 in U.S. Appl. No. 16/182,443.
USPTO; Notice of Allowance dated Aug. 14, 2019 in the U.S. Appl. No. 16/008,991.
USPTO; Final Office Action dated Jul. 1, 2019 in the U.S. Appl. No. 16/132,247.
USPTO; Notice of Allowance dated Jul. 19, 2019 in the U.S. Appl. No. 16/132,247.
USPTO; Restriction Requirement dated Nov. 7, 2019 in the U.S. Appl. No. 16/083,384.

(56) References Cited

OTHER PUBLICATIONS

USPTO; Non-Final Office Action dated Mar. 16, 2020 in the U.S. Appl. No. 16/083,384.
USPTO; Notice of Allowance dated May 18, 2020 in the U.S. Appl. No. 16/083,384.
USPTO; Non-Final Office Action dated Jun. 1, 2020 in the U.S. Appl. No. 16/530,908.
USPTO; Notice of Allowance dated Jul. 10, 2020 in the U.S. Appl. No. 16/530,908.
USPTO; Non-Final Office Action dated Nov. 25, 2020 in the U.S. Appl. No. 16/943,800.
USPTO; Restriction Requirement dated Dec. 8, 2020 in the U.S. Appl. No. 16/563,738.
USPTO; Notice of Allowance dated Feb. 10, 2021 in the U.S. Appl. No. 16/943,800.
USPTO; Non-Final Office Action dated Mar. 12, 2021 in the U.S. Appl. No. 16/563,738.
USPTO; Invitation to Pay Additional Fees and, Where Applicable, Protest Fee dated Sep. 11, 2018 in Application No. PCT/US2018/37924.
JP; Japanese Office Action in the Application No. 2018-536892 dated Jun. 26, 2020.
JP; Final Office Action in the JP Application No. 2018-536892 dated Nov. 16, 2020.
CN; 1st Office Action in the CN Application No. 202010396594.8 dated Jan. 15, 2021.
EP; Supplementary Search Report in the EP Application No. 18817253 dated Feb. 10, 2021.
JP; Office Action in the JP Application No. 2018-547354 dated Feb. 16, 2021.
EPO; Extended Search Report dated Jun. 6, 2019 in EP Application No. 17739028.3.
CN; 1st Office Action in the CN Application No. 20170017712.6 dated May 8, 2020.
EPO; European Search Report dated Aug. 12, 2019 in the EP Application No. 17764128.9.
Davis-Gardner et al., "eCD4-Ig promotes ADCC activity of sera from HIV-1-infected patients", Department of Immunology and Microbiology, The Scripps Research Institute, PLOS Pathogen, Dec. 18, 2017, https://doi.org/10.1371/journal.ppat.1006786.
PCT; International Search Report and Written Opinion in the PCT Application No. PCT/US2021/020721 dated Jul. 21, 2021.

\* cited by examiner

```
                         SEQUENCE LISTING

<160> NUMBER OF SEQ ID NOS: 84

<210> SEQ ID NO 1
<211> LENGTH: 53
<212> TYPE: DNA
<213> ORGANISM: Artificial Sequence
<220> FEATURE:
<223> OTHER INFORMATION: FDPS shRNA sequence #1

<400> SEQUENCE: 1
gtcctggagt acaatgccat tctcgagaat ggcattgtac tccaggactt ttt            53

<210> SEQ ID NO 2
<211> LENGTH: 53
<212> TYPE: DNA
<213> ORGANISM: Artificial Sequence
<220> FEATURE:
<223> OTHER INFORMATION: FDPS shRNA sequence #2

<400> SEQUENCE: 2
gcaggatttc gttcagcact tctcgagaag tgctgaacga aatcctgctt ttt            53

<210> SEQ ID NO 3
<211> LENGTH: 53
<212> TYPE: DNA
<213> ORGANISM: Artificial Sequence
<220> FEATURE:
<223> OTHER INFORMATION: FDPS shRNA sequence #3

<400> SEQUENCE: 3
gccatgtaca tggcaggaat tctcgagaat tcctgccatg tacatggctt ttt            53

<210> SEQ ID NO 4
<211> LENGTH: 53
<212> TYPE: DNA
<213> ORGANISM: Artificial Sequence
<220> FEATURE:
<223> OTHER INFORMATION: FDPS shRNA sequence #4

<400> SEQUENCE: 4
gcagaaggag gctgagaaag tctcgagact ttctcagcct ccttctgctt ttt            53

<210> SEQ ID NO 5
<211> LENGTH: 49
<212> TYPE: DNA
<213> ORGANISM: Artificial Sequence
<220> FEATURE:
<223> OTHER INFORMATION: CD47 shRNA sequence #1

<400> SEQUENCE: 5
ggtgaaacga tcatcgagcc tcgaggctcg atgatcgttt cacctttt                  49

<210> SEQ ID NO 6
<211> LENGTH: 49
<212> TYPE: DNA
<213> ORGANISM: Artificial Sequence
<220> FEATURE:
<223> OTHER INFORMATION: CD47 shRNA sequence #2

<400> SEQUENCE: 6
gctactggcc ttggtttaac tcgagttaaa ccaaggccag tagctttt                  49
```

<210> SEQ ID NO 7
<211> LENGTH: 49
<212> TYPE: DNA
<213> ORGANISM: Artificial Sequence
<220> FEATURE:
<223> OTHER INFORMATION: CD47 shRNA sequence #3

<400> SEQUENCE: 7
cctccttcgt cattgccatc tcgagatggc aatgacgaag gaggttttt                49

<210> SEQ ID NO 8
<211> LENGTH: 49
<212> TYPE: DNA
<213> ORGANISM: Artificial Sequence
<220> FEATURE:
<223> OTHER INFORMATION: CD47 shRNA sequence #4

<400> SEQUENCE: 8
gcatggccct cttctgattc tcgagaatca gaagagggcc atgctttt                 49

<210> SEQ ID NO 9
<211> LENGTH: 53
<212> TYPE: DNA
<213> ORGANISM: Artificial Sequence
<220> FEATURE:
<223> OTHER INFORMATION: CD47 shRNA sequence #5

<400> SEQUENCE: 9
ggtgaaacga tcatcgagct actcgagtag ctcgatgatc gtttcacctt ttt           53

<210> SEQ ID NO 10
<211> LENGTH: 52
<212> TYPE: DNA
<213> ORGANISM: Artificial Sequence
<220> FEATURE:
<223> OTHER INFORMATION: cMyc shRNA sequence #1

<400> SEQUENCE: 10
gcttcaccaa caggaactat gctcgagcat agttcctgtt ggtgaagctt tt            52

<210> SEQ ID NO 11
<211> LENGTH: 52
<212> TYPE: DNA
<213> ORGANISM: Artificial Sequence
<220> FEATURE:
<223> OTHER INFORMATION: cMyc shRNA sequence #2

<400> SEQUENCE: 11
gcgaacacac aacgtcttgg actcgagtcc aagacgttgt gtgttcgctt tt            52

<210> SEQ ID NO 12
<211> LENGTH: 53
<212> TYPE: DNA
<213> ORGANISM: Artificial Sequence
<220> FEATURE:
<223> OTHER INFORMATION: cMyc shRNA sequence #3

<400> SEQUENCE: 12
gacatggtga accagagttt cctcgaggaa actctggttc accatgtctt ttt           53

<210> SEQ ID NO 13
<211> LENGTH: 53
<212> TYPE: DNA
<213> ORGANISM: Artificial Sequence
<220> FEATURE:
<223> OTHER INFORMATION: cMyc shRNA sequence #4

```
<400> SEQUENCE: 13
gagaatgtca agaggcgaac actcgagtgt tcgcctcttg acattctctt ttt         53

<210> SEQ ID NO 14
<211> LENGTH: 53
<212> TYPE: DNA
<213> ORGANISM: Artificial Sequence
<220> FEATURE:
<223> OTHER INFORMATION: cMyc shRNA sequence #5

<400> SEQUENCE: 14
gctcatttct gaagaggact tctcgagaag tcctcttcag aaatgagctt ttt         53

<210> SEQ ID NO 15
<211> LENGTH: 217
<212> TYPE: DNA
<213> ORGANISM: Artificial Sequence
<220> FEATURE:
<223> OTHER INFORMATION: H1 promoter

<400> SEQUENCE: 15
gaacgctgac gtcatcaacc cgctccaagg aatcgcgggc ccagtgtcac taggcgggaa    60
cacccagcgc gcgtgcgccc tggcaggaag atggctgtga gggacagggg agtggcgccc   120
tgcaatattt gcatgtcgct atgtgttctg ggaaatcacc ataaacgtga atgtctttg    180 gatttgggaa tcttataagt tctgtatgag accactt                            217

<210> SEQ ID NO 16
<211> LENGTH: 249
<212> TYPE: DNA
<213> ORGANISM: Artificial Sequence
<220> FEATURE:
<223> OTHER INFORMATION: U6 promoter

<400> SEQUENCE: 16
gagggcctat ttcccatgat tccttcatat ttgcatatac gatacaaggc tgttagagag    60
ataattggaa ttaatttgac tgtaaacaca agatattag tacaaaatac gtgacgtaga   120
aagtaataat ttcttgggta gtttgcagtt ttaaaattat gttttaaaat ggactatcat   180
atgcttaccg taacttgaaa gtatttcgat ttcttggctt tatatatctt gtggaaagga   240
cgaaacacc                                                            249

<210> SEQ ID NO 17
<211> LENGTH: 243
<212> TYPE: DNA
<213> ORGANISM: Artificial Sequence
<220> FEATURE:
<223> OTHER INFORMATION: 7SK promoter

<400> SEQUENCE: 17
ctgcagtatt tagcatgccc cacccatctg caaggcattc tggatagtgt caaaacagcc    60
ggaaatcaag tccgtttatc tcaaacttta gcattttggg aataaatgat atttgctatg   120
ctggttaaat tagatttag ttaaatttcc tgctgaagct ctagtacgat aagcaacttg    180
acctaagtgt aaagttgaga tttccttcag gtttatatag cttgtgcgcc gcctggctac   240
ctc                                                                  243

<210> SEQ ID NO 18
<211> LENGTH: 352
<212> TYPE: DNA
```

<213> ORGANISM: Artificial Sequence
<220> FEATURE:
<223> OTHER INFORMATION: CAG enhancer

<400> SEQUENCE: 18

```
tagttattaa tagtaatcaa ttacggggtc attagttcat agcccatata tggagttccg     60
cgttacataa cttacggtaa atggcccgcc tggctgaccg cccaacgacc cccgcccatt    120
gacgtcaata atgacgtatg ttcccatagt aacgccaata gggactttcc attgacgtca    180
atgggtggac tatttacggt aaactgccca cttggcagta catcaagtgt atcatatgcc    240
aagtacgccc cctattgacg tcaatgacgg taaatggccc gcctggcatt atgcccagta    300
catgacccta tgggacttc ctacttggca gtacatctac gtattagtca tc             352
```

<210> SEQ ID NO 19
<211> LENGTH: 290
<212> TYPE: DNA
<213> ORGANISM: Artificial Sequence
<220> FEATURE:
<223> OTHER INFORMATION: CAG promoter

<400> SEQUENCE: 19

```
gctattacca tgggtcgagg tgagccccac gttctgcttc actctcccca tctcccccc     60
ctccccaccc ccaattttgt atttatttat tttttaatta ttttgtgcag cgatgggggc    120
ggggggggg gggcgcgcg ccaggcgggg cggggcgggg cgaggggcgg ggcggggcga    180
ggcggagagg tgcggcggca gccaatcaga gcggcgcgct ccgaaagttt ccttttatgg    240
cgaggcggcg gcggcggcgg ccctataaaa agcgaagcgc gcggcgggcg               290
```

<210> SEQ ID NO 20
<211> LENGTH: 960
<212> TYPE: DNA
<213> ORGANISM: Artificial Sequence
<220> FEATURE:
<223> OTHER INFORMATION: chicken beta actin intron

<400> SEQUENCE: 20

```
ggagtcgctg cgttgccttc gccccgtgcc ccgctccgcg ccgcctcgcg ccgcccgccc     60
cggctctgac tgaccgcgtt actcccacag gtgagcgggc gggacggccc ttctcctccg    120
ggctgtaatt agcgcttggt ttaatgacgg ctcgtttctt ttctgtggct gcgtgaaagc    180
cttaaagggc tccgggaggg ccctttgtgc ggggggagc ggctcggggg gtgcgtgcgt    240
gtgtgtgtgc gtggggagcg ccgcgtgcgg ccgcgctgc ccggcggctg tgagcgctgc    300
gggcgcggcg cggggctttg tgcgctccgc gtgtgcgcga ggggagcgcg gccggggggcg    360
gtgccccgcg gtgcgggggg gctgcgaggg gaacaaaggc tgcgtgcggg gtgtgtgcgt    420
ggggggggtga gcaggggggtg tgggcgcggc ggtcgggctg taaccccccc ctgcacccc    480
ctccccgagt tgctgagcac ggcccggctt cgggtgcggg gctccgtgcg gggcgtggcg    540
cggggctcgc cgtgccgggc gggggggtggc ggcaggtggg ggtgccgggc ggggcggggc    600
cgcctcgggc cggggagggc tcggggagg ggcgcggcgg ccccggagcg ccggcggctg    660
tcgaggcgcg gcgagccgca gccattgcct tttatggtaa tcgtgcgaga gggcgcaggg    720
acttcctttg tcccaaatct ggcggagccg aaatctggga ggcgccgccg cacccctct    780
agcgggcgcg gcgaagcgg tgcgcgccg gcaggaagga aatgggcggg agggccttc    840
gtgcgtcgcc gcgccgccgt cccctttctcc atctccagcc tcgggctgc cgcagggga    900
cggctgcctt cggggggac ggggcagggc gggttcggc ttctggcgtg tgaccggcgg    960
```

<210> SEQ ID NO 21
<211> LENGTH: 1503
<212> TYPE: DNA
<213> ORGANISM: Artificial Sequence
<220> FEATURE:
<223> OTHER INFORMATION: HIV gag

<400> SEQUENCE: 21

```
atgggtgcga gagcgtcagt attaagcggg ggagaattag atcgatggga aaaaattcgg      60
ttaaggccag ggggaaagaa aaatataaa ttaaaacata tagtatgggc aagcagggag      120
ctagaacgat tcgcagttaa tcctggcctg ttagaaacat cagaaggctg tagacaaata      180
ctgggacagc tacaaccatc ccttcagaca ggatcagaag aacttagatc attatataat      240
acagtagcaa ccctctattg tgtgcatcaa aggatagaga taaaagacac caaggaagct      300
ttagacaaga tagaggaaga gcaaaacaaa agtaagaaaa agcacagca agcagcagct      360
gacacaggac acagcaatca ggtcagccaa aattacccta tagtgcagaa catccagggg      420
caaatggtac atcaggccat atcacctaga actttaaatg catgggtaaa agtagtagaa      480
gagaaggctt tcagcccaga agtgataccc atgttttcag cattatcaga aggagccacc      540
ccacaagatt taaacaccat gctaaacaca gtggggggac atcaagcagc catgcaaatg      600
ttaaaagaga ccatcaatga ggaagctgca gaatgggata gagtgcatcc agtgcatgca      660
gggcctattg caccaggcca gatgagagaa ccaaggggaa gtgacatagc aggaactact      720
agtacccttc aggaacaaat aggatggatg acacataatc cacctatccc agtaggagaa      780
atctataaaa gatggataat cctgggatta aataaaatag taagaatgta tagccctacc      840
agcattctgg acataagaca aggaccaaag gaacccttta gagactatgt agaccgattc      900
tataaaactc taagagccga gcaagcttca caagaggtaa aaaattggat gacagaaacc      960
ttgttggtcc aaaatgcgaa cccagattgt aagactattt taaaagcatt gggaccagga     1020
gcgacactag aagaaatgat gacagcatgt cagggagtgg ggggacccgg ccataaagca     1080
agagttttgg ctgaagcaat gagccaagta acaaatccag ctaccataat gatacagaaa     1140
ggcaatttta ggaaccaaag aaagactgtt aagtgtttca attgtggcaa agaagggcac     1200
atagccaaaa attgcagggc ccctaggaaa aagggctgtt ggaaatgtgg aaaggaagga     1260
caccaaatga aagattgtac tgagagacag gctaattttt tagggaagat ctggccttcc     1320
cacaagggaa ggccagggaa ttttcttcag agcagaccag agccaacagc cccaccagaa     1380
gagagcttca ggtttgggga agagacaaca actccctctc agaagcagga gccgatagac     1440
aaggaactgt atcctttagc ttccctcaga tcactctttg gcagcgaccc ctcgtcacaa     1500
taa                                                                  1503
```

<210> SEQ ID NO 22
<211> LENGTH: 1872
<212> TYPE: DNA
<213> ORGANISM: Artificial Sequence
<220> FEATURE:
<223> OTHER INFORMATION: HIV Pol

<400> SEQUENCE: 22

```
atgaatttgc caggaagatg gaaaccaaaa atgataggggg aattggaggg ttttatcaaa      60
gtaggacagt atgatcagat actcatagaa atctgcggac ataaagctat aggtacagta     120
ttagtaggac ctacacctgt caacataatt ggaagaaatc tgttgactca gattggctgc     180
```

-continued

```
actttaaatt ttcccattag tcctattgag actgtaccag taaaattaaa gccaggaatg      240
gatggcccaa aagttaaaca atggccattg acagaagaaa aaataaaagc attagtagaa      300
atttgtacag aaatggaaaa ggaaggaaaa atttcaaaaa ttgggcctga aaatccatac      360
aatactccag tatttgccat aaagaaaaaa gacagtacta aatggagaaa attagtagat      420
ttcagagaac ttaataagag aactcaagat ttctgggaag ttcaattagg aataccacat      480
cctgcagggt taaaacagaa aaaatcagta acagtactgg atgtgggcga tgcatatttt      540
tcagttccct tagataaaga cttcaggaag tatactgcat ttaccatacc tagtataaac      600
aatgagacac cagggattag atatcagtac aatgtgcttc cacagggatg aaaggatca      660 ccagcaatat tccagtgtag catgacaaaa atcttagagc cttttagaaa acaaaatcca      720
gacatagtca tctatcaata catggatgat ttgtatgtag gatctgactt agaaataggg      780
cagcatagaa caaaaataga ggaactgaga caacatctgt tgaggtgggg atttaccaca      840
ccagacaaaa aacatcagaa agaacctcca ttcctttgga tgggttatga actccatcct      900
gataaatgga cagtacagcc tatagtgctg ccagaaaagg acagctggac tgtcaatgac      960
atacagaaat tagtgggaaa attgaattgg gcaagtcaga tttatgcagg gattaaagta     1020
aggcaattat gtaaacttct taggggaacc aaagcactaa cagaagtagt accactaaca     1080
gaagaagcag agctagaact ggcagaaaac agggagattc taaaagaacc ggtacatgga     1140
gtgtattatg acccatcaaa agacttaata gcagaaatac agaagcaggg gcaaggccaa     1200
tggacatatc aaatttatca agagccattt aaaaatctga aaacaggaaa atatgcaaga     1260 atgaaggggtg cccacactaa tgatgtgaaa caattaacag aggcagtaca aaaaatagcc     1320
acagaaagca tagtaatatg gggaaagact cctaaattta aattaccat acaaaaggaa     1380 acatgggaag catggtggac agagtattgg caagccacct ggattcctga gtgggagttt     1440
gtcaataccc ctcccttagt gaagttatgg taccagttag agaaagaacc cataatagga     1500
gcagaaactt tctatgtaga tggggcagcc aatagggaaa ctaaattagg aaaagcagga     1560
tatgtaactg acagaggaag acaaaaagtt gtcccctaa cggacacaac aaatcagaag     1620
actgagttac aagcaattca tctagctttg caggattcgg gattagaagt aaacatagtg     1680
acagactcac aatatgcatt gggaatcatt caagcacaac cagataagag tgaatcagag     1740
ttagtcagtc aaataataga gcagttaata aaaaaggaaa aagtctacct ggcatgggta     1800
ccagcacaca aaggaattgg aggaaatgaa caagtagatg ggttggtcag tgctggaatc     1860
aggaaagtac ta                                                         1872
```

<210> SEQ ID NO 23
<211> LENGTH: 867
<212> TYPE: DNA
<213> ORGANISM: Artificial Sequence
<220> FEATURE:
<223> OTHER INFORMATION: HIV Int

<400> SEQUENCE: 23

```
ttttagatg aatagataa ggcccaagaa gaacatgaga aatatcacag taattggaga       60
gcaatggcta gtgattttaa cctaccacct gtagtagcaa aagaaatagt agccagctgt     120
gataaatgtc agctaaaagg ggaagccatg catggacaag tagactgtag cccaggaata     180
tggcagctag attgtacaca tttagaagga aaagttatct tggtagcagt tcatgtagcc     240
agtggatata tagaagcaga agtaattcca gcagagacag ggcaagaaac agcatacttc     300
ctcttaaaat tagcaggaag atggccagta aaaacagtac atacagacaa tggcagcaat     360
```

| | |
|---|---:|
| ttcaccagta ctacagttaa ggccgcctgt tggtgggcgg ggatcaagca ggaatttggc | 420 |
| attccctaca atccccaaag tcaaggagta atagaatcta tgaataaaga attaaagaaa | 480 |
| attataggac aggtaagaga tcaggctgaa catcttaaga cagcagtaca aatggcagta | 540 |
| ttcatccaca attttaaaag aaaggggggg attgggggggt acagtgcagg ggaagaata | 600 |
| gtagacataa tagcaacaga catacaaact aaagaattac aaaaacaaat tacaaaaatt | 660 |
| caaaattttc gggtttatta cagggacagc agagatccag tttggaaagg accagcaaag | 720 |
| ctcctctgga aaggtgaagg ggcagtagta atacaagata atagtgacat aaaagtagtg | 780 |
| ccaagaagaa aagcaaagat catcaggat tatgggaaaac agatggcagg tgatgattgt | 840 |
| gtggcaagta gacaggatga ggattaa | 867 |

<210> SEQ ID NO 24
<211> LENGTH: 234
<212> TYPE: DNA
<213> ORGANISM: Artificial Sequence
<220> FEATURE:
<223> OTHER INFORMATION: HIV RRE

<400> SEQUENCE: 24

| | |
|---|---:|
| aggagctttg ttccttgggt tcttgggagc agcaggaagc actatgggcg cagcgtcaat | 60 |
| gacgctgacg gtacaggcca gacaattatt gtctggtata gtgcagcagc agaacaattt | 120 |
| gctgagggct attgaggcgc aacagcatct gttgcaactc acagtctggg gcatcaagca | 180 |
| gctccaggca agaatcctgg ctgtggaaag atacctaaag gatcaacagc tcct | 234 |

<210> SEQ ID NO 25
<211> LENGTH: 351
<212> TYPE: DNA
<213> ORGANISM: Artificial Sequence
<220> FEATURE:
<223> OTHER INFORMATION: HIV Rev

<400> SEQUENCE: 25

| | |
|---|---:|
| atggcaggaa gaagcggaga cagcgacgaa gaactcctca aggcagtcag actcatcaag | 60 |
| tttctctatc aaagcaaccc acctcccaat cccgagggga cccgacaggc ccgaaggaat | 120 |
| agaagaagaa ggtggagaga gagacagaga cagatccatt cgattagtga acggatcctt | 180 |
| agcacttatc tgggacgatc tgcggagcct gtgcctcttc agctaccacc gcttgagaga | 240 |
| cttactcttg attgtaacga ggattgtgga acttctggga cgcagggggt gggaagccct | 300 |
| caaatattgg tggaatctcc tacaatattg gagtcaggag ctaaagaata g | 351 |

<210> SEQ ID NO 26
<211> LENGTH: 448
<212> TYPE: DNA
<213> ORGANISM: Artificial Sequence
<220> FEATURE:
<223> OTHER INFORMATION: rabbit beta globin poly A

<400> SEQUENCE: 26

| | |
|---|---:|
| agatctttt ccctctgcca aaaattatgg ggacatcatg aagccccttg agcatctgac | 60 |
| ttctggctaa taaaggaaat ttattttcat tgcaatagtg tgttggaatt ttttgtgtct | 120 |
| ctcactcgga aggacatatg ggagggcaaa tcatttaaaa catcagaatg agtatttggt | 180 |
| ttagagtttg gcaacatatg ccatatgctg gctgccatga acaaaggtgg ctataaagag | 240 |
| gtcatcagta tatgaaacag ccccctgctg tccattcctt attccataga aaagccttga | 300 |

```
cttgaggtta gattttttt atattttgtt ttgtgttatt ttttctttta acatccctaa      360
aattttcctt acatgtttta ctagccagat ttttcctcct ctcctgacta ctcccagtca     420
tagctgtccc tcttctctta tgaagatc                                         448

<210> SEQ ID NO 27
<211> LENGTH: 577
<212> TYPE: DNA
<213> ORGANISM: Artificial Sequence
<220> FEATURE:
<223> OTHER INFORMATION: CMV Promoter

<400> SEQUENCE: 27
acattgatta ttgactagtt attaatagta atcaattacg gggtcattag ttcatagccc      60
atatatggag ttccgcgtta cataacttac ggtaaatggc ccgcctggct gaccgcccaa     120
cgacccccgc ccattgacgt caataatgac gtatgttccc atagtaacgc caatagggac    180
tttccattga cgtcaatggg tggagtattt acggtaaact gcccacttgg cagtacatca    240
agtgtatcat atgccaagta cgccccctat tgacgtcaat gacggtaaat ggcccgcctg    300
gcattatgcc cagtacatga ccttatggga ctttcctact tggcagtaca tctacgtatt    360
agtcatcgct attaccatgg tgatgcggtt ttggcagtac atcaatgggc gtggatagcg    420
gtttgactca cggggatttc caagtctcca ccccattgac gtcaatggga gtttgttttg    480
gcaccaaaat caacgggact ttccaaaatg tcgtaacaac tccgccccat tgacgcaaat    540
gggcggtagg cgtgtacggt gggaggtcta tataagc                              577

<210> SEQ ID NO 28
<211> LENGTH: 573
<212> TYPE: DNA
<213> ORGANISM: Artificial Sequence
<220> FEATURE:
<223> OTHER INFORMATION: beta globin intron

<400> SEQUENCE: 28
gtgagtttgg ggacccttga ttgttctttc ttttcgcta ttgtaaaatt catgttatat       60 ggaggggca agttttcag ggtgttgttt agaatgggaa gatgtccctt gtatcaccat       120
ggaccctcat gataattttg tttctttcac tttctactct gttgacaacc attgtctcct    180
cttattttct tttcatttc tgtaactttt tcgttaaact ttagcttgca tttgtaacga     240
atttttaaat tcactttgt ttatttgtca gattgtaagt actttctcta atcacttttt    300
tttcaaggca atcagggtat attatattgt acttcagcac agttttagag acaattgtt    360 ataattaaat gataaggtag aatatttctg catataaatt ctggctggcg tggaaatatt    420
cttattggta gaacaacta caccctggtc atcatcctgc ctttctcttt atggttacaa     480
tgatatacac tgtttgagat gaggataaaa tactctgagt ccaaaccggg cccctctgct    540
aaccatgttc atgccttctt ctctttccta cag                                 573

<210> SEQ ID NO 29
<211> LENGTH: 1531
<212> TYPE: DNA
<213> ORGANISM: Artificial Sequence
<220> FEATURE:
<223> OTHER INFORMATION: VSV-G / DNA fragment containing VSV-G

<400> SEQUENCE: 29
gaattcatga agtgcctttt gtacttagcc tttttattca ttggggtgaa ttgcaagttc      60
accatagttt ttccacacaa ccaaaaagga aactggaaaa atgttccttc taattaccat    120
```

```
tattgcccgt caagctcaga tttaaattgg cataatgact taataggcac agccttacaa    180
gtcaaaatgc ccaagagtca caaggctatt caagcagacg gttggatgtg tcatgcttcc    240
aaatgggtca ctacttgtga tttccgctgg tatggaccga agtatataac acattccatc    300
cgatccttca ctccatctgt agaacaatgc aaggaaagca ttgaacaaac gaaacaagga    360
acttggctga atccaggctt ccctcctcaa agttgtggat atgcaactgt gacggatgcc    420
gaagcagtga ttgtccaggt gactcctcac catgtgctgg ttgatgaata cacaggagaa    480
tgggttgatt cacagttcat caacggaaaa tgcagcaatt acatatgccc cactgtccat    540
aactctacaa cctggcattc tgactataag gtcaaagggc tatgtgattc taacctcatt    600
tccatggaca tcaccttctt ctcagaggac ggagagctat catccctggg aaaggagggc    660
acagggttca gaagtaacta ctttgcttat gaaactggag gcaaggcctg caaaatgcaa    720
tactgcaagc attggggagt cagactccca tcaggtgtct ggttcgagat ggctgataag    780
gatctctttg ctgcagccag attccctgaa tgcccagaag ggtcaagtat ctctgctcca    840
tctcagacct cagtggatgt aagtctaatt caggacgttg agaggatctt ggattattcc    900
ctctgccaag aaacctggag caaaatcaga gcgggtcttc caatctctcc agtggatctc    960
agctatcttg ctcctaaaaa cccaggaacc ggtcctgctt tcaccataat caatggtacc   1020
ctaaaatact ttgagaccag atacatcaga gtcgatattg ctgctccaat cctctcaaga   1080
atggtcggaa tgatcagtgg aactaccaca gaaagggaac tgtgggatga ctgggcacca   1140
tatgaagacg tggaaattgg acccaatgga gttctgagga ccagttcagg atataagttt   1200
cctttataca tgattggaca tggtatgttg gactccgatc ttcatcttag ctcaaaggct   1260
caggtgttcg aacatcctca cattcaagac gctgcttcgc aacttcctga tgatgagagt   1320
ttattttttg gtgatactgg gctatccaaa aatccaatcg agcttgtaga aggttggttc   1380
agtagttgga aaagctctat tgcctctttt ttctttatca tagggttaat cattggacta   1440
ttcttggttc tccgagttgg tatccatctt tgcattaaat taaagcacac caagaaaaga   1500
cagatttata cagacataga gatgagaatt c                                  1531
```

<210> SEQ ID NO 30
<211> LENGTH: 450
<212> TYPE: DNA
<213> ORGANISM: Artificial Sequence
<220> FEATURE:
<223> OTHER INFORMATION: rabbit beta globin poly A

<400> SEQUENCE: 30

```
agatcttttt ccctctgcca aaaattatgg ggacatcatg aagccccttg agcatctgac     60
ttctggctaa taaggaaat ttattttcat tgcaatagtg tgttggaatt ttttgtgtct    120
ctcactcgga aggacatatg ggagggcaaa tcatttaaaa catcagaatg agtatttggt    180
ttagagtttg gcaacatatg cccatatgct ggctgccatg aacaaaggtt ggctataaag    240
aggtcatcag tatatgaaac agccccctgc tgtccattcc ttattccata gaaaagcctt    300
gacttgaggt tagatttttt ttatattttg tttttgtgtta tttttttctt taacatccct    360 aaaatttttcc ttacatgttt tactagccag attttcctc ctctcctgac tactcccagt    420
catagctgtc cctcttctct tatggagatc                                    450
```

<210> SEQ ID NO 31
<211> LENGTH: 31
<212> TYPE: DNA

```
<213> ORGANISM: Artificial Sequence
<220> FEATURE:
<223> OTHER INFORMATION: Primer

<400> SEQUENCE: 31
taagcagaat tcatgaattt gccaggaaga t                              31

<210> SEQ ID NO 32
<211> LENGTH: 36
<212> TYPE: DNA
<213> ORGANISM: Artificial Sequence
<220> FEATURE:
<223> OTHER INFORMATION: Primer

<400> SEQUENCE: 32
ccatacaatg aatggacact aggcggccgc acgaat                         36

<210> SEQ ID NO 33
<211> LENGTH: 2745
<212> TYPE: DNA
<213> ORGANISM: Artificial Sequence
<220> FEATURE:
<223> OTHER INFORMATION: Gag, Pol, Integrase fragment

<400> SEQUENCE: 33
gaattcatga atttgccagg aagatggaaa ccaaaaatga tagggggaat tggaggtttt    60
atcaaagtaa gacagtatga tcagatactc atagaaatct gcggacataa agctataggt   120
acagtattag taggacctac acctgtcaac ataattggaa gaaatctgtt gactcagatt   180
ggctgcactt taaattttcc cattagtcct attgagactg taccagtaaa attaaagcca   240
ggaatggatg gcccaaaagt taaacaatgg ccattgacag aagaaaaaat aaaagcatta   300
gtagaaattt gtacagaaat ggaaaaggaa ggaaaaattt caaaaattgg gcctgaaaat   360
ccatacaata ctccagtatt tgccataaag aaaaaagaca gtactaaatg gagaaaatta   420
gtagatttca gagaacttaa taagagaact caagatttct gggaagttca attaggaata   480
ccacatcctg cagggttaaa acagaaaaaa tcagtaacag tactggatgt gggcgatgca   540
tatttttcag ttcccttaga taaagacttc aggaagtata ctgcatttac catacctagt   600
ataaacaatg agacaccagg gattagatat cagtacaatg tgcttccaca gggatggaaa   660
ggatcaccag caatattcca gtgtagcatg acaaaaatct tagagccttt tagaaaacaa   720
aatccagaca tagtcatcta tcaatacatg gatgatttgt atgtaggatc tgacttagaa   780
atagggcagc atagaacaaa aatagaggaa ctgagacaac atctgttgag gtggggattt   840
accacaccag acaaaaaaca tcagaaagaa cctccattcc tttggatggg ttatgaactc   900
catcctgata atggacagt acagcctata gtgctgccag aaaaggacag ctggactgtc   960
aatgacatac agaaattagt gggaaaattg aattgggcaa gtcagattta tgcagggatt  1020
aaagtaaggc aattatgtaa acttcttagg ggaaccaaag cactaacaga agtagtacca  1080
ctaacagaag aagcagagct agaactggca gaaaacaggg agattctaaa agaaccggta  1140
catggagtgt attatgaccc atcaaaagac ttaatagcag aaatacagaa gcaggggcaa  1200
ggccaatgga catatcaaat ttatcaagag ccatttaaaa atctgaaaac aggaaagtat  1260
gcaagaatga agggtgccca cactaatgat gtgaaacaat taacagaggc agtacaaaaa  1320
atagccacag aaagcatagt aatatgggga aagactccta aatttaaatt acccatacaa  1380
aaggaaacat gggaagcatg gtggacagag tattggcaag ccacctggat tcctgagtgg  1440
gagtttgtca atacccctcc cttagtgaag ttatggtacc agttagagaa agaacccata  1500
```

```
ataggagcag aaactttcta tgtagatggg gcagccaata gggaaactaa attaggaaaa    1560
gcaggatatg taactgacag aggaagacaa aaagttgtcc ccctaacgga cacaacaaat    1620
cagaagactg agttacaagc aattcatcta gctttgcagg attcgggatt agaagtaaac    1680
atagtgacag actcacaata tgcattggga atcattcaag cacaaccaga taagagtgaa    1740
tcagagttag tcagtcaaat aatagagcag ttaataaaaa aggaaaaagt ctacctggca    1800
tgggtaccag cacacaaagg aattggagga aatgaacaag tagataaatt ggtcagtgct    1860
ggaatcagga aagtactatt tttagatgga atagataagg cccaagaaga acatgagaaa    1920
tatcacagta attggagagc aatggctagt gattttaacc taccacctgt agtagcaaaa    1980
gaaatagtag ccagctgtga taaatgtcag ctaaaagggg aagccatgca tggacaagta    2040
gactgtagcc caggaatatg gcagctagat tgtacacatt tagaaggaaa agttatcttg    2100
gtagcagttc atgtagccag tggatatata gaagcagaag taattccagc agagacaggg    2160
caagaaacag catacttcct cttaaaatta gcaggaagat ggccagtaaa aacagtacat    2220
acagacaatg gcagcaattt caccagtact acagttaagg ccgcctgttg gtgggcgggg    2280
atcaagcagg aatttggcat tccctacaat ccccaaagtc aaggagtaat agaatctatg    2340
aataaagaat taagaaaaat tataggacag gtaagagatc aggctgaaca tcttaagaca    2400
gcagtacaaa tggcagtatt catccacaat tttaaaagaa aaggggggat tggggggtac    2460
agtgcagggg aaagaatagt agacataata gcaacagaca tacaaactaa agaattacaa    2520
aaacaaatta caaaaattca aaattttcgg gtttattaca gggacagcag agatccagtt    2580
tggaaaggac cagcaaagct cctctggaaa ggtgaagggg cagtagtaat acaagataat    2640
agtgacataa aagtagtgcc aagaagaaaa gcaaagatca tcagggatta tggaaaacag    2700
atggcaggtg atgattgtgt ggcaagtaga caggatgagg attaa                    2745
```

<210> SEQ ID NO 34
<211> LENGTH: 1586
<212> TYPE: DNA
<213> ORGANISM: Artificial Sequence
<220> FEATURE:
<223> OTHER INFORMATION: DNA Fragment containing Rev, RRE and rabbit
      beta globin poly A

<400> SEQUENCE: 34

```
tctagaatgg caggaagaag cggagacagc gacgaagagc tcatcagaac agtcagactc      60
atcaagcttc tctatcaaag caacccacct cccaatcccg aggggacccg acaggcccga     120
aggaatagaa gaagaaggtg gagagagaga cagagacaga tccattcgat tagtgaacgg     180
atccttggca cttatctggg acgatctgcg gagcctgtgc ctcttcagct accaccgctt     240
gagagactta ctcttgattg taacgaggat tgtggaactt ctgggacgca gggggtggga     300
agccctcaaa tattggtgga atctcctaca atattggagt caggagctaa agaatagagg     360
agctttgttc cttgggttct tgggagcagc aggaagcact atgggcgcag cgtcaatgac     420
gctgacggta caggccagac aattattgtc tggtatagtg cagcagcaga caatttgct      480 gagggctatt gaggcgcaac agcatctgtt gcaactcaca gtctgggggca tcaagcagct     540 ccaggcaaga atcctggctg tggaaagata cctaaaggat caacagctcc tagatctttt     600
tccctctgcc aaaaattatg gggacatcat gaagcccctt gagcatctga cttctggcta     660
ataaaggaaa tttattttca ttgcaatagt gtgttggaat ttttgtgtc tctcactcgg      720 aaggacatat gggagggcaa atcatttaaa acatcagaat gagtatttgg tttagagttt     780
```

-continued

```
ggcaacatat gccatatgct ggctgccatg aacaaaggtg gctataaaga ggtcatcagt        840
atatgaaaca gcccctgct gtccattcct tattccatag aaaagccttg acttgaggtt         900
agattttttt tatattttgt tttgtgttat tttttctt aacatcccta aaattttcct          960
tacatgtttt actagccaga ttttcctcc tctcctgact actcccagtc atagctgtcc        1020
ctcttctctt atgaagatcc ctcgacctgc agcccaagct tggcgtaatc atggtcatag       1080
ctgtttcctg tgtgaaattg ttatccgctc acaattccac acaacatacg agccggaagc       1140
ataaagtgta aagcctgggg tgcctaatga gtgagctaac tcacattaat tgcgttgcgc       1200
tcactgcccg ctttccagtc gggaaacctg tcgtgccagc ggatccgcat ctcaattagt       1260
cagcaaccat agtcccgccc ctaactccgc ccatcccgcc cctaactccg cccagttccg       1320
cccattctcc gccccatggc tgactaattt ttttttattta gcagaggcc gaggccgcct       1380
cggcctctga gctattccag aagtagtgag gaggcttttt tggaggccta ggcttttgca      1440
aaaagctaac ttgtttattg cagcttataa tggttacaaa taaagcaata gcatcacaaa      1500
tttcacaaat aaagcatttt tttcactgca ttctagttgt ggtttgtcca aactcatcaa      1560
tgtatcttat cagcggccgc cccggg                                           1586
```

<210> SEQ ID NO 35
<211> LENGTH: 1614
<212> TYPE: DNA
<213> ORGANISM: Artificial Sequence
<220> FEATURE:
<223> OTHER INFORMATION: DNA fragment containing the CAG
      enhancer/promoter/intron sequence

<400> SEQUENCE: 35

```
acgcgttagt tattaatagt aatcaattac ggggtcatta gttcatagcc catatatgga        60
gttccgcgtt acataactta cggtaaatgg cccgcctggc tgaccgccca acgaccccg        120
cccattgacg tcaataatga cgtatgttcc catagtaacg ccaatagga ctttccattg        180
acgtcaatgg gtggactatt tacggtaaac tgcccacttg gcagtacatc aagtgtatca      240
tatgccaagt acgccccta ttgacgtcaa tgacggtaaa tggcccgcct ggcattatgc       300
ccagtacatg accttatggg actttcctac ttggcagtac atctacgtat tagtcatcgc      360
tattaccatg gtcgaggtg agccccacgt tctgcttcac tctccccatc tccccccct      420
ccccacccc aattttgtat ttatttattt tttaattatt ttgtgcagcg atgggggcgg     480
gggggggggg ggcgcgcgcc aggcggggcg gggcggggcg aggggcgggg cggggcgagg      540
cggagaggtg cggcggcagc caatcagagc ggcgcgctcc gaaagtttcc ttttatggcg      600
aggcggcggc ggcggcggcc ctataaaaag cgaagcgcgc ggcgggcggg agtcgctgcg     660
ttgccttcgc cccgtgcccc gctccgcgcc gcctcgcgcc gcccgccccg gctctgactg      720
accgcgttac tcccacaggt gagcgggcgg gacggccctt ctcctccggg ctgtaattag      780
cgcttggttt aatgacggct cgtttctttt ctgtggctgc gtgaaagcct taaagggctc      840
cgggagggcc ctttgtgcgg gggggagcgg ctcgggggt gcgtgcgtgt gtgtgtgcgt       900
ggggagcgcc gcgtgcggcc cgcgctgccc ggcggctgtg agcgctgcgg gcgcggcgcg      960
gggctttgtg cgctccgcgt gtgcgcgagg ggagcgcggc cggggcggt gccccgcggt     1020
gcggggggc tgcgagggga acaaaggctg cgtgcgggt gtgtgcgtgg gggtgagc         1080
aggggtgtg ggcgcggcgg tcgggctgta acccccccct gcaccccct ccccgagttg      1140
ctgagcacgg cccggcttcg ggtgcgggc tccgtgcggg gcgtggcgcg ggctcgccg     1200
```

```
tgccgggcgg ggggtggcgg caggtggggg tgccgggcgg ggcggggccg cctcgggccg    1260
gggagggctc gggggagggg cgcggcggcc ccggagcgcc ggcggctgtc gaggcgcggc    1320
gagccgcagc cattgccttt tatggtaatc gtgcgagagg gcgcagggac ttcctttgtc    1380
ccaaatctgg cggagccgaa atctggggag cgccgccgca ccccctctag cgggcgcggg    1440
cgaagcggtg cggcgccggc aggaaggaaa tgggcgggga gggccttcgt gcgtcgccgc    1500
gccgccgtcc ccttctccat ctccagcctc ggggctgccg caggggggacg gctgccttcg    1560 gggggggacgg ggcagggcgg ggttcggctt ctggcgtgtg accggcggga attc          1614
```

<210> SEQ ID NO 36
<211> LENGTH: 884
<212> TYPE: DNA
<213> ORGANISM: Artificial Sequence
<220> FEATURE:
<223> OTHER INFORMATION: RSV promoter and HIV Rev

<400> SEQUENCE: 36

```
caattgcgat gtacgggcca gatatacgcg tatctgaggg gactagggtg tgtttaggcg     60
aaaagcgggg cttcggttgt acgcggttag gagtcccctc aggatatagt agtttcgctt    120
ttgcataggg aggggggaaat gtagtcttat gcaatacact tgtagtcttg caacatggta    180
acgatgagtt agcaacatgc cttacaagga gagaaaaagc accgtgcatg ccgattggtg    240
gaagtaaggt ggtacgatcg tgccttatta ggaaggcaac agacaggtct gacatggatt    300
ggacgaacca ctgaattccg cattgcagag ataattgtat ttaagtgcct agctcgatac    360
aataaacgcc atttgaccat tcaccacatt ggtgtgcacc tccaagctcg agctcgttta    420
gtgaaccgtc agatcgcctg gagacgccat ccacgctgtt ttgacctcca tagaagacac    480
cgggaccgat ccagcctccc ctcgaagcta gcgattaggc atctcctatg gcaggaagaa    540
gcggagacag cgacgaagaa ctcctcaagg cagtcagact catcaagttt ctctatcaaa    600
gcaacccacc tcccaatccc gaggggaccc gacaggcccg aaggaataga agaagaaggt    660
ggagagagag acagagacag atccattcga ttagtgaacg gatccttagc acttatctgg    720
gacgatctgc ggagcctgtg cctcttcagc taccaccgct tgagagactt actcttgatt    780
gtaacgagga ttgtggaact tctgggacgc aggggtggg aagccctcaa atattggtgg    840
aatctcctac aatattggag tcaggagcta aagaatagtc taga                     884
```

<210> SEQ ID NO 37
<211> LENGTH: 1104
<212> TYPE: DNA
<213> ORGANISM: Artificial Sequence
<220> FEATURE:
<223> OTHER INFORMATION: Elongation Factor-1 alpha (EF1-alpha) promoter

<400> SEQUENCE: 37

```
ccggtgccta gagaaggtgg cgcggggtaa actgggaaag tgatgtcgtg tactggctcc     60
gcctttttcc cgagggtggg ggagaaccgt atataagtgc agtagtcgcc gtgaacgttc    120
tttttcgcaa cgggtttgcc gccagaacac aggtaagtgc cgtgtgtggt tcccgcgggc    180
ctggcctctt tacgggttat ggcccttgcg tgccttgaat tacttccacg cccctggctg    240
cagtacgtga ttcttgatcc cgagcttcgg gttggaagtg ggtgggagag ttcgaggcct    300
tgcgcttaag gagccccttc gcctcgtgct tgagttgagg cctggcctgg gcgctggggc    360
cgccgcgtgc gaatctggtg gcaccttcgc gcctgtctcg ctgctttcga taagtctcta    420
```

```
gccatttaaa attttttgatg acctgctgcg acgcttttt tctggcaaga tagtcttgta    480
aatgcgggcc aagatctgca cactggtatt tcggttttg gggccgcggg cggcgacggg    540
gcccgtgcgt cccagcgcac atgttcggcg aggcggggcc tgcgagcgcg ccaccgaga    600 atcggacggg ggtagtctca agctggccgg cctgctctgg tgcctggcct cgcgccgccg    660
tgtatcgccc cgccctgggc ggcaaggctg gcccggtcgg caccagttgc gtgagcggaa    720
agatggccgc ttcccggccc tgctgcaggg agctcaaaat ggaggacgcg cgctcggga    780 gagcgggcgg gtgagtcacc cacacaaagg aaaagggcct ttccgtcctc agccgtcgct    840
tcatgtgact ccacggagta ccgggcgccg tccaggcacc tcgattagtt ctcgagcttt    900
tggagtacgt cgtctttagg ttggggggag gggttttatg cgatggagtt tccccacact    960
gagtgggtgg agactgaagt taggccagct tggcacttga tgtaattctc cttggaattt   1020
gccctttttg agtttggatc ttggttcatt ctcaagcctc agacagtggt tcaaagtttt   1080
tttcttccat ttcaggtgtc gtga                                          1104
```

<210> SEQ ID NO 38
<211> LENGTH: 511
<212> TYPE: DNA
<213> ORGANISM: Artificial Sequence
<220> FEATURE:
<223> OTHER INFORMATION: Promoter - PGK

<400> SEQUENCE: 38

```
ggggttgggg ttgcgccttt tccaaggcag ccctgggttt gcgcagggac gcggctgctc     60
tgggcgtggt tccgggaaac gcagcggcgc cgaccctggg tctcgcacat tcttcacgtc    120
cgttcgcagc gtcacccgga tcttcgccgc taccttgtg ggcccccgg cgacgcttcc     180 tgctccgccc ctaagtcggg aaggttcctt gcggttcgcg gcgtgccgga cgtgacaaac    240
ggaagccgca cgtctcacta gtaccctcgc agacggacag cgccagggag caatggcagc    300
gcgccgaccg cgatgggctg tggccaatag cggctgctca gcaggcgcg ccgagagcag     360 cggccgggaa ggggcggtgc gggaggcggg gtgtgggcg gtagtgtggg ccctgttcct    420
gcccgcgcgc tgttccgcat tctgcaagcc tccggagcgc acgtcggcag tcggctccct    480
cgttgaccga atcaccgacc tctctccccca g                                  511
```

<210> SEQ ID NO 39
<211> LENGTH: 1162
<212> TYPE: DNA
<213> ORGANISM: Artificial Sequence
<220> FEATURE:
<223> OTHER INFORMATION: Promoter - UbC

<400> SEQUENCE: 39

```
gcgccgggtt ttggcgcctc ccgcgggcgc ccccctcctc acggcgagcg ctgccacgtc     60
agacgaaggg cgcaggagcg ttcctgatcc ttccgcccgg acgctcagga cagcggcccg    120
ctgctcataa gactcggcct tagaaccca gtatcagcag aaggacattt taggacggga    180
cttgggtgac tctagggcac tggttttctt tccagagagc ggaacaggcg aggaaaagta    240
gtcccttctc ggcgattctg cggagggatc tccgtgggc ggtgaacgcc gatgattata    300
taaggacgcg ccgggtgtgg cacagctagt tccgtcgcag ccgggatttg ggtcgcggtt    360 cttgttttgtg gatcgctgtg atcgtcactt ggtgagttgc gggctgctgg gctggccggg    420
gctttcgtgg ccgccgggcc gctcggtggg acgaagcgt gtgagagac cgccaagggc    480 tgtagtctgg gtccgcgagc aaggttgccc tgaactgggg gttgggggga gcgcacaaaa    540
```

```
tggcggctgt tcccgagtct tgaatggaag acgcttgtaa ggcggctgt gaggtcgttg      600 aaacaaggtg gggggcatgg tgggcggcaa gaacccaagg tcttgaggcc ttcgctaatg      660
cgggaaagct cttattcggg tgagatgggc tggggcacca tctggggacc ctgacgtgaa      720
gtttgtcact gactgagaaa ctcggtttg tcgtctggtt gcggggcgg cagttatgcg       780 gtgccgttgg gcagtgcacc cgtacctttg ggagcgcgcg cctcgtcgtg tcgtgacgtc      840
acccgttctg ttggcttata atgcaggtg gggccacctg ccgtaggtg tgcggtaggc       900 ttttctccgt cgcaggacgc agggttcggg cctagggtag gctctcctga atcgacaggc      960
gccggacctc tggtgagggg agggataagt gaggcgtcag tttctttggt cggttttatg     1020
tacctatctt cttaagtagc tgaagctccg gttttgaact atgcgctcgg ggttggcgag     1080
tgtgttttgt gaagtttttt aggcaccttt tgaaatgtaa tcatttgggt caatatgtaa     1140
ttttcagtgt tagactagta aa                                              1162

<210> SEQ ID NO 40
<211> LENGTH: 120
<212> TYPE: DNA
<213> ORGANISM: Artificial Sequence
<220> FEATURE:
<223> OTHER INFORMATION: Poly A - SV40

<400> SEQUENCE: 40
gtttattgca gcttataatg gttacaaata aagcaatagc atcacaaatt tcacaaataa       60
agcatttttt tcactgcatt ctagttgtgg tttgtccaaa ctcatcaatg tatcttatca      120

<210> SEQ ID NO 41
<211> LENGTH: 227
<212> TYPE: DNA
<213> ORGANISM: Artificial Sequence
<220> FEATURE:
<223> OTHER INFORMATION: Poly A - bGH

<400> SEQUENCE: 41
gactgtgcct tctagttgcc agccatctgt tgtttgcccc tcccccgtgc cttccttgac       60
cctggaaggt gccactccca ctgtcctttc ctaataaaat gaggaaattg catcgcattg      120
tctgagtagg tgtcattcta ttctgggggg tggggtgggg caggacagca agggggagga     180
ttgggaagac aatagcaggc atgctgggga tgcggtgggc tctatgg                   227

<210> SEQ ID NO 42
<211> LENGTH: 1695
<212> TYPE: DNA
<213> ORGANISM: Artificial Sequence
<220> FEATURE:
<223> OTHER INFORMATION: Envelope - RD114

<400> SEQUENCE: 42
atgaaactcc caacaggaat ggtcattta tgtagcctaa taatagttcg ggcagggttt       60
gacgaccccc gcaaggctat cgcattagta caaaaacaac atggtaaacc atgcgaatgc     120
agcggagggc aggtatccga ggccccaccg aactccatcc aacaggtaac ttgcccaggc     180
aagacggcct acttaatgac caaccaaaaa tggaaatgca gagtcactcc aaaaaatctc     240
acccctagcg ggggagaact ccagaactgc ccctgtaaca cttccagga ctcgatgcac     300 agttcttgtt atactgaata ccggcaatgc aggcgaata taagacata ctacacggcc      360 accttgctta aaatacggtc tgggagcctc aacgaggtac agatattaca aaaccccaat    420
```

```
cagctcctac agtccccttg tagggctct ataaatcagc ccgtttgctg gagtgccaca    480
gcccccatcc atatctccga tggtggagga cccctcgata ctaagagagt gtggacagtc    540
caaaaaaggc tagaacaaat tcataaggct atgcatcctg aacttcaata ccacccctta    600
gccctgccca agtcagaga tgaccttagc cttgatgcac ggactttga tatcctgaat    660 accacttta ggttactcca gatgtccaat tttagccttg cccaagattg ttggctctgt    720
ttaaaactag gtaccctac ccctcttgcg atacccactc cctctttaac ctactcccta    780
gcagactccc tagcgaatgc ctcctgtcag attatacctc ccctcttggt tcaaccgatg    840
cagttctcca actcgtcctg tttatcttcc cctttcatta acgatacgga acaaatagac    900
ttaggtgcag tcacctttac taactgcacc tctgtagcca atgtcagtag tcctttatgt    960
gccctaaacg ggtcagtctt cctctgtgga ataacatgg catacaccta tttaccccaa   1020
aactggacag gactttgcgt ccaagcctcc ctcctccccg acattgacat catcccgggg   1080
gatgagccag tccccattcc tgccattgat cattatatac atagacctaa acgagctgta   1140
cagttcatcc ctttactagc tggactggga atcaccgcag cattcaccac cggagctaca   1200
ggcctaggtg tctccgtcac ccagtataca aaattatccc atcagttaat atctgatgtc   1260
caagtcttat ccggtaccat acaagattta caagaccagg tagactcgtt agctgaagta   1320
gttctccaaa ataggagggg actggaccta ctaacggcag aacaaggagg aatttgttta   1380
gccttacaag aaaaatgctg ttttatgct aacaagtcag gaattgtgag aaacaaaata   1440
agaaccctac aagaagaatt acaaaaacgc agggaaagcc tggcatccaa ccctctctgg   1500
accgggctgc agggctttct tccgtacctc ctacctctcc tgggacccct actcaccctc   1560
ctactcatac taaccattgg gccatgcgtt ttcaatcgat tggtccaatt tgttaaagac   1620
aggatctcag tggtccaggc tctggttttg actcagcaat atcaccagct aaaacccata   1680
gagtacgagc catga                                                    1695

<210> SEQ ID NO 43
<211> LENGTH: 2013
<212> TYPE: DNA
<213> ORGANISM: Artificial Sequence
<220> FEATURE:
<223> OTHER INFORMATION: Envelope - GALV

<400> SEQUENCE: 43
atgcttctca cctcaagccc gcaccacctt cggcaccaga tgagtcctgg gagctggaaa     60
agactgatca tcctcttaag ctgcgtattc ggagacggca aaacgagtct gcagaataag    120
aacccccacc agcctgtgac cctcacctgg caggtactgt cccaaactgg ggacgttgtc    180
tgggacaaaa aggcagtcca gccccttttgg acttggtggc cctctcttac acctgatgta    240
tgtgccctgg cggccggtct tgagtcctgg gatatcccgg gatccgatgt atcgtcctct    300
aaaagagtta gacctcctga ttcagactat actgccgctt ataagcaaat ccctggggga    360
gccatagggt gcagctaccc tcgggctagg accaggatgg caaattcccc cttctacgtg    420
tgtccccgag ctggccgaac ccattcagaa gctaggaggt gtgggggct agaatcccta    480 tactgtaaag aatggagttg tgagaccacg gtaccgtttt attggcaacc caagtcctca    540
tgggacctca taactgtaaa atgggaccaa atgtgaaat gggagcaaaa atttcaaaag    600
tgtgaacaaa ccggctggtg taaccccctc aagatagact tcacagaaaa aggaaaactc    660
tccagagatt ggataacgga aaaaacctgg gaattaaggt tctatgtata tggacaccca    720
ggcatacagt tgactatccg cttagaggtc actaacatgc cggttgtggc agtgggccca    780
```

```
gaccctgtcc ttgcggaaca gggacctcct agcaagcccc tcactctccc tctctcccca    840
cggaaagcgc cgcccacccc tctaccccg gcggctagtg agcaaacccc tgcggtgcat     900
ggagaaactg ttaccctaaa ctctccgcct cccaccagtg gcgaccgact ctttggcctt    960
gtgcaggggg ccttcctaac cttgaatgct accaacccag gggccactaa gtcttgctgg   1020
ctctgtttgg gcatgagccc cccttattat gaagggatag cctcttcagg agaggtcgct   1080
tatacctcca accataccg atgccactgg ggggcccaag aaagcttac cctcactgag     1140 gtctccggac tcgggtcatg catagggaag gtgcctctta cccatcaaca tctttgcaac   1200
cagaccttac ccatcaattc ctctaaaaac catcagtatc tgctcccctc aaaccatagc   1260
tggtgggcct gcagcactgg cctcaccccc tgcctctcca cctcagtttt taatcagtct   1320
aaagacttct gtgtccaggt ccagctgatc ccccgcatct attaccattc tgaagaaacc   1380
ttgttacaag cctatgacaa atcacccccc aggtttaaaa gagagcctgc ctcacttacc   1440
ctagctgtct cctgggggtt agggattgcg gcaggtatag gtactggctc aaccgcccta   1500
attaaagggc ccatagacct ccagcaaggc ctaaccagcc tccaaatcgc cattgacgct   1560
gacctccggg cccttcagga ctcaatcagc aagctagagg actcactgac ttccctatct   1620
gaggtagtac tccaaaatag gagaggcctt gacttactat tccttaaaga aggaggcctc   1680
tgcgcggccc taaaagaaga gtgctgtttt tatgtagacc actcaggtgc agtacgagac   1740
tccatgaaaa aacttaaaga aagactagat aaaagacagt tagagcgcca gaaaaaccaa   1800
aactggtatg aagggtggtt caataactcc ccttggttta ctaccctact atcaaccatc   1860
gctgggcccc tattgctcct ccttttgtta ctcactcttg ggccctgcat catcaataaa   1920
ttaatccaat tcatcaatga taggataagt gcagtcaaaa ttttagtcct tagacagaaa   1980
tatcagaccc tagataacga ggaaaacctt taa                                2013
```

<210> SEQ ID NO 44
<211> LENGTH: 1530
<212> TYPE: DNA
<213> ORGANISM: Artificial Sequence
<220> FEATURE:
<223> OTHER INFORMATION: Envelope - FUG

<400> SEQUENCE: 44

```
atggttccgc aggttctttt gtttgtactc cttctgggtt tttcgttgtg tttcgggaag     60
ttccccattt acacgatacc agacgaactt ggtccctgga gccctattga catacaccat    120
ctcagctgtc caaataacct ggttgtggag gatgaaggat gtaccaacct gtccgagttc    180
tcctacatgg aactcaaagt gggatacatc tcagccatca agtgaacgg gttcacttgc    240 acaggtgttg tgacagaggc agagacctac accaactttg ttggttatgt cacaaccaca    300
ttcaagagaa agcatttccg ccccacccca gacgcatgta gagccgcgta taactggaag    360
atggccggtg accccagata tgaagagtcc ctacacaatc cataccccga ctaccactgg    420
cttcgaactg taagaaccac caaagagtcc ctcattatca tatccccaag tgtgacagat    480
ttggacccat atgacaaatc ccttcactca agggtcttcc ctggcggaaa gtgctcagga    540
ataacggtgt cctctaccta ctgctcaact aaccatgatt acaccatttg gatgcccgag    600
aatccgagac aaggacacc ttgtgacatt tttaccaata gcagagggaa gagagcatcc    660
aacgggaaca agacttgcgg ctttgtggat gaaagaggcc tgtataagtc tctaaaagga    720
gcatgcaggc tcaagttatg tggagttctt ggacttagac ttatggatgg aacatgggtc    780
```

-continued

```
gcgatgcaaa catcagatga gaccaaatgg tgccctccag atcagttggt gaatttgcac    840
gactttcgct cagacgagat cgagcatctc gttgtggagg agttagttaa gaaaagagag    900
gaatgtctgg atgcattaga gtccatcatg accaccaagt cagtaagttt cagacgtctc    960
agtcacctga gaaaacttgt cccagggttt ggaaaagcat ataccatatt caacaaaacc   1020
ttgatggagg ctgatgctca ctacaagtca gtccggacct ggaatgagat catcccctca   1080
aaagggtgtt tgaaagttgg aggaaggtgc catcctcatg tgaacggggt gtttttcaat   1140
ggtataatat tagggcctga cgaccatgtc ctaatcccag agatgcaatc atccctcctc   1200
cagcaacata tggagttgtt ggaatcttca gttatccccc tgatgcaccc cctggcagac   1260
ccttctacag ttttcaaaga aggtgatgag gctgaggatt ttgttgaagt tcacctcccc   1320
gatgtgtaca aacagatctc aggggttgac ctgggtctcc cgaactgggg aaagtatgta   1380
ttgatgactg caggggccat gattggcctg gtgttgatat tttccctaat gacatggtgc   1440
agagttggta tccatctttg cattaaatta aagcacacca agaaaagaca gatttataca   1500
gacatagaga tgaaccgact tggaaagtaa                                    1530
```

<210> SEQ ID NO 45
<211> LENGTH: 1497
<212> TYPE: DNA
<213> ORGANISM: Artificial Sequence
<220> FEATURE:
<223> OTHER INFORMATION: Envelope - LCMV

<400> SEQUENCE: 45

```
atgggtcaga ttgtgacaat gtttgaggct ctgcctcaca tcatcgatga ggtgatcaac     60
attgtcatta ttgtgcttat cgtgatcacg ggtatcaagg ctgtctacaa ttttgccacc    120
tgtgggatat tcgcattgat cagtttccta cttctggctg gcaggtcctg tggcatgtac    180
ggtcttaagg gacccgacat ttacaaagga gtttaccaat ttaagtcagt ggagtttgat    240
atgtcacatc tgaacctgac catgcccaac gcatgttcag ccaacaactc ccaccattac    300
atcagtatgg ggacttctgg actagaattg accttcacca atgattccat catcagtcac    360
aacttttgca atctgacctc tgccttcaac aaaaagacct ttgaccacac actcatgagt    420
atagtttcga gcctacacct cagtatcaga gggaactcca actataaggc agtatcctgc    480
gacttcaaca atggcataac catccaatac aacttgacat tctcagatcg acaaagtgct    540
cagagccagt gtagaacctt cagaggtaga gtcctagata tgtttagaac tgccttcggg    600
gggaaataca tgaggagtgg ctggggctgg acaggctcag atggcaagac cacctggtgt    660
agccagacga gttaccaata cctgattata caaaatagaa cctgggaaaa ccactgcaca    720
tatgcaggtc cttttgggat gtccaggatt ctcctttccc aagagaagac taagttcttc    780
actaggagac tagcgggcac attcacctgg actttgtcag actcttcagg ggtggagaat    840
ccaggtggtt attgcctgac caaatggatg attcttgctg cagagcttaa gtgtttcggg    900
aacacagcag ttgcgaaatg caatgtaaat catgatgccg aattctgtga catgctgcga    960
ctaattgact acaacaaggc tgctttgagt aagttcaaag aggacgtaga atctgccttg   1020
cacttattca aaacaacagt gaattctttg atttcagatc aactactgat gaggaaccac   1080
ttgagagatc tgatgggggt gccatattgc aattactcaa agttttggta cctagaacat   1140
gcaaagaccg gcgaaactag tgtccccaag tgctggcttg tcaccaatgg ttcttactta   1200
aatgagaccc acttcagtga tcaaatcgaa caggaagccg ataacatgat tacagagatg   1260
ttgaggaagg attacataaa gaggcagggg agtacccccc tagcattgat ggaccttctg   1320
```
atgttttcca catctgcata tctagtcagc atcttcctgc accttgtcaa aataccaaca 1380
cacaggcaca taaaaggtgg ctcatgtcca aagccacacc gattaaccaa caaaggaatt 1440
tgtagttgtg gtgcatttaa ggtgcctggt gtaaaaaccg tctggaaaag acgctga 1497

<210> SEQ ID NO 46
<211> LENGTH: 1692
<212> TYPE: DNA
<213> ORGANISM: Artificial Sequence
<220> FEATURE:
<223> OTHER INFORMATION: Envelope - FPV

<400> SEQUENCE: 46
atgaacactc aaatcctggt tttcgccctt gtggcagtca tccccacaaa tgcagacaaa 60
atttgtcttg gacatcatgc tgtatcaaat ggcaccaaag taaacacact cactgagaga 120
ggagtagaag ttgtcaatgc aacggaaaca gtggagcgga caaacatccc caaaatttgc 180
tcaaaaggga aaagaaccac tgatcttggc caatgcggac tgttagggac cattaccgga 240
ccacctcaat gcgaccaatt tctagaattt tcagctgatc taataatcga gagacgagaa 300
ggaaatgatg tttgttaccc ggggaagttt gttaatgaag aggcattgcg acaaatcctc 360
agaggatcag gtgggattga caaagaaaca atgggattca catatagtgg aataaggacc 420
aacggaacaa ctagtgcatg tagaagatca gggtcttcat tctatgcaga aatggagtgg 480
ctcctgtcaa atacagacaa tgctgctttc ccacaaatga caaaatcata caaaaacaca 540
aggagagaat cagctctgat agtctgggga atccaccatt caggatcaac caccgaacag 600
accaaactat atgggagtgg aaataaactg ataacagtcg ggagttccaa atatcatcaa 660
tcttttgtgc cgagtccagg aacacgaccg cagataaatg gccagtccgg acggattgat 720
tttcattggt tgatcttgga tcccaatgat acagttactt ttagtttcaa tggggctttc 780
atagctccaa atcgtgccag cttcttgagg ggaaagtcca tggggatcca gagcgatgtg 840
caggttgatg ccaattgcga aggggaatgc taccacagtg gagggactat aacaagcaga 900
ttgccttttc aaaacatcaa tagcagagca gttggcaaat gcccaagata tgtaaaacag 960
gaaagtttat tattggcaac tgggatgaag aacgttcccg aaccttccaa aaaaaggaaa 1020
aaaagaggcc tgtttggcgc tatagcaggg tttattgaaa atggttggga aggtctggtc 1080
gacgggtggt acggtttcag gcatcagaat gcacaaggag aaggaactgc agcagactac 1140
aaaagcaccc aatcggcaat tgatcagata accggaaagt taaatagact cattgagaaa 1200
accaaccagc aatttgagct aatagataat gaattcactg aggtggaaaa gcagattggc 1260
aatttaatta actggaccaa agactccatc acagaagtat ggtcttacaa tgctgaactt 1320
cttgtggcaa tggaaaacca gcacactatt gatttggctg attcagagat gaacaagctg 1380
tatgagcgag tgaggaaaca attaagggaa aatgctgaag aggatggcac tggttgcttt 1440
gaaatttttc ataaatgtga cgatgattgt atggctagta taaggaacaa tacttatgat 1500
cacagcaaat acagagaaga agcgatgcaa aatagaatac aaattgaccc agtcaaattg 1560
agtagtggct acaaagatgt gatactttgg tttagcttcg gggcatcatg ctttttgctt 1620
cttgccattg caatgggcct tgttttcata tgtgtgaaga acggaaacat gcggtgcact 1680
atttgtatat aa 1692

<210> SEQ ID NO 47
<211> LENGTH: 1266
<212> TYPE: DNA

<213> ORGANISM: Artificial Sequence
<220> FEATURE:
<223> OTHER INFORMATION: Envelope - RRV

<400> SEQUENCE: 47

```
agtgtaacag agcactttaa tgtgtataag gctactagac catacctagc acattgcgcc      60
gattgcgggg acgggtactt ctgctatagc ccagttgcta tcgaggagat ccgagatgag     120
gcgtctgatg gcatgcttaa gatccaagtc tccgcccaaa taggtctgga caaggcaggc     180
acccacgccc acacgaagct ccgatatatg gctggtcatg atgttcagga atctaagaga     240
gattccttga gggtgtacac gtccgcagcg tgctccatac atgggacgat gggacacttc     300
atcgtcgcac actgtccacc aggcgactac ctcaaggttt cgttcgagga cgcagattcg     360
cacgtgaagg catgtaaggt ccaatacaag cacaatccat tgccggtggg tagagagaag     420
ttcgtggtta gaccacactt tggcgtagag ctgccatgca cctcatacca gctgacaacg     480
gctcccaccg acgaggagat tgacatgcat acaccgccag atataccgga tcgcaccctg     540
ctatcacaga cggcgggcaa cgtcaaaata acagcaggcg gcaggactat caggtacaac     600
tgtacctgcg gccgtgacaa cgtaggcact accagtactg acaagaccat caacacatgc     660
aagattgacc aatgccatgc tgccgtcacc agccatgaca aatggcaatt tacctctcca     720
tttgttccca gggctgatca gacagctagg aaaggcaagg tacacgttcc gttccctctg     780
actaacgtca cctgccgagt gccgttggct cgagcgccgg atgccaccta tggtaagaag     840
gaggtgaccc tgagattaca cccagatcat ccgacgctct tctcctatag gagtttagga     900
gccgaaccgc acccgtacga ggaatgggtt gacaagttct ctgagcgcat catcccagtg     960
acggaagaag ggattgagta ccagtggggc aacaacccgc cggtctgcct gtgggcgcaa    1020
ctgacgaccg agggcaaacc ccatggctgg ccacatgaaa tcattcagta ctattatgga    1080
ctataccccg ccgccactat tgccgcagta tccggggcga gtctgatggc cctcctaact    1140
ctggcggcca catgctgcat gctggccacc gcgaggagaa agtgcctaac accgtacgcc    1200
ctgacgccag gagcggtggt accgttgaca ctggggctgc tttgctgcgc accgagggcg    1260
aatgca                                                              1266
```

<210> SEQ ID NO 48
<211> LENGTH: 2030
<212> TYPE: DNA
<213> ORGANISM: Artificial Sequence
<220> FEATURE:
<223> OTHER INFORMATION: Envelope - Ebola

<400> SEQUENCE: 48

```
atgggtgtta caggaatatt gcagttacct cgtgatcgat tcaagaggac atcattcttt      60
ctttgggtaa ttatcctttt ccaaagaaca ttttccatcc cacttggagt catccacaat     120
agcacattac aggttagtga tgtcgacaaa ctggtttgcc gtgacaaact gtcatccaca     180
aatcaattga gatcagttgg actgaatctc gaagggaatg gagtggcaac tgacgtgcca     240
tctgcaacta aagatggggg cttcaggtcc ggtgtcccac caaggtggt caattatgaa     300
gctggtgaat gggctgaaaa ctgctacaat cttgaaatca aaaaacctga cgggagtgag     360
tgtctaccag cagcgccaga cgggattcgg ggcttccccc ggtgccggta tgtgcacaaa     420
gtatcaggaa cgggaccgtg tgccggagac tttgccttcc acaaagaggg tgctttcttc     480
ctgtatgacc gacttgcttc cacagttatc taccgaggaa cgactttcgc tgaaggtgtc     540
gttgcatttc tgatactgcc ccaagctaag aaggacttct tcagctcaca ccccttgaga     600
```

-continued

```
gagccggtca atgcaacgga ggacccgtct agtggctact attctaccac aattagatat      660
caagctaccg gttttggaac caatgagaca gagtatttgt tcgaggttga caatttgacc      720
tacgtccaac ttgaatcaag attcacacca cagtttctgc tccagctgaa tgagacaata      780
tatacaagtg ggaaaggag caataccacg ggaaaactaa tttggaaggt caaccccgaa       840
attgatacaa caatcgggga gtgggccttc tgggaaacta aaaaaacctc actagaaaaa      900
ttcgcagtga agagttgtct ttcacagctg tatcaaacag agccaaaaac atcagtggtc      960
agagtccggc gcgaacttct tccgacccag ggaccaacac aacaactgaa gaccacaaaa     1020
tcatggcttc agaaaattcc tctgcaatgg ttcaagtgca cagtcaagga agggaagctg     1080
cagtgtcgca tctgacaacc cttgccacaa tctccacgag tcctcaaccc cccacaacca     1140
aaccaggtcc ggacaacagc acccacaata caccgtgta taaacttgac atctctgagg      1200
caactcaagt tgaacaacat caccgcagaa cagacaacga cagcacagcc tccgacactc     1260
cccccgccac gaccgcagcc ggaccctaa aagcagagaa caccaacacg agcaagggta      1320
ccgacctcct ggaccccgcc accacaacaa gtccccaaaa ccacagcgag accgctggca     1380
acaacaacac tcatcaccaa gataccggag aagagagtgc cagcagcggg aagctaggct     1440
taattaccaa tactattgct ggagtcgcag gactgatcac aggcgggagg agagctcgaa     1500
gagaagcaat tgtcaatgct caacccaaat gcaaccctaa tttacattac tggactactc     1560
aggatgaagg tgctgcaatc ggactggcct ggataccata tttcgggcca gcagccgagg     1620
gaatttacat agaggggctg atgcacaatc aagatggttt aatctgtggg ttgagacagc     1680
tggccaacga gacgactcaa gctcttcaac tgttcctgag agccacaacc gagctacgca     1740 cctttcaat cctcaaccgt aaggcaattg atttcttgct gcagcgatgg ggcggcacat      1800
gccacatttt gggaccggac tgctgtatcg aaccacatga ttggaccaag aacataacag     1860
acaaaattga tcagattatt catgattttg ttgataaaac ccttccggac caggggggaca    1920 atgacaattg gtggacagga tggagacaat ggataccggc aggtattgga gttacaggcg     1980
ttataattgc agttatcgct ttattctgta tatgcaaatt tgtcttttag                2030
```

<210> SEQ ID NO 49  
<211> LENGTH: 21  
<212> TYPE: DNA  
<213> ORGANISM: Artificial Sequence  
<220> FEATURE:  
<223> OTHER INFORMATION: FDPS target sequence #1

<400> SEQUENCE: 49

```
gtcctggagt acaatgccat t                                                 21
```

<210> SEQ ID NO 50  
<211> LENGTH: 21  
<212> TYPE: DNA  
<213> ORGANISM: Artificial Sequence  
<220> FEATURE:  
<223> OTHER INFORMATION: FDPS target sequence #2

<400> SEQUENCE: 50

```
gcaggatttc gttcagcact t                                                 21
```

<210> SEQ ID NO 51  
<211> LENGTH: 21  
<212> TYPE: DNA  
<213> ORGANISM: Artificial Sequence  
<220> FEATURE:

<223> OTHER INFORMATION: FDPS target sequence #3

<400> SEQUENCE: 51
gccatgtaca tggcaggaat t                                              21

<210> SEQ ID NO 52
<211> LENGTH: 21
<212> TYPE: DNA
<213> ORGANISM: Artificial Sequence
<220> FEATURE:
<223> OTHER INFORMATION: FDPS target sequence #4

<400> SEQUENCE: 52
gcagaaggag gctgagaaag t                                              21

<210> SEQ ID NO 53
<211> LENGTH: 116
<212> TYPE: DNA
<213> ORGANISM: Artificial Sequence
<220> FEATURE:
<223> OTHER INFORMATION: miR30 FDPS sequence #1

<400> SEQUENCE: 53
aaggtatatt gctgttgaca gtgagcgaca ctttctcagc ctccttctgc gtgaagccac     60
agatggcaga aggaggctga gaaagtgctg cctactgcct cggacttcaa ggggct        116

<210> SEQ ID NO 54
<211> LENGTH: 114
<212> TYPE: DNA
<213> ORGANISM: Artificial Sequence
<220> FEATURE:
<223> OTHER INFORMATION: miR30 FDPS sequence #2

<400> SEQUENCE: 54
aaggtatatt gctgttgaca gtgagcgaca ctttctcagc ctccttctgc gtgaagccac     60
agatggcaga agggctgaga aagtgctgcc tactgcctcg gacttcaagg ggct          114

<210> SEQ ID NO 55
<211> LENGTH: 91
<212> TYPE: DNA
<213> ORGANISM: Artificial Sequence
<220> FEATURE:
<223> OTHER INFORMATION: miR30 FDPS sequence #3

<400> SEQUENCE: 55
tgctgttgac agtgagcgac tttctcagcc tccttctgcg tgaagccaca gatggcagaa     60
ggaggctgag aaagttgcct actgcctcgg a                                   91

<210> SEQ ID NO 56
<211> LENGTH: 115
<212> TYPE: DNA
<213> ORGANISM: Artificial Sequence
<220> FEATURE:
<223> OTHER INFORMATION: miR155 FDPS sequence #1

<400> SEQUENCE: 56
cctggaggct tgctgaaggc tgtatgctga ctttctcagc ctccttctgc ttttggccac     60
tgactgagca gaagggctga gaaagtcagg acacaaggcc tgttactagc actca         115

<210> SEQ ID NO 57
<211> LENGTH: 114
<212> TYPE: DNA
<213> ORGANISM: Artificial Sequence

```
<220> FEATURE:
<223> OTHER INFORMATION: miR21 FDPS sequence #1

<400> SEQUENCE: 57
catctccatg gctgtaccac cttgtcggga ctttctcagc ctccttctgc ctgttgaatc     60
tcatggcaga aggaggcgag aaagtctgac attttggtat ctttcatctg acca          114

<210> SEQ ID NO 58
<211> LENGTH: 114
<212> TYPE: DNA
<213> ORGANISM: Artificial Sequence
<220> FEATURE:
<223> OTHER INFORMATION: miR185 FDPS sequence #1

<400> SEQUENCE: 58
gggcctggct cgagcagggg gcgagggata ctttctcagc ctccttctgc tggtcccctc     60
cccgcagaag gaggctgaga aagtccttcc ctcccaatga ccgcgtcttc gtcg          114

<210> SEQ ID NO 59
<211> LENGTH: 20
<212> TYPE: DNA
<213> ORGANISM: Artificial Sequence
<220> FEATURE:
<223> OTHER INFORMATION: Forward Primer

<400> SEQUENCE: 59
aggaattgat ggcgagaagg                                                 20

<210> SEQ ID NO 60
<211> LENGTH: 22
<212> TYPE: DNA
<213> ORGANISM: Artificial Sequence
<220> FEATURE:
<223> OTHER INFORMATION: Reverse Primer

<400> SEQUENCE: 60
cccaaagagg tcaaggtaat ca                                              22

<210> SEQ ID NO 61
<211> LENGTH: 18
<212> TYPE: DNA
<213> ORGANISM: Artificial Sequence
<220> FEATURE:
<223> OTHER INFORMATION: Forward Primer

<400> SEQUENCE: 61
agcgcggcta cagcttca                                                   18

<210> SEQ ID NO 62
<211> LENGTH: 20
<212> TYPE: DNA
<213> ORGANISM: Artificial Sequence
<220> FEATURE:
<223> OTHER INFORMATION: Reverse Primer

<400> SEQUENCE: 62
ggcgacgtag cacagcttct                                                 20

<210> SEQ ID NO 63
<211> LENGTH: 20
<212> TYPE: DNA
<213> ORGANISM: Artificial Sequence
<220> FEATURE:
<223> OTHER INFORMATION: Forward Primer
```

<400> SEQUENCE: 63
cactgtcgtc attccatgct                                          20

<210> SEQ ID NO 64
<211> LENGTH: 19
<212> TYPE: DNA
<213> ORGANISM: Artificial Sequence
<220> FEATURE:
<223> OTHER INFORMATION: Reverse Primer

<400> SEQUENCE: 64
gcctcttgac attctcctc                                           19

<210> SEQ ID NO 65
<211> LENGTH: 20
<212> TYPE: DNA
<213> ORGANISM: Artificial Sequence
<220> FEATURE:
<223> OTHER INFORMATION: Reverse Primer

<400> SEQUENCE: 65
aaagtcagtg gggacagtgg                                          20

<210> SEQ ID NO 66
<211> LENGTH: 117
<212> TYPE: DNA
<213> ORGANISM: Artificial Sequence
<220> FEATURE:
<223> OTHER INFORMATION: miR155 CD47 target sequence #2

<400> SEQUENCE: 66
cctggaggct tgctgaaggc tgtatgctgt tagctcgatg atcgtttcac gttttggcca      60
ctgactgacg tgaaacgcat cgagctaaca ggacacaagg cctgttacta gcactca       117

<210> SEQ ID NO 67
<211> LENGTH: 117
<212> TYPE: DNA
<213> ORGANISM: Artificial Sequence
<220> FEATURE:
<223> OTHER INFORMATION: miR155 CD47 target sequence #3

<400> SEQUENCE: 67
cctggaggct tgctgaaggc tgtatgctga agaatggctc caacaatgac gttttggcca      60
ctgactgacg tcattgtgag ccattcttca ggacacaagg cctgttacta gcactca       117

<210> SEQ ID NO 68
<211> LENGTH: 117
<212> TYPE: DNA
<213> ORGANISM: Artificial Sequence
<220> FEATURE:
<223> OTHER INFORMATION: miR155 CD47 target sequence #4

<400> SEQUENCE: 68
cctggaggct tgctgaaggc tgtatgctgt atacacgccg caatacagag gttttggcca      60
ctgactgacc tctgtatcgg cgtgtataca ggacacaagg cctgttacta gcactca       117

<210> SEQ ID NO 69
<211> LENGTH: 18
<212> TYPE: DNA
<213> ORGANISM: Artificial Sequence
<220> FEATURE:
<223> OTHER INFORMATION: Forward primer

<400> SEQUENCE: 69

```
ggactatcct gctgccaa                                                    18
```

<210> SEQ ID NO 70
<211> LENGTH: 115
<212> TYPE: DNA
<213> ORGANISM: Artificial Sequence
<220> FEATURE:
<223> OTHER INFORMATION: miR155 cMyc sequence

<400> SEQUENCE: 70

```
cctggaggct tgctgaaggc tgtatgctgt gttcgcctct tgacattctc ttttggccac     60
tgactgagag aatgtagagg cgaacacagg acacaaggcc tgttactagc actca         115
```

<210> SEQ ID NO 71
<211> LENGTH: 21
<212> TYPE: DNA
<213> ORGANISM: Artificial Sequence
<220> FEATURE:
<223> OTHER INFORMATION: cMyc target sequence

<400> SEQUENCE: 71

```
gagaatgtca agaggcgaac a                                                21
```

<210> SEQ ID NO 72
<211> LENGTH: 329
<212> TYPE: DNA
<213> ORGANISM: Artificial Sequence
<220> FEATURE:
<223> OTHER INFORMATION: CMV promoter sequence

<400> SEQUENCE: 72

```
attatgccca gtacatgacc ttatgggact ttcctacttg gcagtacatc tacgtattag     60
tcatcgctat taccatggtg atgcggtttt ggcagtacat caatgggcgt ggatagcggt    120
ttgactcacg gggatttcca agtctccacc ccattgacgt caatgggagt ttgttttggc    180
accaaaatca acgggacttt ccaaaatgtc gtaacaactc cgccccattg acgcaaatgg    240
gcggtaggcg tgtacggtgg gaggtttata taagcagagc tcgtttagtg aaccgtcaga    300
tcgcctggag acgccatcca cgctgtttt                                      329
```

<210> SEQ ID NO 73
<211> LENGTH: 2520
<212> TYPE: DNA
<213> ORGANISM: Artificial Sequence
<220> FEATURE:
<223> OTHER INFORMATION: GFP T2A Luciferase sequence

<400> SEQUENCE: 73

```
atgcccgcca tgaagatcga gtgccgcatc accggcaccc tgaacggcgt ggagttcgag     60
ctggtgggcg gcggagaggg cacccccgag cagggccgca tgaccaacaa gatgaagagc    120
accaaaggcg ccctgacctt cagccccrac ctgctgagcc acgtgatggg ctacggcttc    180
taccacttcg gcacctaccc cagcggctac gagaacccct tcctgcacgc catcaacaac    240
ggcggctaca ccaacacccg catcgagaag tacgaggacg gcggcgtgct gcacgtgagc    300
ttcagctacc gctacgaggc cggccgcgtg atcggcgact tcaaggtggt gggcaccggc    360
ttccccgagg acagcgtgat cttcaccgac aagatcatcc gcagcaacgc caccgtggag    420
cacctgcacc ccatgggcga taacgtgctg gtgggcagct tcgcccgcac cttcagcctg    480
cgcgacggcg gctactacag cttcgtggtg gacagccaca tgcacttcaa gagcgccatc    540
```

```
caccccagca tcctgcagaa cggggggcccc atgttcgcct tccgccgcgt ggaggagctg    600
cacagcaaca ccgagctggg catcgtggag taccagcacg ccttcaagac ccccatcgcc    660
ttcgccagat ctcgagatat cagccatggc ttcccgccgg cggtggcggc gcaggatgat    720
ggcacgctgc ccatgtcttg tgcccaggag agcgggatgg accgtcaccc tgcagcctgt    780
gcttctgcta ggatcaatgt gaccggtgag ggcagaggaa gtcttctaac atgcggtgac    840
gtggaggaga tcccggcccc ttccggtatg aagacgccaa aaacataaa gaaaggcccg    900
gcgccattct atccgctaga ggatggaacc gctggagagc aactgcataa ggctatgaag    960
agatacgccc tggttcctgg aacaattgct tttacagatg cacatatcga ggtgaacatc   1020
acgtacgcgg aatacttcga aatgtccgtt cggttggcag aagctatgaa cgatatgggg   1080
ctgaatacaa atcacagaat cgtcgtatgc agtgaaaact ctcttcaatt ctttatgccg   1140
gtgttgggcg cgttatttat cggagttgca gttgcgcccg cgaacgacat ttataatgaa   1200
cgtgaattgc tcaacagtat gaacatttcg cagcctaccg tagtgtttgt ttccaaaaag   1260
gggttgcaaa aaatttttgaa cgtgcaaaaa aaattaccaa taatccagaa aattattatc   1320
atggattcta aaacggatta ccagggattt cagtcgatgt acacgttcgt cacatctcat   1380
ctacctcccg gttttaatga atacgatttt gtaccagagt cctttgatcg tgacaaaaca   1440
attgcactga taatgaactc ctctggatct actgggttac ctaagggtgt ggcccttccg   1500
catagaactg cctgcgtcag attctcgcat gccagagatc ctattttttgg caatcaaatc   1560
attccggata ctgcgatttt aagtgttgtt ccattccatc acggttttgg aatgtttact   1620
acactcggat atttgatatg tggatttcga gtcgtcttaa tgtatagatt tgaagaagag   1680
ctgttttttac gatcccttca ggattacaaa attcaaagtg cgttgctagt accaacccta   1740
tttttcattct tcgccaaaag cactctgatt gacaaatacg atttatctaa tttacacgaa   1800
attgcttctg ggggcgcacc tctttcgaaa gaagtcgggg aagcggttgc aaaacgcttc   1860
catcttccag ggatacgaca aggatatggg ctcactgaga ctacatcagc tattctgatt   1920
acacccgagg gggatgataa accgggcgcg gtcggtaaag ttgttccatt ttttgaagcg   1980
aaggttgtgg atctggatac cgggaaaacg ctgggcgtta atcagagagg cgaattatgt   2040
gtcagaggac ctatgattat gtccggttat gtaaacaatc cggaagcgac caacgccttg   2100
attgacaagg atggatggct acattctgga gacatagctt actgggacga agacgaacac   2160
ttcttcatag ttgaccgctt gaagtcttta attaaataca aaggatacca ggtggcccccc  2220
gctgaattgg agtcgatatt gttacaacac cccaacatct cgacgcgggg cgtggcaggt   2280
cttcccgacg atgacgccgg tgaacttccc gccgccgttg ttgttttgga gcacggaaag   2340
acgatgacgg aaaagagat cgtggattac gtcgccagtc aagtaacaac gcgaaaaag    2400
ttgcgcggag gagttgtgtt tgtggacgaa gtaccgaaag tcttaccgg aaaactcgac   2460
gcaagaaaaa tcagagagat cctcataaag gccaagaagg gcggaaagtc caaattgtaa   2520
```

<210> SEQ ID NO 74
<211> LENGTH: 228
<212> TYPE: DNA
<213> ORGANISM: Artificial Sequence
<220> FEATURE:
<223> OTHER INFORMATION: Rous Sarcoma virus (RSV) promoter

<400> SEQUENCE: 74

```
gtagtcttat gcaatactct tgtagtcttg caacatggta acgatgagtt agcaacatgc      60
cttacaagga gagaaaaagc accgtgcatg ccgattggtg gaagtaaggt ggtacgatcg     120
```

```
tgccttatta ggaaggcaac agacgggtct gacatggatt ggacgaacca ctgaattgcc    180
gcattgcaga gatattgtat ttaagtgcct agctcgatac aataaacg                 228
```

<210> SEQ ID NO 75
<211> LENGTH: 180
<212> TYPE: DNA
<213> ORGANISM: Artificial Sequence
<220> FEATURE:
<223> OTHER INFORMATION: 5' Long terminal repeat (LTR)

<400> SEQUENCE: 75

```
ggtctctctg ttagaccag atctgagcct gggagctctc tggctaacta gggaacccac     60
tgcttaagcc tcaataaagc ttgccttgag tgcttcaagt agtgtgtgcc cgtctgttgt   120
gtgactctgg taactagaga tccctcagac ccttttagtc agtgtggaaa atctctagca   180
```

<210> SEQ ID NO 76
<211> LENGTH: 41
<212> TYPE: DNA
<213> ORGANISM: Artificial Sequence
<220> FEATURE:
<223> OTHER INFORMATION: Psi Packaging signal

<400> SEQUENCE: 76

```
tacgccaaaa attttgacta gcggaggcta aaggagaga g                         41
```

<210> SEQ ID NO 77
<211> LENGTH: 233
<212> TYPE: DNA
<213> ORGANISM: Artificial Sequence
<220> FEATURE:
<223> OTHER INFORMATION: Rev response element (RRE)

<400> SEQUENCE: 77

```
aggagctttg ttccttgggt tcttgggagc agcaggaagc actatgggcg cagcctcaat    60
gacgctgacg gtacaggcca gacaattatt gtctggtata gtgcagcagc agaacaattt   120
gctgagggct attgaggcgc aacagcatct gttgcaactc acagtctggg gcatcaagca   180
gctccaggca agaatcctgg ctgtggaaag atacctaaag gatcaacagc tcc           233
```

<210> SEQ ID NO 78
<211> LENGTH: 118
<212> TYPE: DNA
<213> ORGANISM: Artificial Sequence
<220> FEATURE:
<223> OTHER INFORMATION: Central polypurine tract (cPPT)

<400> SEQUENCE: 78

```
ttttaaaaga aaaggggga ttggggggta cagtgcaggg gaaagaatag tagacataat     60
agcaacagac atacaaacta aagaattaca aaaacaaatt acaaaattca aaattta      118
```

<210> SEQ ID NO 79
<211> LENGTH: 590
<212> TYPE: DNA
<213> ORGANISM: Artificial Sequence
<220> FEATURE:
<223> OTHER INFORMATION: Long WPRE sequence

<400> SEQUENCE: 79

```
aatcaacctc tgattacaaa atttgtgaaa gattgactgg tattcttaac tatgttgctc    60
cttttacgct atgtggatac gctgctttaa tgcctttgta tcatgctatt gcttcccgta   120
```

```
tggctttcat ttctcctcc ttgtataaat cctggttgct gtctctttat gaggagttgt      180
ggcccgttgt caggcaacgt ggcgtggtgt gcactgtgtt tgctgacgca accccactg       240 gttgggcat tgccaccacc tgtcagctcc tttccgggac tttcgctttc ccctcccta       300 ttgccacggc ggaactcatc gccgcctgcc ttgcccgctg ctggacaggg gctcggctgt     360
tgggcactga caattccgtg gtgttgtcgg ggaaatcatc gtcctttcct tggctgctcg     420
cctgtgttgc cacctggatt ctgcgcggga cgtccttctg ctacgtccct tcggccctca    480
atccagcgga ccttccttcc cgcggcctgc tgccggctct gcggcctctt ccgcgtcttc    540
gccttcgccc tcagacgagt cggatctccc tttgggccgc ctccccgcct              590

<210> SEQ ID NO 80
<211> LENGTH: 250
<212> TYPE: DNA
<213> ORGANISM: Artificial Sequence
<220> FEATURE:
<223> OTHER INFORMATION: 3' delta LTR

<400> SEQUENCE: 80
tggaagggct aattcactcc caacgaagat aagatctgct ttttgcttgt actgggtctc     60
tctggttaga ccagatctga gcctgggagc tctctggcta actagggaac ccactgctta   120
agcctcaata agcttgcct tgagtgcttc aagtagtgtg tgcccgtctg ttgtgtgact    180
ctggtaacta gagatccctc agaccctttt agtcagtgtg gaaaatctct agcagtagta   240
gttcatgtca                                                           250

<210> SEQ ID NO 81
<211> LENGTH: 1938
<212> TYPE: DNA
<213> ORGANISM: Artificial Sequence
<220> FEATURE:
<223> OTHER INFORMATION: Envelope - MLV 10A1

<400> SEQUENCE: 81
atggaaggtc cagcgttctc aaaacccctt aaagataaga ttaacccgtg gaagtcctta     60
atggtcatgg gggtctattt aagagtaggg atggcagaga gccccccatca ggtctttaat  120 gtaacctgga gagtcaccaa cctgatgact gggcgtaccg ccaatgccac ctcccttta    180 ggaactgtac aagatgcctt cccaagatta tattttgatc tatgtgatct ggtcggagaa   240
gagtgggacc cttcagacca ggaaccatat gtcgggtatg gctgcaaata ccccggaggg  300
agaaagcgga cccggacttt tgacttttac gtgtgccctg gcataccgt aaaatcgggg   360 tgtggggggc caagagaggg ctactgtggt gaatggggtt gtgaaaccac cggacaggct  420
tactggaagc ccacatcatc atgggaccta atctccctta gcgcggtaa cacccctggg   480 gacacgggat gctccaaaat ggcttgtggc ccctgctacg acctctccaa gtatccaat   540 tccttccaag gggctactcg aggggggcaga tgcaaccctc tagtcctaga attcactgat  600
gcaggaaaaa aggctaattg ggacgggccc aaatcgtggg gactgagact gtaccggaca  660
ggaacagatc ctattaccat gttctccctg accgccagg tcctcaatat agggccccgc   720
atccccattg gcctaatcc cgtgatcact ggtcaactac cccctccg acccgtgcag    780 atcaggctcc ccaggcctcc tcagcctcct cctacaggcg cagcctctat agtccctgag  840
actgccccac cttctcaaca acctgggacg ggagacaggc tgctaaacct ggtagaagga  900
gcctatcagg cgcttaacct caccaatccc gacaagaccc aagaatgttg gctgtgctta  960
gtgtcgggac ctccttatta cgaaggagta gcggtcgtgg gcacttatac caatcattct 1020
```

```
accgccccgg ccagctgtac ggccacttcc aacataagc ttaccctatc tgaagtgaca    1080
ggacagggcc tatgcatggg agcactacct aaaactcacc aggccttatg taacaccacc    1140
caaagtgccg gctcaggatc ctactacctt gcagcacccg ctggaacaat gtgggcttgt    1200
agcactggat tgactccctg cttgtccacc acgatgctca atctaaccac agactattgt    1260
gtattagttg agctctggcc cagaataatt taccactccc ccgattatat gtatggtcag    1320
cttgaacagc gtaccaaata taagagggag ccagtatcgt tgaccctggc ccttctgcta    1380
ggaggattaa ccatgggagg gattgcagct ggaatagggca cggggaccac tgccctaatc    1440 aaacccagc agtttgagca gcttcacgcc gctatccaga cagacctcaa cgaagtcgaa    1500
aaatcaatta ccaacctaga aaagtcactg acctcgttgt ctgaagtagt cctacagaac    1560
cgaagaggcc tagatttgct cttcctaaaa gagggaggtc tctgcgcagc cctaaaagaa    1620
gaatgttgtt tttatgcaga ccacacggga ctagtgagag acagcatggc caaactaagg    1680
gaaaggctta atcagagaca aaaactattt gagtcaggcc aaggttggtt cgaagggcag    1740
tttaatagat cccctggtt taccacctta atctccacca tcatgggacc tctaatagta    1800
ctcttactga tcttactctt tggaccctgc attctcaatc gattggtcca atttgttaaa    1860
gacaggatct cagtggtcca ggctctggtt ttgactcaac aatatcacca gctaaaacct    1920
atagagtacg agccatga                                                  1938

<210> SEQ ID NO 82
<211> LENGTH: 117
<212> TYPE: DNA
<213> ORGANISM: Artificial Sequence
<220> FEATURE:
<223> OTHER INFORMATION: miR155 CD47 target sequence #1

<400> SEQUENCE: 82
cctggaggct tgctgaaggc tgtatgctgt tatccatctt caaagaggca gttttggcca    60
ctgactgact gcctcttaag atggataaca ggacacaagg cctgttacta gcactca      117

<210> SEQ ID NO 83
<211> LENGTH: 114
<212> TYPE: DNA
<213> ORGANISM: Artificial Sequence
<220> FEATURE:
<223> OTHER INFORMATION: miR21 cMyc sequence

<400> SEQUENCE: 83
catctccatg gctgtaccac cttgtcgggt gttcgcctct tgacattctc ctgttgaatc    60
tcatggagaa tgtcaagggc gaacactgac attttggtat ctttcatctg acca          114

<210> SEQ ID NO 84
<211> LENGTH: 1227
<212> TYPE: DNA
<213> ORGANISM: Artificial Sequence
<220> FEATURE:
<223> OTHER INFORMATION: Helper plasmid without Rev

<400> SEQUENCE: 84
tctagaagga gctttgttcc ttgggttctt gggagcagca ggaagcacta tgggcgcagc    60
gtcaatgacg ctgacggtac aggccagaca attattgtct ggtatagtgc agcagcagaa    120
caatttgctg agggctattg aggcgcaaca gcatctgttg caactcacag tctgggggcat    180 caagcagctc caggcaagaa tcctggctgt ggaaagatac ctaaaggatc aacagctcct    240
```

```
agatcttttt ccctctgcca aaaattatgg ggacatcatg aagccccttg agcatctgac    300
ttctggctaa taaaggaaat ttattttcat tgcaatagtg tgttggaatt ttttgtgtct    360
ctcactcgga aggacatatg ggagggcaaa tcatttaaaa catcagaatg agtatttggt    420
ttagagtttg gcaacatatg ccatatgctg gctgccatga acaaaggtgg ctataaagag    480
gtcatcagta tatgaaacag cccctgctg tccattcctt attccataga aaagccttga    540
cttgaggtta gatttttttt atattttgtt ttgtgttatt tttttcttta acatccctaa    600
aattttcctt acatgtttta ctagccagat ttttcctcct ctcctgacta ctcccagtca    660
tagctgtccc tcttctctta tgaagatccc tcgacctgca gcccaagctt ggcgtaatca    720
tggtcatagc tgtttcctgt gtgaaattgt tatccgctca caattccaca caacatacga    780
gccggaagca taaagtgtaa agcctggggt gcctaatgag tgagctaact cacattaatt    840
gcgttgcgct cactgcccgc tttccagtcg ggaaacctgt cgtgccagcg gatccgcatc    900
tcaattagtc agcaaccata gtcccgcccc taactccgcc catcccgccc ctaactccgc    960
ccagttccgc ccattctccg ccccatggct gactaatttt ttttatttat gcagaggccg   1020
aggccgcctc ggcctctgag ctattccaga agtagtgagg aggcttttt ggaggcctag   1080 gcttttgcaa aaagctaact tgtttattgc agcttataat ggttacaaat aaagcaatag   1140
catcacaaat ttcacaaata aagcattttt ttcactgcat tctagttgtg gtttgtccaa   1200
actcatcaat gtatcttatc acccggg                                       1227
```

COMBINATION VECTORS AND METHODS FOR TREATING CANCER

CROSS-REFERENCE TO RELATED APPLICATION

This application claims priority to U.S. patent application Ser. No. 16/943,800, filed on Jul. 30, 2020, and entitled "Combination Vectors and Uses Thereof," which claims priority to U.S. patent application Ser. No. 16/083,384, filed on Sep. 7, 2018, and entitled "Combination Vectors and Uses Thereof," which is a U.S. national stage application of PCT Patent Application No. PCT/US2017/021639, filed on Mar. 9, 2017 entitled "Combination Vectors and Uses Thereof", which claims priority to U.S. Provisional Patent Application No. 62/305,944, filed on Mar. 9, 2016, and entitled "Combination Vectors and Uses Thereof." These applications are incorporated herein by reference in their entirety.

SEQUENCE LISTING

A Sequence Listing is enclosed with this application and is incorporated herein by reference. The text file of the Sequence Listing is named 7061200536_SL.txt and the file size is 65 kilobytes.

FIELD

Aspects of the present disclosure relate to using vectors to treat cancer. More specifically, aspects of the present disclosure relate to using vectors, including combination vectors, to treat cancer.

BACKGROUND

Cancer is a significant healthcare issue for the world's population. As an example, liver cancer in adult men is the fifth most frequently diagnosed cancer worldwide, and is the second leading cause of cancer-related death in the world. Numerous therapeutic strategies have been employed in an effort to effectively treat cancer. Traditional therapeutic approaches have revolved around the use of chemotherapy and radiation therapy.

Chemotherapy refers to the administration of one or more anti-cancer drugs and/or other agents to a cancer patient by various methods. Broadly, most chemotherapeutic drugs work by impairing mitosis (cell division), effectively targeting fast-dividing cells. However, other fast dividing cells such as those responsible for hair growth and for replacement of the intestinal epithelium (lining) are also affected. Because chemotherapy affects cell division, both normal and cancerous cells are susceptible to the cytotoxic effects of chemotherapeutic agents.

Radiation therapy refers to exposing a patient to high-energy radiation, including x-rays, gamma rays, and neutrons. This type of therapy includes without limitation external-beam therapy, internal radiation therapy, implant radiation, brachytherapy, systemic radiation therapy, and radiotherapy. External beam radiation may include three dimensional conformal radiation therapy, intensity modulated radiation therapy, and conformal proton beam radiation therapy. In practice it is difficult to shield the nearby normal tissue from the cytotoxic effects of the radiation and still deliver a therapeutic dose. An additional complication of radiation is the induction of radiation resistant cells during the course of treatment. Thus, even the best radiotherapeutic techniques often result in incomplete tumor reduction and subsequent recurrence.

More recently, immunotherapeutic approaches have been employed in an attempt to harness the power of the host's immune system to treat cancer. For example, strategies have been employed to target cancer-associated antigens with host-based T cells that specifically recognize such antigens. For example, a recent approach has focused on the development and use of chimeric antigen receptor (CAR) T cells (also known as CAR-T cells). Possible side effects associated with CAR-T cell therapy include chemokine-release syndrome, B cell aplasia, and tumor lysis syndrome. Despite the development of these approaches, cancer remains a significant healthcare issue.

SUMMARY

In an aspect of the disclosure, a viral vector comprising a therapeutic cargo portion is disclosed. The therapeutic cargo portion includes at least one small RNA sequence that is capable of binding to at least one pre-determined complementary mRNA sequence, wherein the at least one complementary mRNA sequence comprises a FDPS mRNA sequence. In embodiments, the therapeutic cargo portion may further include a second small RNA sequence that is capable of binding to a second pre-determined complementary mRNA sequence, wherein the second pre-determined complementary mRNA sequence comprises a CD47 mRNA sequence or a cMyc mRNA sequence. In embodiments, the at least one small RNA sequence is under the control of a first promoter and the second small RNA sequence is under the control of a second promoter. In embodiments, the therapeutic cargo portion may further include a third small RNA sequence that is capable of binding to a third pre-determined complementary mRNA sequence, wherein the third pre-determined complementary mRNA sequence comprises a CD47 mRNA sequence or a cMyc mRNA sequence. In embodiments, the at least one small RNA sequence is under the control of a first promoter, the second small RNA sequence is under the control of a second promoter, and the third small RNA sequence is under the control of a third promoter. In embodiments, the small RNA sequences are under the control of a single promoter. In embodiments, the small RNA sequence is a microRNA (miRNA) or a short hairpin RNA (shRNA).

In another aspect, the small RNA sequence comprises a sequence having at least 80%, or at least 85%, or at least 90%, or at least 95% percent identity with a FDPS small RNA sequence comprising GTCCTGGAGTACAATGC-CATTCTCGAGAATGGCATTGTACTCCAGGACTTTT (SEQ ID NO: 1); GCAGGAT-TCGTTCAGCACTTCTCGAGAAGTGCT-GAACGAAATCCTGCTTTTT (SEQ ID NO: 2); GCCATGTACATGGCAGGAATTCTCGAGAAT-TCCTGCCATGTACATGGCTTTTT (SEQ ID NO: 3); or GCAGAAGGAGGCTGAGAAAGTCTCGA-GACTTTCTCAGCCTCCTTCTGCTTTTTT (SEQ ID NO: 4). In embodiments, the small RNA sequence is selected from SEQ ID NOs: 1, 2, 3, or 4.

In another aspect, the second small RNA sequence comprises a sequence having at least 80%, or at least 85%, or at least 90%, or at least 95% percent identity with a CD47 small RNA sequence comprising GGTGAAACGAT-CATCGAGCCTCGAGGCTCGATGATCGTTT-CACCTTTTT (SEQ ID NO: 5); GCTACTGGCCTTGGTT-TAACTCGAGTTAAACCAAGGCCAGTAGCTTTTT (SEQ ID NO: 6); CCTCCTTCGTCATTGCCATCTCGAGATGGCAATGACGAAGGAGGTTTTT (SEQ ID NO: 7); GCATGGCCCTCTTCTGATTCTCGAGAATCAGAAGAGGGCCATGCTTTTT (SEQ ID NO: 8); or GGTGAAACGATCATCGAGCTACTCGAGTAGCTCGATGATCGTTTCACCTTTTT (SEQ ID NO: 9) or a cMyc small RNA sequence comprising GCTTCACCAACAGGAACTATGCTCGAGCATAGTTCCTGTTGGTGAAGCTTTT (SEQ ID NO: 10); GCGAACACACAACGTCTTGGACTCGAGTCCAAGACGTTGTGTGTTCGCTTTT (SEQ ID NO: 11); GACATGGTGAACCAGAGTTTCCTCGAGGAAACTCTGGTTCACCATGTCTTTTT (SEQ ID NO: 12); GAGAATGTCAAGAGGCGAACACTCGAGTGTTCGCCTCTTGACATTCTCTTTT (SEQ ID NO: 13); or GCTCATTTCTGAAGAGGACTTCTCGAGAAGTCCTCTTCAGAAATGAGCTTTTT (SEQ ID NO: 14). In embodiments, the second small RNA sequence is selected from SEQ ID NOs: 5, 6,7,8,9,10,11,12,13, or 14.

In another aspect, the third small RNA sequence comprises a sequence having at least 80%, or at least 85%, or at least 90%, or at least 95% percent identity with a CD47 small RNA sequence comprising SEQ ID NOs: 5, 6, 7, 8, or 9 or a cMyc small RNA sequence comprising SEQ ID NOs: 10, 11, 12, 13, or 14. In embodiments, the third small RNA sequence is selected from SEQ ID NOs: 5, 6, 7, 8, 9, 10, 11, 12, 13, or 14.

In another aspect, a viral vector comprising a therapeutic cargo portion is disclosed. The therapeutic cargo portion includes at least one small RNA sequence that is capable of binding to at least one pre-determined complementary mRNA sequence, wherein the at least one complementary mRNA sequence comprises a CD47 mRNA sequence. In embodiments, the therapeutic cargo portion further comprises a second small RNA sequence that is capable of binding to a second pre-determined complementary mRNA sequence, wherein the second pre-determined complementary mRNA sequence comprises a FDPS mRNA sequence or a cMyc mRNA sequence. In embodiments, the at least one small RNA sequence is under the control of a first promoter and the second small RNA sequence is under the control of a second promoter. In embodiments, the therapeutic cargo portion further comprises a third small RNA sequence that is capable of binding to a third pre-determined complementary mRNA sequence, wherein the third pre-determined complementary mRNA sequence comprises a FDPS mRNA sequence or a cMyc mRNA sequence. The small RNA sequence may be a miRNA or a shRNA. In embodiments, the at least one small RNA sequence is under the control of a first promoter, the second small RNA sequence is under the control of a second promoter, and the third small RNA sequence is under the control of a third promoter. In embodiments, the small RNA sequences are under the control of a single promoter.

In another aspect, the small RNA sequence comprises a sequence having at least 80%, or at least 85%, or at least 90%, or at least 95% percent identity with a CD47 small RNA sequence comprising SEQ ID NOs: 5, 6, 7, 8, or 9. In embodiments, the small RNA sequence is selected from SEQ ID NOs: 5, 6, 7, 8, or 9.

In another aspect, the second small RNA sequence comprises a sequence having at least 80%, or at least 85%, or at least 90%, or at least 95% percent identity with a FDPS small RNA sequence comprising SEQ ID NOs: 1, 2, 3, or 4 or a cMyc small RNA sequence comprising SEQ ID NOs: 10, 11, 12, 13, or 14. In embodiments, the second small RNA sequence is selected from SEQ ID NOs: 1, 2, 3, 4, 10, 11, 12, 13, or 14.

In another aspect, the third small RNA comprises a sequence having at least 80%, or at least 85%, or at least 90%, or at least 95% percent identity with a FDPS small RNA sequence comprising SEQ ID NOs: 1, 2, 3, or 4 or a cMyc small RNA sequence comprising SEQ ID NOs: 10, 11, 12, 13, or 14. In embodiments, the third small RNA sequence is selected from SEQ ID NOs: 1, 2, 3, 4, 10, 11, 12, 13, or 14.

In another aspect, a viral vector comprising a therapeutic cargo portion is disclosed. The therapeutic cargo portion comprises a first small RNA sequence that is capable of binding to a first pre-determined complementary mRNA sequence, and at least one additional small RNA sequence that is capable of binding to a second pre-determined complementary mRNA sequence, wherein the first pre-determined complementary mRNA sequence comprises a cMyc mRNA sequence, and the second pre-determined complementary sequence comprises a FDPS mRNA sequence or a CD47 mRNA sequence.

In another aspect, the therapeutic cargo portion further comprises a third small RNA sequence that is capable of binding to a third pre-determined complementary mRNA sequence, wherein the third pre-determined complementary mRNA sequence comprises a FDPS mRNA sequence or a CD47 mRNA sequence. In embodiments, the small RNA sequences are miRNAs or shRNAs. In embodiments, the first small RNA sequence is under the control of a first promoter, the second small RNA sequence is under the control of a second promoter, and the third small RNA sequence is under the control of a third promoter. In embodiments, the small RNA sequences are under the control of a single promoter.

In another aspect, the first small RNA sequence comprises a sequence having at least 80%, or at least 85%, or at least 90%, or at least 95% percent identity with a cMyc small RNA sequence comprising SEQ ID NOs: 10, 11, 12, 13, or 14. In embodiments, the first small RNA sequence is selected from SEQ ID NOs: 10, 11, 12, 13, or 14.

In another aspect, the at least one additional small RNA sequence comprises a sequence having at least 80%, or at least 85%, or at least 90%, or at least 95% percent identity with a FDPS small RNA sequence comprising SEQ ID NOs: 1, 2, 3, or 4 or a CD47 small RNA sequence comprising SEQ ID NOs: 5, 6, 7, 8, or 9. In embodiments, the at least one additional small RNA is selected from SEQ ID NOs: 1, 2, 3, 4, 5, 6, 7, 8 or 9.

In another aspect, the third small RNA sequence comprises a sequence having at least 80%, or at least 85%, or at least 90%, or at least 95% percent identity with a FDPS small RNA sequence comprising SEQ ID NOs: 1, 2, 3, or 4 or a CD47 small RNA sequence comprising SEQ ID NOs: 5, 6, 7, 8, or 9. In embodiments, the third small RNA sequence is selected from SEQ ID NOs: 1, 2, 3, 4, 5, 6, 7, 8 or 9.

In another aspect, the viral vector is a lentiviral vector. In another aspect, a lentiviral particle capable of infecting a target cell is disclosed. The lentiviral particle includes an envelope protein optimized for infecting the target cell, and the viral vector as described herein. In embodiments, the target cell is a tumor cell.

In another aspect, a composition is disclosed comprising the lentiviral particle as described herein, and an aminobisphosphonate drug. In embodiments, the aminobisphosphonate drug is zoledronic acid.

In another aspect, a method of treating cancer in a subject is disclosed. The method comprises administering to the subject a therapeutically effective amount of the composition as detailed herein.

In another aspect, a method of treating cancer in a subject is disclosed. The method comprises administering to the subject a therapeutically effective amount of the lentiviral particle as detailed herein, and a therapeutically effective amount of an aminobisphosphonate drug. In another aspect, a method of preventing cancer in a subject is disclosed. The method comprises administering to the subject a therapeutically effective amount of the lentiviral particle as detailed herein, and a therapeutically effective amount of an aminobisphosphonate drug. In embodiments, the foregoing steps are carried out simultaneously. In embodiments, a defined period of time elapses between the foregoing steps. In embodiments, the aminobisphosphonate drug is zoledronic acid. In embodiments, the therapeutically effective amount of the lentiviral particle comprises a plurality of single doses of the lentiviral particle. In embodiments, the therapeutically effective amount of the aminobisphosphonate drug comprises a single dose of the aminobisphosphonate drug.

Other aspects and advantages of the inventions described herein will become apparent from the following detailed description, taken in conjunction with the accompanying drawings, which illustrate by way of example the aspects of the inventions.

BRIEF DESCRIPTION OF THE DRAWINGS

(FIG. 3A) a linear map of a lentiviral vector encoding a FDPS shRNA targeting sequence; (FIG. 3B) a linear map of a lentiviral vector encoding a synthetic microRNA (miRNA) with a FDPS targeting sequence; and (FIG. 3C) a linear map of a lentiviral combination vector that encodes a synthetic microRNA (miRNA) with target sequences directed to cMyc, FDPS, and CD47 expression.

(FIG. 4A) relative expression levels of human FDPS mRNA in response to various shRNA constructs, as described herein; and (FIG. 4B) that lentiviral-delivered miR-based RNA interference inhibits FDPS expression.

(FIG. 7A) relative expression levels of human CD47 mRNA in response to various shRNA constructs, as described herein; (FIG. 7B) that lentiviral-delivered miR-based RNA interference inhibits CD47 expression.

(FIG. 8A) the relative expression levels of human cMyc in response to various shRNA constructs, as described herein and (FIG. 8B) that lentiviral-delivered miR-based RNA interference inhibits cMyc expression.

(FIG. 10A) depicts photographic data at day 8; (FIG. 10B) depicts photon intensity data at day 8; (FIG. 10C) depicts photographic data at day 22; and (FIG. 10D) depicts photon intensity data at day 22.

DETAILED DESCRIPTION

Overview of the Disclosure

Figure 1:
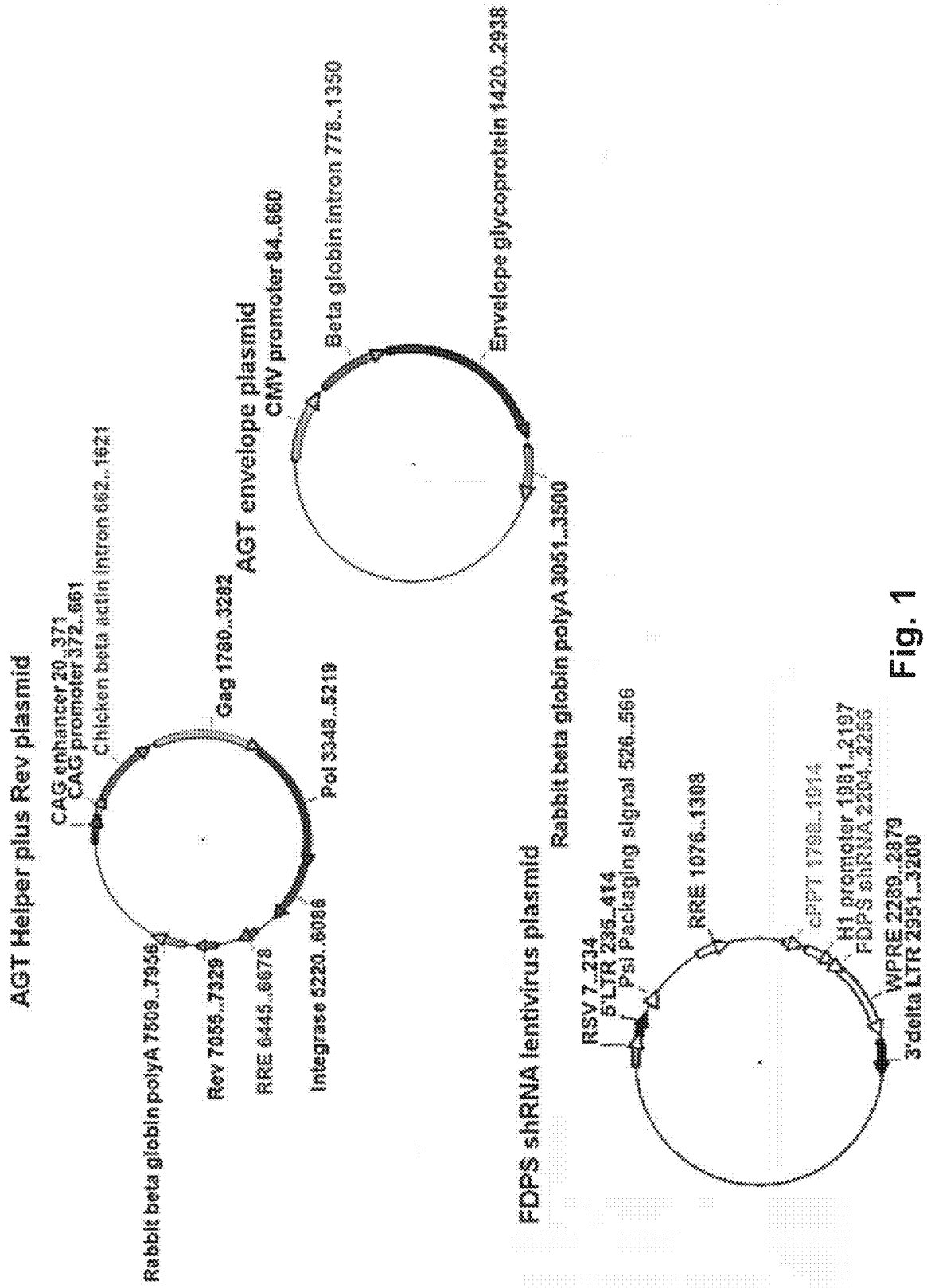
FIG. 1 depicts an exemplary 3-vector lentiviral system in a circularized form.

The present disclosure relates to therapeutic vectors and delivery of the same to cells. In embodiments, the therapeutic vectors target more than one mRNA target. In embodiments, the therapeutic vectors are provided with small RNAs, including short homology RNAs (shRNAs) or microRNAs (miRNAs) that target FDPS, thereby reducing expression levels of this enzyme. The therapeutic vectors include lentiviral vectors. The present disclosure demonstrates that targeting FDPS, in conjunction with treatment with an aminobisphosphonate drug, can effectively treat cancer.

Definitions and Interpretation

Unless otherwise defined herein, scientific and technical terms used in connection with the present disclosure shall have the meanings that are commonly understood by those of ordinary skill in the art. Further, unless otherwise required by context, singular terms shall include pluralities and plural terms shall include the singular. Generally, nomenclature used in connection with, and techniques of, cell and tissue culture, molecular biology, immunology, microbiology, genetics and protein and nucleic acid chemistry and hybridization described herein are those well-known and commonly used in the art. The methods and techniques of the present disclosure are generally performed according to conventional methods well-known in the art and as described in various general and more specific references that are cited and discussed throughout the present specification unless otherwise indicated. See, e.g.: Sambrook J. & Russell D. Molecular Cloning: A Laboratory Manual, 3rd ed., Cold Spring Harbor Laboratory Press, Cold Spring Harbor, N.Y. (2000); Ausubel et al., Short Protocols in Molecular Biology: A Compendium of Methods from Current Protocols in Molecular Biology, Wiley, John & Sons, Inc. (2002); Harlow and Lane Using Antibodies: A Laboratory Manual; Cold Spring Harbor Laboratory Press, Cold Spring Harbor, N.Y. (1998); and Coligan et al., Short Protocols in Protein Science, Wiley, John & Sons, Inc. (2003). Any enzymatic reactions or purification techniques are performed according to manufacturer's specifications, as commonly accomplished in the art or as described herein. The nomenclature used in connection with, and the laboratory procedures and techniques of, analytical chemistry, synthetic organic chemistry, and medicinal and pharmaceutical chemistry described herein are those well-known and commonly used in the art.

As used in the description and the appended claims, the singular forms "a", "an" and "the" are used interchangeably and intended to include the plural forms as well and fall within each meaning, unless the context clearly indicates otherwise. Also, as used herein, "and/or" refers to and encompasses any and all possible combinations of one or more of the listed items, as well as the lack of combinations when interpreted in the alternative ("or").

All numerical designations, e.g., pH, temperature, time, concentration, and molecular weight, including ranges, are approximations which are varied (+) or (−) by increments of 0.1. It is to be understood, although not always explicitly stated that all numerical designations are preceded by the term "about". The term "about" also includes the exact value "X" in addition to minor increments of "X" such as "X+0.1" or "X−0.1." It also is to be understood, although not always explicitly stated, that the reagents described herein are merely exemplary and that equivalents of such are known in the art.

As used herein, the term "about" will be understood by persons of ordinary skill in the art and will vary to some extent depending upon the context in which it is used. If there are uses of the term which are not clear to persons of ordinary skill in the art given the context in which it is used, "about" will mean up to plus or minus 10% of the particular term.

The terms "administration of" or "administering" an active agent should be understood to mean providing an active agent to the subject in need of treatment in a form that can be introduced into that individual's body in a therapeutically useful form and therapeutically effective amount.

As used herein, the term "combination vector" means a therapeutic vector that targets more than one mRNA. For example, a therapeutic vector that contains two shRNAs or two miRNAs directed towards two different mRNAs can be referred to as a "combination vector."

As used herein, the term "comprising" is intended to mean that the compositions and methods include the recited elements, but not excluding others. "Consisting essentially of" when used to define compositions and methods, shall mean excluding other elements of any essential significance to the composition or method. "Consisting of" shall mean excluding more than trace elements of other ingredients for claimed compositions and substantial method steps. Embodiments defined by each of these transition terms are within the scope of this disclosure. Accordingly, it is intended that the methods and compositions can include additional steps and components (comprising) or alternatively including steps and compositions of no significance (consisting essentially of) or alternatively, intending only the stated method steps or compositions (consisting of).

As used herein, "expression," "expressed," or "encodes" refers to the process by which polynucleotides are transcribed into mRNA and/or the process by which the transcribed mRNA is subsequently being translated into peptides, polypeptides, or proteins. Expression may include splicing of the mRNA in a eukaryotic cell or other forms of post-transcriptional modification or post-translational modification.

The term "farnesyl diphosphate synthase" may also be referred to herein as FDPS, and may also be referred to herein as farnesyl pyrophosphate synthase or FPPS.

The term "gamma delta T cell" may also be referred to herein as a γδ T cell, or further as a GD T cell. The term "gamma delta T cell activation" refers to any measurable biological phenomenon associated with a gamma delta T cell that is representative of such T cell being activated. Non-limiting examples of such a biological phenomenon include an increase of cytokine production, changes in the qualitative or quantitative composition of cell surface proteins, an increase in T cell proliferation, and/or an increase in T cell effector function, such killing or a target cell or assisting another effector cell to kill a target cell. A target cell may be a cancer cell.

The terms "individual," "subject," and "patient" are used interchangeably herein, and refer to any individual mammal subject, e.g., bovine, canine, feline, equine, or human.

The term "LV" refers generally to "lentivirus." As an example, reference to "LV-shFDPS" is reference to a lentivirus that expresses an shRNA that targets FDPS.

The term "miRNA" refers to a microRNA, and also may be referred to herein as "miR".

The term "packaging cell line" refers to any cell line that can be used to express a lentiviral particle.

The term "percent identity," in the context of two or more nucleic acid or polypeptide sequences, refer to two or more sequences or subsequences that have a specified percentage of nucleotides or amino acid residues that are the same, when compared and aligned for maximum correspondence, as measured using one of the sequence comparison algorithms described below (e.g., BLASTP and BLASTN or other algorithms available to persons of skill) or by visual inspection. Depending on the application, the "percent identity" can exist over a region of the sequence being compared, e.g., over a functional domain, or, alternatively, exist over the full length of the two sequences to be compared. For sequence comparison, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., infra).

One example of an algorithm that is suitable for determining percent sequence identity and sequence similarity is the BLAST algorithm, which is described in Altschul et al., J. Mol. Biol. 215:403-410 (1990). Software for performing BLAST analyses is publicly available through the National Center for Biotechnology Information website.

The percent identity between two nucleotide sequences can be determined using the GAP program in the GCG software package (available at www.gcg.com), using a NWSgapdna.CMP matrix and a gap weight of 40, 50, 60, 70, or 80 and a length weight of 1, 2, 3, 4, 5, or 6. The percent identity between two nucleotide or amino acid sequences can also be determined using the algorithm of E. Meyers and W. Miller (CABIOS, 4:11-17 (1989)) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (J. Mol. Biol. (48):444-453 (1970)) algorithm which has been incorporated into the GAP program in the GCG software package (available at www.gcg.com), using either a Blossum 62 matrix or a PAM250 matrix, and a gap weight of 16, 14, 12, 10, 8, 6, or 4 and a length weight of 1, 2, 3, 4, 5, or 6.

The nucleic acid and protein sequences of the present disclosure can further be used as a "query sequence" to perform a search against public databases to, for example, identify related sequences. Such searches can be performed using the NBLAST and XBLAST programs (version 2.0) of Altschul, et al. (1990) J. Mol. Biol. 215:403-10. BLAST nucleotide searches can be performed with the NBLAST program, score=100, word length=12 to obtain nucleotide sequences homologous to the nucleic acid molecules provided in the disclosure. BLAST protein searches can be performed with the XBLAST program, score=50, word length=3 to obtain amino acid sequences homologous to the protein molecules of the disclosure. To obtain gapped alignments for comparison purposes, Gapped BLAST can be utilized as described in Altschul et al., (1997) Nucleic Acids Res. 25(17):3389-3402. When utilizing BLAST and Gapped BLAST programs, the default parameters of the respective programs (e.g., XBLAST and NBLAST) can be used. See www.ncbi.nlm.nih.gov.

As used herein, "pharmaceutically acceptable" refers to those compounds, materials, compositions, and/or dosage forms which are, within the scope of sound medical judgment, suitable for use in contact with the tissues, organs, and/or bodily fluids of human beings and animals without excessive toxicity, irritation, allergic response, or other problems or complications commensurate with a reasonable benefit/risk ratio.

As used herein, a "pharmaceutically acceptable carrier" refers to, and includes, any and all solvents, dispersion media, coatings, antibacterial and antifungal agents, isotonic and absorption delaying agents, and the like that are physiologically compatible. The compositions can include a pharmaceutically acceptable salt, e.g., an acid addition salt or a base addition salt (see, e.g., Berge et al. (1977) J Pharm Sci 66:1-19).

As used herein, the term "SEQ ID NO" is synonymous with the term "Sequence ID No."

As used herein, "small RNA" refers to non-coding RNA that are generally about 200 nucleotides or less in length and possess a silencing or interference function. In other embodiments, the small RNA is about 175 nucleotides or less, about 150 nucleotides or less, about 125 nucleotides or less, about 100 nucleotides or less, or about 75 nucleotides or less in length. Such RNAs include microRNA (miRNA), small interfering RNA (siRNA), double stranded RNA (dsRNA), and short hairpin RNA (shRNA). "Small RNA" of the disclosure should be capable of inhibiting or knocking-down gene expression of a target gene, generally through pathways that result in the destruction of the target gene mRNA.

The term "therapeutically effective amount" refers to a sufficient quantity of the active agents of the present disclosure, in a suitable composition, and in a suitable dosage form to treat or prevent the symptoms, progression, or onset of the complications seen in patients suffering from a given ailment, injury, disease, or condition. The therapeutically effective amount will vary depending on the state of the patient's condition or its severity, and the age, weight, etc., of the subject to be treated. A therapeutically effective amount can vary, depending on any of a number of factors, including, e.g., the route of administration, the condition of the subject, as well as other factors understood by those in the art.

As used herein, the term "therapeutic vector" includes, without limitation, reference to a lentiviral vector or an adeno-associated viral (AAV) vector. Additionally, as used herein with reference to the lentiviral vector system, the term "vector" is synonymous with the term "plasmid." For example, the 3-vector and 4-vector systems, which include the 2-vector and 3-vector packaging systems, can also be referred to as 3-plasmid and 4-plasmid systems.

"A treatment" is intended to target the disease state and combat it, i.e., ameliorate or prevent the disease state. The particular treatment thus will depend on the disease state to be targeted and the current or future state of medicinal therapies and therapeutic approaches. A treatment may have associated toxicities.

The term "treatment" or "treating" generally refers to an intervention in an attempt to alter the natural course of the subject being treated, and can be performed either for prophylaxis or during the course of clinical pathology. Desirable effects include, but are not limited to, preventing occurrence or recurrence of disease, alleviating symptoms, suppressing, diminishing or inhibiting any direct or indirect pathological consequences of the disease, ameliorating or palliating the disease state, and causing remission or improved prognosis.

Description of Aspects and Embodiments of the Disclosure

In an aspect of the disclosure, a viral vector comprising a therapeutic cargo portion is disclosed. The therapeutic cargo portion includes at least one small RNA sequence that is capable of binding to at least one pre-determined complementary mRNA sequence, wherein the at least one complementary mRNA sequence comprises a FDPS mRNA sequence. In embodiments, the therapeutic cargo portion may further include a second small RNA sequence that is capable of binding to a second pre-determined complementary mRNA sequence, wherein the second pre-determined complementary mRNA sequence comprises a CD47 mRNA sequence or a cMyc mRNA sequence. In embodiments, the therapeutic cargo portion may further include a third small RNA sequence that is capable of binding to a third pre-determined complementary mRNA sequence, wherein the third pre-determined complementary mRNA sequence comprises a CD47 mRNA sequence or a cMyc mRNA sequence. The small RNA sequence may be a microRNA (miRNA) or a short hairpin RNA (shRNA).

In another aspect, the small RNA sequence comprises a sequence having at least 80%, or at least 81%, or at least 82%, or at least 83%, or at least 84%, or at least 85%, or at least 86%, or at least 87%, or at least 88%, or at least 89%, or at least 90%, or at least 91%, or at least 92%, or at least 93%, or at least 94%, or at least 95% or greater percent identity with a FDPS small RNA sequence comprising SEQ ID NOs: 1, 2, 3, or 4. In embodiments, the small RNA sequence is selected from SEQ ID NOs: 1, 2, 3, or 4.

In another aspect, the second small RNA sequence comprises a sequence having at least 80%, or at least 81%, or at least 82%, or at least 83%, or at least 84%, or at least 85%, or at least 86%, or at least 87%, or at least 88%, or at least 89%, or at least 90%, or at least 91%, or at least 92%, or at least 93%, or at least 94%, or at least 95% or greater identity with a CD47 small RNA sequence comprising SEQ ID NOs: 5, 6, 7, 8 or 9 or a cMyc small RNA sequence comprising SEQ ID NOs: 10, 11, 12, 13, or 14. In embodiments, the second small RNA sequence is selected from SEQ ID NOs: 5, 6, 7, 8, 9, 10, 11, 12, 13, or 14.

In another aspect, the third small RNA sequence comprises a sequence having at least 80%, or at least 81%, or at least 82%, or at least 83%, or at least 84%, or at least 85%, or at least 86%, or at least 87%, or at least 88%, or at least 89%, or at least 90%, or at least 91%, or at least 92%, or at least 93%, or at least 94%, or at least 95% or greater identity with a CD47 small RNA sequence comprising SEQ ID NOs: 5, 6, 7, 8 or 9 or a cMyc small RNA sequence comprising SEQ ID NOs: 10, 11, 12, 13, or 14. In embodiments, the third small RNA sequence is selected from SEQ ID NOs: 5, 6, 7, 8, 9, 10, 11, 12, 13, or 14.

In another aspect, a viral vector comprising a therapeutic cargo portion is disclosed. The therapeutic cargo portion includes at least one small RNA sequence that is capable of binding to at least one pre-determined complementary mRNA sequence, wherein the at least one complementary mRNA sequence comprises a CD47 mRNA sequence. In embodiments, the therapeutic cargo portion further comprises a second small RNA sequence that is capable of binding to a second pre-determined complementary mRNA sequence, wherein the second pre-determined complementary mRNA sequence comprises a FDPS mRNA sequence or a cMyc mRNA sequence. In embodiments, the therapeutic cargo portion further comprises a third small RNA sequence that is capable of binding to a third pre-determined complementary mRNA sequence, wherein the third pre-determined complementary mRNA sequence comprises a FDPS mRNA sequence or a cMyc mRNA sequence. In embodiments, the small RNA sequence is a miRNA or a shRNA.

In another aspect, the small RNA sequence comprises a sequence having at least 80%, or at least 85%, or at least 90%, or at least 95% percent identity with a CD47 small RNA sequence comprising SEQ ID NOs: 5, 6, 7, 8 or 9. In embodiments, the small RNA sequence is selected from SEQ ID NOs: 5, 6, 7, 8 or 9.

In another aspect, the second small RNA sequence comprises a sequence having at least 80%, or at least 85%, or at least 90%, or at least 95% percent identity with a FDPS small RNA sequence comprising SEQ ID NOs: 1, 2, 3, or 4 or a cMyc small RNA sequence comprising SEQ ID NOs: 10, 11, 12, 13, or 14. In embodiments, the second small RNA sequence is selected from SEQ ID NOs: 1, 2, 3, 4, 10, 11, 12, 13, or 14.

In another aspect, the third small RNA comprises a sequence having at least 80%, or at least 81%, or at least 82%, or at least 83%, or at least 84%, or at least 85%, or at least 86%, or at least 87%, or at least 88%, or at least 89%, or at least 90%, or at least 91%, or at least 92%, or at least 93%, or at least 94%, or at least 95% or greater identity with a FDPS small RNA sequence comprising SEQ ID NOs: 1, 2, 3, or 4 or a cMyc small RNA sequence comprising SEQ ID NOs: 10, 11, 12, 13, or 14. In embodiments, the third small RNA sequence is selected from SEQ ID NOs: 1, 2, 3, 4, 10, 11, 12, 13, or 14.

In another aspect, a viral vector comprising a therapeutic cargo portion is disclosed. The therapeutic cargo portion comprises a first small RNA sequence that is capable of binding to a first pre-determined complementary mRNA sequence, and at least one additional small RNA sequence that is capable of binding to a second pre-determined complementary mRNA sequence, wherein the first pre-determined complementary mRNA sequence comprises a cMyc mRNA sequence, and the second pre-determined complementary sequence comprises a FDPS mRNA sequence or a CD47 mRNA sequence.

In another aspect, the therapeutic cargo portion further comprises a third small RNA sequence that is capable of binding to a third pre-determined complementary mRNA sequence, wherein the third pre-determined complementary mRNA sequence comprises a FDPS mRNA sequence or a CD47 mRNA sequence. In embodiments, the small RNA sequences are miRNAs or shRNAs.

In another aspect, the first small RNA sequence comprises a sequence having at least 80%, or at least 81%, or at least 82%, or at least 83%, or at least 84%, or at least 85%, or at least 86%, or at least 87%, or at least 88%, or at least 89%, or at least 90%, or at least 91%, or at least 92%, or at least 93%, or at least 94%, or at least 95% or greater identity with a cMyc small RNA sequence comprising SEQ ID NOs: 10, 11, 12, 13, or 14. In embodiments, the first small RNA sequence is selected from SEQ ID NOs: 10, 11, 12, 13, or 14.

In another aspect, the at least one additional small RNA sequence comprises a sequence having at least 80%, or at least 81%, or at least 82%, or at least 83%, or at least 84%, or at least 85%, or at least 86%, or at least 87%, or at least 88%, or at least 89%, or at least 90%, or at least 91%, or at least 92%, or at least 93%, or at least 94%, or at least 95% or greater percent identity with a FDPS small RNA sequence comprising SEQ ID NOs: 1, 2, 3, or 4 or a CD47 small RNA sequence comprising SEQ ID NOs: 5, 6, 7, 8 or 9. In embodiments, the at least one additional small RNA is selected from SEQ ID NOs: 1, 2, 3, 4, 5, 6, 7, 8, or 9.

In another aspect, the third small RNA sequence comprises a sequence having at least 80%, or at least 81%, or at least 82%, or at least 83%, or at least 84%, or at least 85%, or at least 86%, or at least 87%, or at least 88%, or at least 89%, or at least 90%, or at least 91%, or at least 92%, or at least 93%, or at least 94%, or at least 95% or greater identity with a FDPS small RNA sequence comprising SEQ ID NOs: 1, 2, 3, or 4 or a CD47 small RNA sequence comprising SEQ ID NOs: 5, 6, 7, 8 or 9. In embodiments, the third small RNA sequence is selected from SEQ ID NOs: 1, 2, 3, 4, 5, 6, 7, 8, or 9.

In another aspect, the small RNA sequences referred to herein can comprise a sequence having at least 80%, or at least 81%, or at least 82%, or at least 83%, or at least 84%, or at least 85%, or at least 86%, or at least 87%, or at least 88%, or at least 89%, or at least 90%, or at least 91%, or at least 92%, or at least 93%, or at least 94%, or at least 95% or greater identity with any of the miRNA sequences detailed herein, including: miR30 FDPS sequence #1 (SEQ ID NO: 53), miR30 FDPS sequence #2 (SEQ ID NO: 54). miR30 FDPS sequence #3 (SEQ ID NO: 55), miR155 FDPS sequence #1 (SEQ ID NO: 56), miR21 FDPS sequence #1 (SEQ ID NO: 57), miR185 FDPS sequence #1 (SEQ ID NO: 58), miR155 CD47 sequence #1 (SEQ ID NO: 82; miR155 CD47 target sequence #2 (SEQ ID NO: 66), miR155 CD47 target sequence #3 (SEQ ID NO: 67), miR155 CD47 target sequence #4 (SEQ ID NO: 68), miR21 cMyc sequence (SEQ ID NO: 83); or miR155 cMyc sequence (SEQ ID NO: 70).

In embodiments, the small RNA sequences can comprise any of the miRNA sequences detailed herein, including: miR30 FDPS sequence #1 (SEQ ID NO: 53), miR30 FDPS sequence #2 (SEQ ID NO: 54). miR30 FDPS sequence #3 (SEQ ID NO: 55), miR155 FDPS sequence #1 (SEQ ID NO: 56), miR21 FDPS sequence #1 (SEQ ID NO: 57), miR185 FDPS sequence #1 (SEQ ID NO: 58), miR155 CD47 sequence #1 (SEQ ID NO: 82; miR155 CD47 target sequence #2 (SEQ ID NO: 66), miR155 CD47 target sequence #3 (SEQ ID NO: 67), miR155 CD47 target sequence #4 (SEQ ID NO: 68), miR21 cMyc sequence (SEQ ID NO: 83); or miR155 cMyc sequence (SEQ ID NO: 70).

In another aspect, the viral vector is a lentiviral vector. In another aspect of the disclosure a lentiviral particle capable of infecting a target cell is disclosed. The lentiviral particle includes an envelope protein optimized for infecting the target cell; and the viral vector as described herein. In embodiments, the target cell is a tumor cell.

In another aspect, a composition is disclosed comprising the lentiviral particle as described herein, and an aminobisphosphonate drug. In embodiments, the aminobisphosphonate drug is zoledronic acid.

In another aspect of the disclosure, a method of treating cancer in a subject is disclosed. The method comprises administering to the subject a therapeutically effective amount of the composition as detailed herein.

In another aspect, a method of treating cancer in a subject is disclosed. The method comprises administering to the subject a therapeutically effective amount of the lentiviral particle as detailed herein; and a therapeutically effective amount of an aminobisphosphonate drug. In embodiments, the foregoing steps are carried out simultaneously. In embodiments, a defined period of time elapses between the foregoing steps. In embodiments, the aminobisphosphonate drug is zoledronic acid. In embodiments, the therapeutically effective amount of the lentiviral particle comprises a plurality of single doses of the lentiviral particle. In embodiments, the therapeutically effective amount of the aminobisphosphonate drugs comprises a single dose of the aminobisphosphonate drug.

Additional aspects of the present invention describe the development of multi-gene-targeting vectors for treatment of cancer, and, as a non-limiting example, for the treatment of hepatocellular carcinoma ("HCC"). These vectors address three concerns in respect of HCC therapy. Firstly, the therapeutic vectors may include inhibitory RNA constructs for reducing the expression of cMyc oncogene protein. The cMyc oncogene protein is responsible for tumorigenesis, tumor growth and immune evasion. The therapeutic vector may include more than just one inhibitory RNA construct for reducing cMyc expression. For example, in embodiments, combination vectors are specifically contemplated when cMyc is a target of the vector. Secondly, vectors have been developed (e.g., through inhibitory RNA constructs) to reduce the expression of farnesyl diphosphate synthase ("FDPS"). By reducing the levels of FDPS, tumor cells are modified, for example, to become stimulatory for gamma delta T cells. These gamma delta T cells are capable of cytotoxic killing of tumor cells. Thirdly, the vectors have been developed to reduce the expression (e.g., through inhibitory RNA constructs) of at least one other gene product. In certain embodiments, the at least one other gene product can be an immune checkpoint regulator. Examples of immune checkpoint regulators include, but are not limited to programmed death-ligand 1 (PD-L1), galactosidase-binding soluble lectin 9 (LGALS9A), tumor necrosis factor receptor super family, member 14 (HVEM), V-set domain containing T cell activation inhibitor 1 (B7-H4), CD276 molecule (B7-H3), CD80 molecule (CD28LG1), and CD86 molecule (CD28LG2). In embodiments, the immune checkpoint regulator is PD-L1. By reducing expression cMyc, levels of PD-L1 are consequently decreased because cMyc is a positive regulator for expression of PD-L1 and other immune evasion genes including CD47, which are expressed in tumor cells. By decreasing the levels of CD47, tumor cell phagocytosis is increased leading to improved T cell responses through cross-presentation of tumor antigens on antigen-presenting cells. By decreasing PD-L1 and potentially other immune checkpoint inhibitory molecules, the efficiency of immune stimulation of T cells, including stimulation of gamma delta T cells, can be improved. While cMyc regulates PD-L1 levels, PD-L1 or other immune checkpoint regulators can be targeted directly using the therapeutic vectors described herein by generating shRNAs or miRNAs that are specifically directed to PD-L1 or the other selected immune checkpoint regulators.

In certain embodiments, the at least one other gene product can be a gene product that influences phagocytosis. For example, the at least one other gene product that influences phagocytosis can be CD47. By reducing the expression of CD47 the block to macrophage phagocytosis of tumor cells is removed. These two mechanisms combine to increase the efficiency and activity of acquired or innate immunity needed to treat or eliminate HCC.

The combination vectors disclosed herein are optimized such that the correct promoter has been selected to best match RNA processing system requirements. Additionally, the therapeutic cargo portion has been designed such that the miRNA or miRNAs are in a cluster so that processing of the first miRNA facilitates processing of the second miRNA and so on. The order of the miRNAs may be important to improve processing fidelity and associated rates so as to ensure that processing is not so rapid that genomic RNA for packaging into lentivirus particles is processed thus decreasing the efficiency of lentivirus manufacturing. Additionally, the combination vectors can be designed such that the therapeutic cargo portion includes multiple shRNAs under the control of discrete promoters.

Cancer

The compositions and methods provided herein are used to treat cancer. A cell, tissue, or target may be a cancer cell, a cancerous tissue, harbor cancerous tissue, or be a subject or patient diagnosed or at risk of developing a disease or condition. In certain aspects, a cell may be an epithelial, an endothelial, a mesothelial, a glial, a stromal, or a mucosal cell. The cancer cell population can include, but is not limited to a brain, a neuronal, a blood, an endometrial, a meninges, an esophageal, a lung, a cardiovascular, a liver, a lymphoid, a breast, a bone, a connective tissue, a fat, a retinal, a thyroid, a glandular, an adrenal, a pancreatic, a stomach, an intestinal, a kidney, a bladder, a colon, a prostate, a uterine, an ovarian, a cervical, a testicular, a splenic, a skin, a smooth muscle, a cardiac muscle, or a striated muscle cell. In still a further aspect cancer includes, but is not limited to astrocytoma, acute myeloid leukemia, anaplastic large cell lymphoma, acute lymphoblastic leukemia, angiosarcoma, B-cell lymphoma, Burkitt's lymphoma, breast carcinoma, bladder carcinoma, carcinoma of the head and neck, cervical carcinoma, chronic lymphoblastic leukemia, chronic myeloid leukemia, colorectal carcinoma, endometrial carcinoma, esophageal squamous cell carcinoma, Ewing's sarcoma, fibrosarcoma, glioma, glioblastoma, gastrinoma, gastric carcinoma, hepatoblastoma, hepatocellular carcinoma, Kaposi's sarcoma, Hodgkin lymphoma, laryngeal squamous cell carcinoma, larynx carcinoma, leukemia, leiomyosarcoma, lipoma, liposarcoma, melanoma, mantle cell lymphoma, medulloblastoma, mesothelioma, myxofibrosarcoma, myeloid leukemia, mucosa-associated lymphoid tissue B cell lymphoma, multiple myeloma, high-risk myelodysplastic syndrome, nasopharyngeal carcinoma, neuroblastoma, neurofibroma, high-grade non-Hodgkin lymphoma, non-Hodgkin lymphoma, lung carcinoma, non-small cell lung carcinoma, ovarian carcinoma, oesophageal carcinoma, osteosarcoma, pancreatic carcinoma, pheochromocytoma, prostate carcinoma, renal cell carcinoma, retinoblastoma, rhabdomyosarcoma, salivary gland tumor, Schwanomma, small cell lung cancer, squamous cell carcinoma of the head and neck, testicular tumor, thyroid carcinoma, urothelial carcinoma, and Wilm's tumor.

The compositions and methods provided herein are also used to treat NSCLC (non-small cell lung cancer), pediatric malignancies, cervical and other tumors caused or promoted by human papilloma virus (HPV), melanoma, Barrett's esophagus (pre-malignant syndrome), adrenal and skin cancers and auto immune, neoplastic cutaneous diseases.

Therapeutic Vectors

The therapeutic vectors can be delivered via known transfection and/or transduction vectors, including but not limited to lentiviral vectors, adeno-associated virus, poxvirus, herpesvirus vectors, protein and/or lipid complexes, liposomes, micelles, and the like.

Viral vectors can be preferentially targeted to cell types that are useful for the disclosed methods (i.e., tumor cells or myeloid cells). Viral vectors can be used to transduce genes into target cells owing to specific virus envelope-host cell receptor interactions and viral mechanisms for gene expression. As a result, viral vectors have been used as vehicles for the transfer of genes into many different cell types including whole embryos, fertilized eggs, isolated tissue samples, tissue targets in situ, and cultured cell lines. The ability to introduce and express foreign genes in a cell is useful for the study of gene expression, and the elucidation of cell lineages as well as providing the potential for therapeutic interventions such as gene therapy, somatic cell reprogramming of induced pluripotent stem cells, and various types of immunotherapy. Viral components from viruses like Papovaviridae (e.g. bovine papillomavirus or BPV) or Herpesviridae (e.g. Epstein Barr Virus or EBV) or Hepadnaviridae (e.g. Hepatitis B Virus or HBV) or pox vectors including vaccinia may be used in the disclosed vectors.

Lentiviral vectors are a preferred type of vector for the disclosed compositions and methods, although the disclosure is not specifically limited to lentiviral vectors. Lentivirus is a genus of viruses that can deliver a significant amount of viral nucleic acid into a host cell. Lentiviruses are characterized as having a unique ability to infect/transduce non-dividing cells, and following transduction, lentiviruses integrate their nucleic acid into the host cell's chromosomes.

Infectious lentiviruses have three main genes coding for the virulence proteins gag, pol, and env, and two regulatory genes including tat and rev. Depending on the specific serotype and virus, there may be additional accessory genes that code for proteins involved in regulation, synthesis, and/or processing viral nucleic acids and other replicative functions.

Moreover, lentiviruses contain long terminal repeat (LTR) regions, which may be approximately 600 nt long. LTRs may be segmented into U3, R, and U5 regions. LTRs can mediate integration of retroviral DNA into the host chromosome via the action of integrase. Alternatively, without functioning integrase, the LTRs may be used to circularize the viral nucleic acid.

Viral proteins involved in early stages of lentivirus replication include reverse transcriptase and integrase. Reverse transcriptase is the virally encoded, RNA-dependent DNA polymerase. The enzyme uses a viral RNA genome as a template for the synthesis of a complementary DNA copy. Reverse transcriptase also has RNaseH activity for destruction of the RNA-template. Integrase binds both the viral cDNA generated by reverse transcriptase and the host DNA. Integrase processes the LTR before inserting the viral genome into the host DNA. Tat acts as a trans-activator during transcription to enhance initiation and elongation. The rev responsive element acts post-transcriptionally, regulating mRNA splicing and transport to the cytoplasm.

Viral vectors, in general, comprise glycoproteins and the various glycoproteins may provide specific affinities. For instance, VSVG peptides can increase transfection into myeloid cells. Alternatively, viral vectors can also have targeting moieties, such as antibodies, attached to their shell peptides. Targeting antibodies can be specific for antigens that are overexpressed on a tumor, for instance, like HER-2, PSA, CEA, M2-PK, and CA19-9. Other viral vector specificities are also known in the art and can be used to target particular populations of cells. For example, poxvirus vectors target to macrophages and dendritic cells.

With respect to the therapeutic vectors detailed herein, in aspects of the present disclosure, a miRNA or shRNA is under the control of a single promoter. In embodiments, when multiple miRNAs are present in the same therapeutic vector, the miRNAs are under the control of a single promoter, for example a Pol II promoter. In embodiments, the Pol II promoter is EF1-alpha or a CMV promoter.

In embodiments, when multiple shRNAs are present in the same therapeutic vector, the shRNAs are under the control of multiple promoters. For example, a first shRNA is under the control of a first promoter, a second shRNA is under the control of a second promoter, a third shRNA is under the control of a third promoter, and so on. In non-limiting embodiments, the promoters can be selected from H1 (SEQ ID NO: 15), U6 (SEQ ID NO: 16), or 7SK (SEQ ID NO: 17).

Figure 3A:
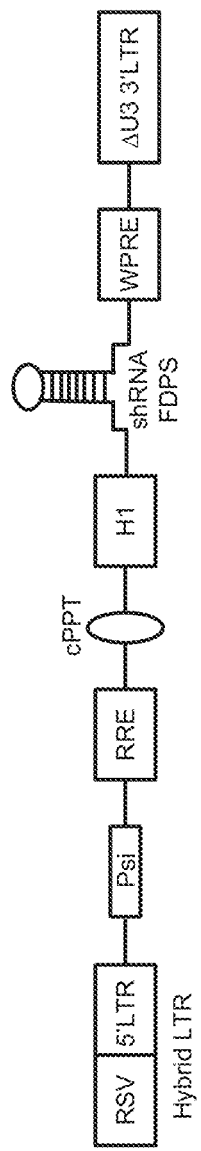
FIGS. 3A-3C depict.
Figure 3B:
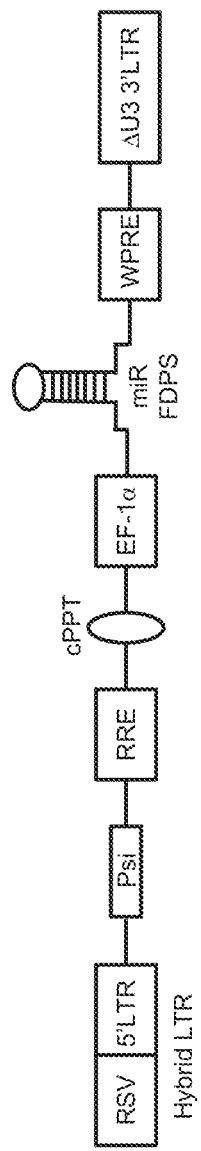
Figure 3C:
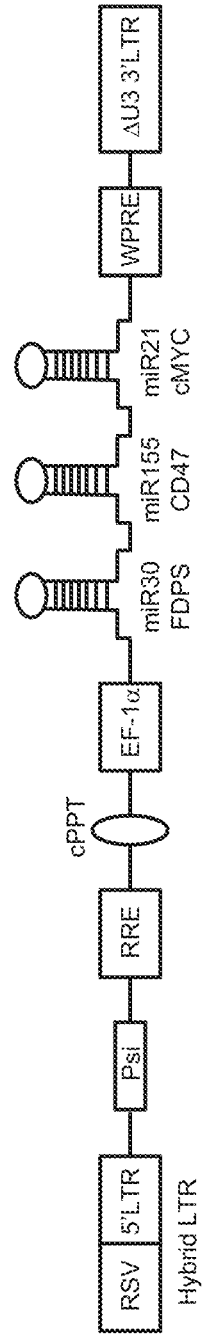

As depicted in FIG. 3C, a non-limiting example of a therapeutic vector includes a therapeutic cargo of three miRNA targeting cMyc, FDPS, and CD47 mRNA. As shown in Table 1 herein, alternate combinations of one to three miRNA sequences can be used in the final form of the therapeutic vector such that the therapeutic vector is a combination vector. While combinations of one to three miRNA sequences can be used in the final therapeutic vector, it is specifically contemplated that up to four, up to five, or up to six, or up to seven, or up to eight or more miRNA sequences could be used in the final therapeutic vector. Further the miRNA sequences may be sequential or randomly arranged (i.e., the first miRNA need not precede the second miRNA etc.). In addition to the combinations selected, all possible orders of miRNA from 5' to 3' end of the sense strand may be utilized for these lentiviral vectors. Vector components are not repeated for each miRNA combination. In developing the vectors containing miRNAs, shRNAs for the genes of interest are first used to prove that the gene of interest will work in the lentivirus construct; thereafter, and once shRNAs are proven to work (as described below), they are assembled into miRNA clusters as shown, for example, in FIG. 3C herein. The miRNAs preserve targeting sequences but have changes in their overall structure to become better suited for the miRNA processing pathway.

TABLE 1

Combinations of miRNA sequences

| | | | |
|---|---|---|---|
| Vector 1 | | miR155FDPS | |
| Vector 2 | | | miR21CD47 |
| Vector 3 | miR30cMyc | | |
| Vector 4 | miR30cMyc | miR155FDPS | |
| Vector 5 | miR30cMyc | | miR21CD47 |
| Vector 6 | | miR155FDPS | miR21CD47 |
| Vector 7 | miR30cMyc | | miR21CD47 |
| Vector 8 | miR30cMyc | miR155FDPS | miR21CD47 |

Combination vectors can also be generated using shRNAs. However, in these circumstances discrete promoters need to be utilized for each target sequence, as is described herein.

Lentiviral Vector System

A lentiviral virion (particle) is expressed by a vector system encoding the necessary viral proteins to produce a virion (viral particle). There is at least one vector containing a nucleic acid sequence encoding the lentiviral pol proteins necessary for reverse transcription and integration, operably linked to a promoter. In another embodiment, the pol proteins are expressed by multiple vectors. There is also a vector containing a nucleic acid sequence encoding the lentiviral gag proteins necessary for forming a viral capsid operably linked to a promoter. In an embodiment, this gag nucleic acid sequence is on a separate vector than at least some of the pol nucleic acid sequence. In another embodiment, the gag nucleic acid is on a separate vector from all the pol nucleic acid sequences that encode pol proteins.

Numerous modifications can be made to the vectors, which are used to create the particles to further minimize the chance of obtaining wild type revertants. These include, but are not limited to deletions of the U3 region of the LTR, tat deletions and matrix (MA) deletions.

The gag, pol and env vector(s) do not contain nucleotides from the lentiviral genome that package lentiviral RNA, referred to as the lentiviral packaging sequence.

The vector(s) forming the particle preferably do not contain a nucleic acid sequence from the lentiviral genome that expresses an envelope protein. Preferably, a separate vector that contains a nucleic acid sequence encoding an envelope protein operably linked to a promoter is used. This env vector also does not contain a lentiviral packaging sequence. In one embodiment the env nucleic acid sequence encodes a lentiviral envelope protein.

In another embodiment the envelope protein is not from the lentivirus, but from a different virus. The resultant particle is referred to as a pseudotyped particle. By appropriate selection of envelopes one can "infect" virtually any cell. For example, one can use an env gene that encodes an envelope protein that targets an endocytic compartment such as that of the influenza virus, VSV-G, alpha viruses (Semliki forest virus, Sindbis virus), arenaviruses (lymphocytic choriomeningitis virus), flaviviruses (tick-borne encephalitis virus, Dengue virus, hepatitis C virus, GB virus), rhabdoviruses (vesicular stomatitis virus, rabies virus), paramyxoviruses (mumps or measles) and orthomyxoviruses (influenza virus). Other envelopes that can preferably be used include those from Moloney Leukemia Virus such as MLV-E, MLV-A and GALV. These latter envelopes are particularly preferred where the host cell is a primary cell. Other envelope proteins can be selected depending upon the desired host cell. For example, targeting specific receptors such as a dopamine receptor can be used for brain delivery. Another target can be vascular endothelium. These cells can be targeted using a filovirus envelope. For example, the GP of Ebola, which by post-transcriptional modification become the GP, and GP2 glycoproteins. In another embodiment, one can use different lentiviral capsids with a pseudotyped envelope (for example, FIV or SHIV [U.S. Pat. No. 5,654, 195]). A SHIV pseudotyped vector can readily be used in animal models such as monkeys.

As detailed herein, a lentiviral vector system typically includes at least one helper plasmid comprising at least one of a gag, pol, or rev gene. Each of the gag, pol and rev genes may be provided on individual plasmids, or one or more genes may be provided together on the same plasmid. In one embodiment, the gag, pol, and rev genes are provided on the same plasmid (e.g., FIG. 1). In another embodiment, the gag and pol genes are provided on a first plasmid and the rev gene is provided on a second plasmid (e.g., FIG. 2). Accordingly, both 3-vector and 4-vector systems can be used to produce a lentivirus as described in the Examples section and elsewhere herein. The therapeutic vector, the envelope plasmid and at least one helper plasmid are transfected into a packaging cell line. A non-limiting example of a packaging cell line is the 293T/17 HEK cell line. When the therapeutic vector, the envelope plasmid, and at least one helper plasmid are transfected into the packaging cell line, a lentiviral particle is ultimately produced.

In another aspect, a lentiviral vector system for expressing a lentiviral particle is disclosed. The system includes a lentiviral vector as described herein; an envelope plasmid for expressing an envelope protein optimized for infecting a cell; and at least one helper plasmid for expressing gag, pol, and rev genes, wherein when the lentiviral vector, the envelope plasmid, and the at least one helper plasmid are transfected into a packaging cell line, a lentiviral particle is produced by the packaging cell line, wherein the lentiviral particle is capable of inhibiting the genes targeted by the shRNAs or miRNAs..

In another aspect, the therapeutic vector, can include the following elements: hybrid 5' long terminal repeat (RSV/5' LTR) (SEQ ID NOS: 74-75), Psi sequence (RNA packaging site) (SEQ ID NO: 76), RRE (Rev-response element) (SEQ ID NO: 77), cPPT (polypurine tract) (SEQ ID NO: 78), H1 promoter (SEQ ID NO: 15), FDPS shRNA (e.g., SEQ ID NOS: 1, 2, 3, 4 or variants thereof), Woodchuck Post-Transcriptional Regulatory Element (WPRE) (SEQ ID NO: 79), and 3' Delta LTR (SEQ ID NO: 80). In another aspect, sequence variation, by way of substitution, deletion, addition, or mutation can be used to modify the sequences references herein.

In another aspect, and as detailed herein, a helper plasmid has been designed to include the following elements: CAG promoter (SEQ ID NO: 19); HIV component gag (SEQ ID NO: 21); HIV component pol (SEQ ID NO: 22); HIV Int (SEQ ID NO: 23); HIV RRE (SEQ ID NO: 24); and HIV Rev (SEQ ID NO: 25). In another aspect, the helper plasmid may be modified to include a first helper plasmid for expressing the gag and pol genes, and a second and separate plasmid for expressing the rev gene. In another aspect, sequence variation, by way of substitution, deletion, addition, or mutation can be used to modify the sequences references herein.

In another aspect, and as detailed herein, an envelope plasmid has been designed to include the following elements being from left to right: RNA polymerase II promoter (CMV) (SEQ ID NO: 27) and vesicular stomatitis virus G glycoprotein (VSV-G) (SEQ ID NO: 29). In another aspect, sequence variation, by way of substitution, deletion, addition, or mutation can be used to modify the sequences references herein.

In another aspect, the plasmids used for lentiviral packaging can be modified with similar elements and the intron sequences could potentially be removed without loss of vector function. For example, the following elements can replace similar elements in the plasmids that comprise the packaging system: Elongation Factor-1 (EF-1), phosphoglycerate kinase (PGK), and ubiquitin C (UbC) promoters can replace the CMV or CAG promoter. SV40 poly A and bGH poly A can replace the rabbit beta globin poly A. The HIV sequences in the helper plasmid can be constructed from different HIV strains or clades. The VSV-G glycoprotein can be substituted with membrane glycoproteins from feline endogenous virus (RD114), gibbon ape leukemia virus (GALV), Rabies (FUG), lymphocytic choriomeningitis virus (LCMV), influenza A fowl plague virus (FPV), Ross River alphavirus (RRV), murine leukemia virus 10A1 (MLV), or Ebola virus (EboV).

Of note, lentiviral packaging systems can be acquired commercially (e.g., Lenti-vpak packaging kit from OriGene Technologies, Inc., Rockville, Md.), and can also be designed as described herein. Moreover, it is within the skill of a person skilled in the art to substitute or modify aspects of a lentiviral packaging system to improve any number of relevant factors, including the production efficiency of a lentiviral particle.

Doses and Dosage Forms

The disclosed vector compositions allow for short, medium, or long-term expression of genes or sequences of interest and episomal maintenance of the disclosed vectors. Accordingly, dosing regimens may vary based upon the condition being treated and the method of administration.

In embodiments, vector compositions may be administered to a subject in need in varying doses. Specifically, a subject may be administered about $>10^6$ infectious doses (where 1 dose is needed on average to transduce 1 target cell). More specifically, a subject may be administered about $10^7$, about $>10^8$, about $>10^9$, or about $>10^{10}$ infectious doses, or any number of doses in-between these values. Upper limits of dosing will be determined for each disease indication, including a specific cancer type, and will depend on toxicity/safety profiles for each individual product or product lot.

Additionally, vector compositions of the present disclosure may be administered periodically, such as once or twice a day, or any other suitable time period. For example, vector compositions may be administered to a subject in need once a week, once every other week, once every three weeks, once a month, every other month, every three months, every six months, every nine months, once a year, every eighteen months, every two years, every thirty months, or every three years.

In embodiments, the disclosed vector compositions are administered as a pharmaceutical composition. In embodiments, the pharmaceutical composition can be formulated in a wide variety of dosage forms, including but not limited to nasal, pulmonary, oral, topical, or parenteral dosage forms for clinical application. Each of the dosage forms can comprise various solubilizing agents, disintegrating agents, surfactants, fillers, thickeners, binders, diluents such as wetting agents or other pharmaceutically acceptable excipients. The pharmaceutical composition can also be formulated for injection, insufflation, infusion, or intradermal exposure. For instance, an injectable formulation may comprise the disclosed vectors in an aqueous or non-aqueous solution at a suitable pH and tonicity.

The disclosed vector compositions may be administered to a subject via direct injection into a tumor site or at a site of infection. In some embodiments, the vectors can be administered systemically. In some embodiments, the vector compositions can be administered via guided cannulation to tissues immediately surrounding the sites of tumor or infection.

The disclosed vector compositions can be administered using any pharmaceutically acceptable method, such as intranasal, buccal, sublingual, oral, rectal, ocular, parenteral (intravenously, intradermally, intramuscularly, subcutaneously, intraperitoneally), pulmonary, intravaginal, locally administered, topically administered, topically administered after scarification, mucosally administered, via an aerosol, in semi-solid media such as agarose or gelatin, or via a buccal or nasal spray formulation.

Further, the disclosed vector compositions can be formulated into any pharmaceutically acceptable dosage form, such as a solid dosage form, tablet, pill, lozenge, capsule, liquid dispersion, gel, aerosol, pulmonary aerosol, nasal aerosol, ointment, cream, semi-solid dosage form, a solution, an emulsion, and a suspension. Further, the pharmaceutical composition may be a controlled release formulation, sustained release formulation, immediate release formulation, or any combination thereof. Further, the pharmaceutical composition may be a transdermal delivery system.

In embodiments, the pharmaceutical composition can be formulated in a solid dosage form for oral administration, and the solid dosage form can be powders, granules, capsules, tablets or pills. In embodiments, the solid dosage form can include one or more excipients such as calcium carbonate, starch, sucrose, lactose, microcrystalline cellulose or gelatin. In addition, the solid dosage form can include, in addition to the excipients, a lubricant such as talc or magnesium stearate. In some embodiments, the oral dosage form can be immediate release, or a modified release form. Modified release dosage forms include controlled or extended release, enteric release, and the like. The excipients used in the modified release dosage forms are commonly known to a person of ordinary skill in the art.

In embodiments, the pharmaceutical composition can be formulated as a sublingual or buccal dosage form. Such dosage forms comprise sublingual tablets or solution compositions that are administered under the tongue and buccal tablets that are placed between the cheek and gum.

In embodiments, the pharmaceutical composition can be formulated as a nasal dosage form. Such dosage forms of the present invention comprise solution, suspension, and gel compositions for nasal delivery.

In embodiments, the pharmaceutical composition can be formulated in a liquid dosage form for oral administration, such as suspensions, emulsions or syrups. In embodiments, the liquid dosage form can include, in addition to commonly used simple diluents such as water and liquid paraffin, various excipients such as humectants, sweeteners, aromatics or preservatives. In embodiments, the composition can be formulated to be suitable for administration to a pediatric patient.

In embodiments, the pharmaceutical composition can be formulated in a dosage form for parenteral administration, such as sterile aqueous solutions, suspensions, emulsions, non-aqueous solutions or suppositories. In embodiments, the solutions or suspensions can include propyleneglycol, polyethyleneglycol, vegetable oils such as olive oil or injectable esters such as ethyl oleate.

The dosage of the pharmaceutical composition can vary depending on the patient's weight, age, gender, administration time and mode, excretion rate, and the severity of disease.

In embodiments, the treatment of cancer is accomplished by guided direct injection of the disclosed vector constructs into tumors, using needle, or intravascular cannulation. In embodiments, the vectors compositions are administered into the cerebrospinal fluid, blood or lymphatic circulation by venous or arterial cannulation or injection, intradermal delivery, intramuscular delivery or injection into a draining organ near the site of disease.

The following examples are given to illustrate aspects of the present invention. It should be understood, however, that the invention is not to be limited to the specific conditions or details described in these examples. All printed publications referenced herein are specifically incorporated by reference.

EXAMPLES

Example 1: Development of a Lentiviral Vector System

A lentiviral vector system was developed as summarized in FIG. 1 (circularized form). Lentiviral particles were produced in 293T/17 HEK cells (purchased from American Type Culture Collection, Manassas, Va.) following transfection with the therapeutic vector, the envelope plasmid, and the helper plasmid. The transfection of 293T/17 HEK cells, which produced functional viral particles, employed the reagent Poly(ethylenimine) (PEI) to increase the efficiency of plasmid DNA uptake. The plasmids and DNA were initially added separately in culture medium without serum in a ratio of 3:1 (mass ratio of PEI to DNA). After 2-3 days, cell medium was collected and lentiviral particles were purified by high-speed centrifugation and/or filtration followed by anion-exchange chromatography. The concentration of lentiviral particles can be expressed in terms of transducing units/ml (TU/ml). The determination of TU was accomplished by measuring HIV p24 levels in culture fluids (p24 protein is incorporated into lentiviral particles), measuring the number of viral DNA copies per transduced cell by quantitative PCR, or by infecting cells and using light (if the vectors encode luciferase or fluorescent protein markers).

As mentioned above, a 3-vector system (i.e., which includes a 2-vector lentiviral packaging system) was designed for the production of lentiviral particles. A schematic of the 3-vector system is shown in FIG. 1. Briefly, and with reference to FIG. 1, the top-most vector is a helper plasmid, which, in this case, includes Rev. The vector appearing in the middle of FIG. 1 is the envelope plasmid. The bottom-most vector is the therapeutic vector, as described herein.

Referring to FIG. 1, the Helper plus Rev plasmid includes a CAG enhancer (SEQ ID NO: 18); a CAG promoter (SEQ ID NO: 19); a chicken beta actin intron (SEQ ID NO: 20); a HIV gag (SEQ ID NO: 21); a HIV Pol (SEQ ID NO: 22); a HIV Int (SEQ ID NO: 23); a HIV RRE (SEQ ID NO: 24); a HIV Rev (SEQ ID NO: 25); and a rabbit beta globin poly A (SEQ ID NO: 26).

The Envelope plasmid includes a CMV promoter (SEQ ID NO: 27); a beta globin intron (SEQ ID NO: 28); a VSV-G (SEQ ID NO: 29); and a rabbit beta globin poly A (SEQ ID NO: 30).

Synthesis of a 3-Vector System, which Includes a 2-Vector Lentiviral Packaging System, Consisting of Helper (Plus Rev) and Envelope Plasmids.

Materials and Methods:

Construction of the helper plasmid. The helper plasmid was constructed by initial PCR amplification of a DNA fragment from the pNL4-3 HIV plasmid (NIH Aids Reagent Program) containing Gag, Pol, and Integrase genes. Primers were designed to amplify the fragment with EcoRI and NotI restriction sites which could be used to insert at the same sites in the pCDNA3 plasmid (Invitrogen). The forward primer was (5'-TAAGCAGAATTC ATGAATTTGCCAG-GAAGAT-3') (SEQ ID NO: 31) and reverse primer was (5'-CCATACAAT-GAATGGACACTAGGCGGCCGCACGAAT-3') (SEQ ID NO: 32).

The sequence for the Gag, Pol, Integrase fragment was as follows:

(SEQ ID NO: 33)
GAATTCATGAATTTGCCAGGAAGATGGAAACCAAAAATGATAGGGGGA
ATTGGAGGTTTTATCAAAGTAAGACAGTATGATCAGATACTCATAGAA
ATCTGCGGACATAAAGCTATAGGTACAGTATTAGTAGGACCTACACCT
GTCAACATAATTGGAAGAAATCTGTTGACTCAGATTGGCTGCACTTTA
AATTTTCCCATTAGTCCTATTGAGACTGTACCAGTAAAATTAAAGCCA
GGAATGGATGGCCCAAAAGTTAAACAATGGCCATTGACAGAAGAAAAA
ATAAAAGCATTAGTAGAAATTTGTACAGAAATGGAAAAGGAAGGAAAA
ATTTCAAAAATTGGGCCTGAAAATCCATACAATACTCCAGTATTTGCC
ATAAAGAAAAAAGACAGTACTAAATGGAGAAAATTAGTAGATTTCAGA
GAACTTAATAAGAGAACTCAAGATTTCTGGGAAGTTCAATTAGGAATA
CCACATCCTGCAGGGTTAAAACAGAAAAAATCAGTAACAGTACTGGAT
GTGGGCGATGCATATTTTTCAGTTCCCTTAGATAAAGACTTCAGGAAG
TATACTGCATTTACCATACCTAGTATAAACAATGAGACACCAGGGATT
AGATATCAGTACAATGTGCTTCCACAGGGATGGAAAGGATCACCAGCA
ATATTCCAGTGTAGCATGACAAAAATCTTAGAGCCTTTTAGAAAACAA
AATCCAGACATAGTCATCTATCAATACATGGATGATTTGTATGTAGGA
TCTGACTTAGAAATAGGGCAGCATAGAACAAAAATAGAGGAACTGAGA
CAACATCTGTTGAGGTGGGGATTTACCACACCAGACAAAAACATCAG
AAAGAACCTCCATTCCTTTGGATGGGTTATGAACTCCATCCTGATAAA
TGGACAGTACAGCCTATAGTGCTGCCAGAAAAGGACAGCTGGACTGTC
AATGACATACAGAAATTAGTGGGAAAATTGAATTGGGCAAGTCAGATT
TATGCAGGGATTAAAGTAAGGCAATTATGTAAACTTCTTAGGGGAACC
AAAGCACTAACAGAAGTAGTACCACTAACAGAAGAAGCAGAGCTAGAA
CTGGCAGAAAACAGGGAGATTCTAAAAGAACCGGTACATGGAGTGTAT
TATGACCCATCAAAAGACTTAATAGCAGAAATACAGAAGCAGGGGCAA
GGCCAATGGACATATCAAATTTATCAAGAGCCATTTAAAAATCTGAAA
ACAGGAAAGTATGCAAGAATGAAGGGTGCCCACACTAATGATGTAAA
CAATTAACAGAGGCAGTACAAAAAATAGCCACAGAAAGCATAGTAATA
TGGGGAAAGACTCCTAAATTTAAATTACCCATACAAAAGGAAACATGG
GAAGCATGGTGGACAGAGTATTGGCAAGCCACCTGGATTCCTGAGTGG
GAGTTTGTCAATACCCCTCCCTTAGTGAAGTTATGGTACCAGTTAGAG
AAAGAACCCATAATAGGAGCAGAAACTTTCTATGTAGATGGGGCAGCC
AATAGGGAAACTAAATTAGGAAAAGCAGGATATGTAACTGACAGAGGA
AGACAAAAAGTTGTCCCCCTAACGGACACAACAAATCAGAAGACTGAG
TTACAAGCAATTCATCTAGCTTTGCAGGATTCGGGATTAGAAGTAAAC
ATAGTGACAGACTCACAATATGCATTGGGAATCATTCAAGCACAACCA
GATAAGAGTGAATCAGAGTTAGTCAGTCAAATAATAGAGCAGTTAATA

AAAAAGGAAAAAGTCTACCTGGCATGGGTACCAGCACACAAAGGAATT

GGAGGAAATGAACAAGTAGATAAATTGGTCAGTGCTGGAATCAGGAAA

GTACTATTTTTAGATGGAATAGATAAGGCCCAAGAAGAACATGAGAAA

TATCACAGTAATTGGAGAGCAATGGCTAGTGATTTTAACCTACCACCT

GTAGTAGCAAAAGAAATAGTAGCCAGCTGTGATAAATGTCAGCTAAAA

GGGGAAGCCATGCATGGACAAGTAGACTGTAGCCCAGGAATATGGCAG

CTAGATTGTACACATTTAGAAGGAAAAGTTATCTTGGTAGCAGTTCAT

GTAGCCAGTGGATATATAGAAGCAGAAGTAATTCCAGCAGAGACAGGG

CAAGAAACAGCATACTTCCTCTTAAAATTAGCAGGAAGATGGCCAGTA

AAAACAGTACATACAGACAATGGCAGCAATTTCACCAGTACTACAGTT

AAGGCCGCCTGTTGGTGGGCGGGATCAAGCAGGAATTTGGCATTCCC

TACAATCCCCAAAGTCAAGGAGTAATAGAATCTATGAATAAAGAATTA

AAGAAAATTATAGGACAGGTAAGAGATCAGGCTGAACATCTTAAGACA

GCAGTACAAATGGCAGTATTCATCCACAATTTTAAAAGAAAAGGGGGG

ATTGGGGGGTACAGTGCAGGGGAAAGAATAGTAGACATAATAGCAACA

GACATACAAACTAAAGAATTACAAAAACAAATTACAAAAATTCAAAAT

TTTCGGGTTTATTACAGGGACAGCAGAGATCCAGTTTGGAAAGGACCA

GCAAAGCTCCTCTGGAAAGGTGAAGGGGCAGTAGTAATACAAGATAAT

AGTGACATAAAAGTAGTGCCAAGAAGAAAAGCAAAGATCATCAGGGAT

TATGGAAAACAGATGGCAGGTGATGATTGTGTGGCAAGTAGACAGGAT

GAGGATTAA

Next, a DNA fragment containing the Rev, RRE, and rabbit beta globin poly A sequence with XbaI and XmaI flanking restriction sites was synthesized by MWG Operon. The DNA fragment was then inserted into the plasmid at the XbaI and XmaI restriction sites The DNA sequence was as follows:

(SEQ ID NO: 34)
TCTAGAATGGCAGGAAGAAGCGGAGACAGCGACGAAGAGCTCATCAGAAC

AGTCAGACTCATCAAGCTTCTCTATCAAAGCAACCCACCTCCCAATCCCG

AGGGGACCCGACAGGCCCGAAGGAATAGAAGAAGAAGGTGGAGAGAGAGA

CAGAGACAGATCCATTCGATTAGTGAACGGATCCTTGGCACTTATCTGGG

ACGATCTGCGGAGCCTGTGCCTCTTCAGCTACCACCGCTTGAGAGACTTA

CTCTTGATTGTAACGAGGATTGTGGAACTTCTGGGACGCAGGGGGTGGGA

AGCCCTCAAATATTGGTGGAATCTCCTACAATATTGGAGTCAGGAGCTAA

AGAATAGAGGAGCTTTGTTCCTTGGGTTCTTGGGAGCAGCAGGAAGCACT

ATGGGCGCAGCGTCAATGACGCTGACGGTACAGGCCAGACAATTATTGTC

ATGGTATAGTGCAGCGCAGAACAATTTGCTGAGGGCTATTGAGGCGCAAC

AGCATCTGTTGCAACTCACAGTCTGGGGCATCAAGCAGCTCCAGGCAAGA

ATCCTGGCTGTGGAAAGATACCTAAAGGATCAACAGCTCCTAGATCTTTT

TCCCTCTGCCAAAAATTATGGGGACATCATGAAGCCCCTTGAGCATCTGA

CTTCTGGCTAATAAAGGAAATTTATTTTCATTGCAATAGTGTGTTGGAAT

TTTTTGTGTCTCTCACTCGGAAGGACATATGGGAGGGCAAATCATTTAAA

ACATCAGAATGAGTATTTGGTTTAGAGTTTGGCAACATATGCCATATGCT

GGCTGCCATGAACAAAGGTGGCTATAAAGAGGTCATCAGTATATGAAACA

GCCCCCTGCTGTCCATTCCTTATTCCATAGAAAAGCCTTGACTTGAGGTT

AGATTTTTTTATATTTTGTTTTGTGTTATTTTTTTCTTTAACATCCCTA

AAATTTTCCTTACATGTTTTACTAGCCAGATTTTTCCTCCTCTCCTGACT

ACTCCCAGTCATAGCTGTCCCTCTTCTCTTATGAAGATCCCTCGACCTGC

AGCCCAAGCTTGGCGTAATCATGGTCATAGCTGTTTCCTGTGTGAAATTG

TTATCCGCTCACAATTCCACACAACATACGAGCCGGAAGCATAAAGTGTA

AAGCCTGGGGTGCCTAATGAGTGAGCTAACTCACATTAATTGCGTTGCGC

TCACTGCCCGCTTTCCAGTCGGGAAACCTGTCGTGCCAGCGGATCCGCA

TCTCAATTAGTCAGCAACCATAGTCCCGCCCCTAACTCCGCCCATCCCG

CCCCTAACTCCGCCCAGTTCCGCCCATTCTCCGCCCCATGGCTGACTAA

TTTTTTTTATTTATGCAGAGGCCGAGGCCGCCTCGGCCTCTGAGCTATT

CCAGAAGTAGTGAGGAGGCTTTTTTGGAGGCCTAGGCTTTTGCAAAAAG

CTAACTTGTTTATTGCAGCTTATAATGGTTACAAATAAAGCAATAGCAT

CACAAATTTCACAAATAAAGCATTTTTTTCACTGCATTCTAGTTGTGGT

TTGTCCAAACTCATCAATGTATCTTATCAGCGGCCGCCCCGGG

Finally, the CMV promoter of pCDNA3.1 was replaced with the CAG enhancer/promoter plus a chicken beta actin intron sequence. A DNA fragment containing the CAG enhancer/promoter/intron sequence with MluI and EcoRI flanking restriction sites was synthesized by MWG Operon. The DNA fragment was then inserted into the plasmid at the MluI and EcoRI restriction sites. The DNA sequence was as follows:

(SEQ ID NO: 35)
ACGCGTTAGTTATTAATAGTAATCAATTACGGGGTCATTAGTTCATAG

CCCATATATGGAGTTCCGCGTTACATAACTTACGGTAAATGGCCCGCC

TGGCTGACCGCCCAACGACCCCCGCCCATTGACGTCAATAATGACGTA

TGTTCCCATAGTAACGCCAATAGGGACTTTCCATTGACGTCAATGGGT

GGACTATTTACGGTAAACTGCCCACTTGGCAGTACATCAAGTGTATCA

TATGCCAAGTACGCCCCCTATTGACGTCAATGACGGTAAATGGCCCGC

CTGGCATTATGCCCAGTACATGACCTTATGGGACTTTCCTACTTGGCA

GTACATCTACGTATTAGTCATCGCTATTACCATGGTCGAGGTGAGCC

CCACGTTCTGCTTCACTCTCCCCATCTCCCCCCCCTCCCCACCCCCAA

TTTTGTATTTATTTATTTTTTAATTATTTTGTGCAGCGATGGGGGCGG

GGGGGGGGGGGCGCGCGCCAGGCGGGGCGGGGCGGGGCGAGGGGCGG

GGCGGGGCGAGGCGGAGAGGTGCGGCGGCAGCCAATCAGAGCGGCGCG

CTCCGAAAGTTTCCTTTTATGGCGAGGCGGCGGCGGCGGCGGCCCTAT

AAAAAGCGAAGCGCGCGGCGGGCGGGAGTCGCTGCGTTGCCTTCGCCC

CGTGCCCCGCTCCGCGCCGCCTCGCGCCGCCCGCCCCGGCTCTGACTG

ACCGCGTTACTCCCACAGGTGAGCGGGCGGGACGGCCCTTCTCCTCCG

-continued

```
GGCTGTAATTAGCGCTTGGTTTAATGACGGCTCGTTTCTTTTCTGTGG

CTGCGTGAAAGCCTTAAAGGGCTCCGGGAGGGCCCTTTGTGCGGGGGG

GAGCGGCTCGGGGGGTGCGTGCGTGTGTGTGCGTGGGGAGCGCCGC

GTGCGGCCCGCGCTGCCCGGCGGCTGTGAGCGCTGCGGGCGCGGCGCG

GGGCTTTGTGCGCTCCGCGTGTGCGCGAGGGGAGCGCGGCCGGGGGCG

GTGCCCCGCGGTGCGGGGGGGCTGCGAGGGGAACAAAGGCTGCGTGCG

GGGTGTGTGCGTGGGGGGGTGAGCAGGGGGTGTGGGCGCGGCGGTCGG

GCTGTAACCCCCCCCTGCACCCCCCTCCCCGAGTTGCTGAGCACGGCC

CGGCTTCGGGTGCGGGGCTCCGTGCGGGGCGTGGCGCGGGGCTCGCCG

TGCCGGGCGGGGGTGGCGGCAGGTGGGGGTGCCGGGCGGGGCGGGGC

CGCCTCGGGCCGGGGAGGGCTCGGGGGAGGGGCGCGGCGGCCCCGGAG

CGCCGGCGGCTGTCGAGGCGCGGCGAGCCGCAGCCATTGCCTTTTATG

GTAATCGTGCGAGAGGGCGCAGGGACTTCCTTTGTCCCAAATCTGGCG

GAGCCGAAATCTGGGAGGCGCCGCCGCACCCCCTCTAGCGGGCGCGGG

CGAAGCGGTGCGGCGCCGGCAGGAAGGAAATGGGCGGGGAGGGCCTTC

GTGCGTCGCCGCGCCGCCGTCCCCTTCTCCATCTCCAGCCTCGGGGCT

GCCGCAGGGGGACGGCTGCCTTCGGGGGGGACGGGGCAGGGCGGGGTT

CGGCTTCTGGCGTGTGACCGGCGGGAATTC
```

Construction of the VSV-G Envelope Plasmid:

The vesicular stomatitis Indiana virus glycoprotein (VSV-G) sequence was synthesized by MWG Operon with flanking EcoRI restriction sites. The DNA fragment was then inserted into the pCDNA3.1 plasmid (Invitrogen) at the EcoRI restriction site and the correct orientation was determined by sequencing using a CMV specific primer. The DNA sequence was as follows:

```
                                      (SEQ ID NO: 29)
GAATTCATGAAGTGCCTTTTGTACTTAGCCTTTTTATTCATTGGGGTG

AATTGCAAGTTCACCATAGTTTTTCCACACAACCAAAAAGGAAACTGG

AAAAATGTTCCTTCTAATTACCATTATTGCCCGTCAAGCTCAGATTTA

AATTGGCATAATGACTTAATAGGCACAGCCTTACAAGTCAAAATGCCC

AAGAGTCACAAGGCTATTCAAGCAGACGGTTGGATGTGTCATGCTTCC

AAATGGGTCACTACTTGTGATTTCCGCTGGTATGGACCGAAGTATATA

ACACATTCCATCCGATCCTTCACTCCATCTGTAGAACAATGCAAGGAA

AGCATTGAACAAACGAAACAAGGAACTTGGCTGAATCCAGGCTTCCCT

CCTCAAAGTTGTGGATATGCAACTGTGACGGATGCCGAAGCAGTGATT

GTCCAGGTGACTCCTCACCATGTGCTGGTTGATGAATACACAGGAGAA

TGGGTTGATTCACAGTTCATCAACGGAAAATGCAGCAATTACATATGC

CCCACTGTCCATAACTCTACAACCTGGCATTCTGACTATAAGGTCAAA

GGGCTATGTGATTCTAACCTCATTTCCATGGACATCACCTTCTTCTCA

GAGGACGGAGAGCTATCATCCCTGGGAAAGGAGGGCACAGGGTTCAGA

AGTAACTACTTTGCTTATGAAACTGGAGGCAAGGCCTGCAAAATGCAA

TACTGCAAGCATTGGGGAGTCAGACTCCCATCAGGTGTCTGGTTCGAG

ATGGCTGATAAGGATCTCTTTGCTGCAGCCAGATTCCCTGAATGCCCA

GAAGGGTCAAGTATCTCTGCTCCATCTCAGACCTCAGTGGATGTAAGT

AGAAACCTGGAGCAAAATCAGAGCGGGTCTTCCAATCTCTCCAGTGGA

TCTCAGCTATCTTGCTCCTAAAAACCCAGGAACCGGTCCTGCTTTCAC

CATAATCAATGGTACCCTAAAATACTTTGAGACCAGATACATCAGAGT

CGATATTGCTGCTCCAATCCTCTCAAGAATGGTCGGAATGATCAGTGG

AACTACCACAGAAAGGGAACTGTGGGATGACTGGGCACCATATGAAGA

CGTGGAAATTGGACCCAATGGAGTTCTGAGGACCAGTTCAGGATATAA

GTTTCCTTTATACATGATTGGACATGGTATGTTGGACTCCGATCTTCA

TCTTAGCTCAAAGGCTCAGGTGTTCGAACATCCTCACATTCAAGACGC

TGCTTCGCAACTTCCTGATGATGAGAGTTTATTTTTTGGTGATACTGG

GCTATCCAAAAATCCAATCGAGCTTGTAGAAGGTTGGTTCAGTAGTTG

GAAAAGCTCTATTGCCTCTTTTTTCTTTATCATAGGGTTAATCATTGG

ACTATTCTTGGTTCTCCGAGTTGGTATCCATCTTTGCATTAAATTAAA

GCACACCAAGAAAAGACAGATTTATACAGACATAGAGATGAGAATTC
```

Figure 2:
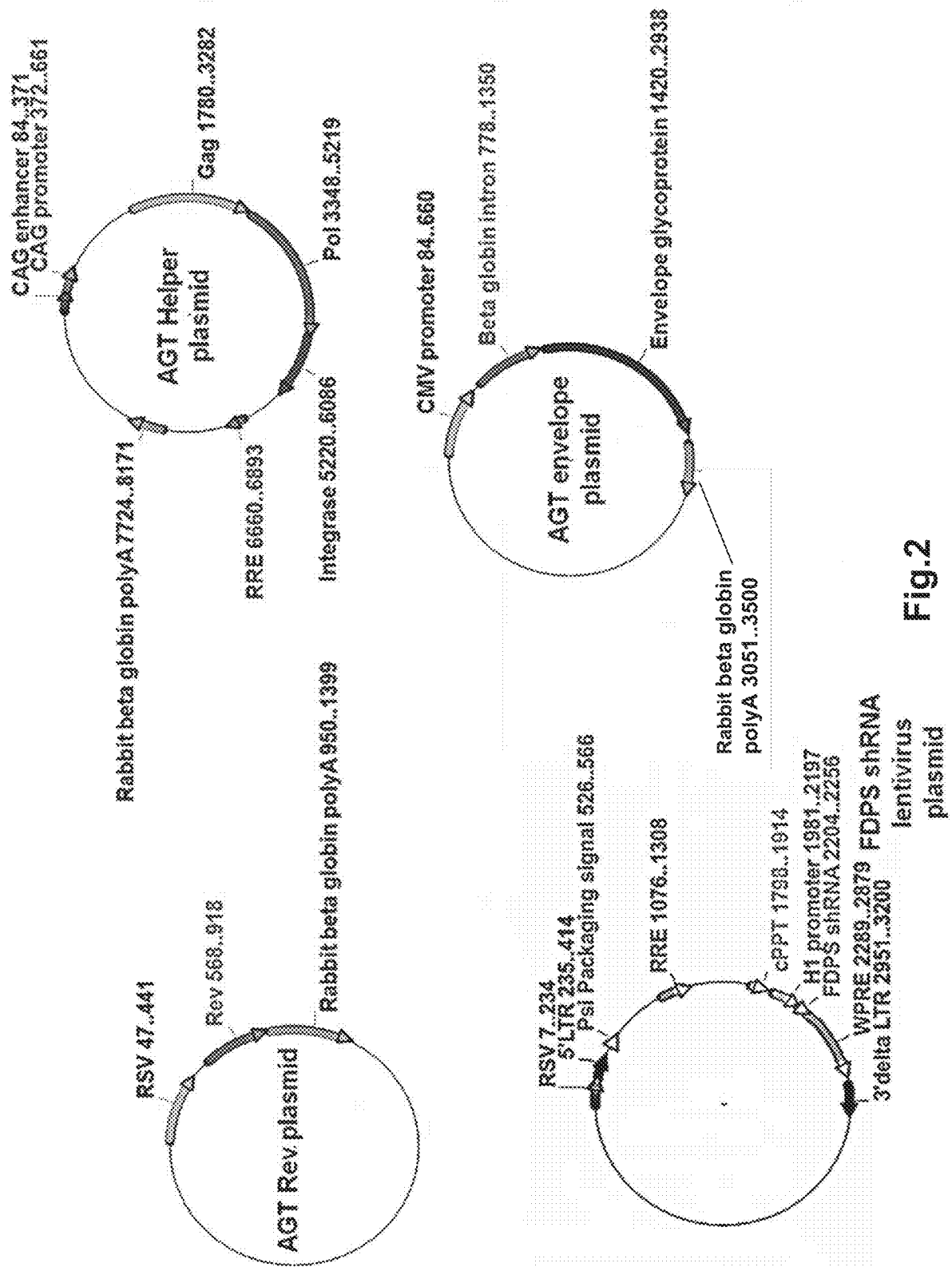
FIG. 2 depicts an exemplary 4-vector lentiviral system in a circularized form.

A 4-vector system, which includes a 3-vector lentiviral packaging system, has also been designed and produced using the methods and materials described herein. A schematic of the 4-vector system is shown in FIG. 2. Briefly, and with reference to FIG. 2, the top-most vector is a helper plasmid, which, in this case, does not include Rev. The vector second from the top is a separate Rev plasmid. The vector second from the bottom is the envelope plasmid. The bottom-most vector is the therapeutic vector as described herein.

Referring to FIG. 2, the Helper plasmid includes a CAG enhancer (SEQ ID NO: 18); a CAG promoter (SEQ ID NO: 19); a chicken beta actin intron (SEQ ID NO: 20); a HIV gag (SEQ ID NO: 21); a HIV Pol (SEQ ID NO: 22); a HIV Int (SEQ ID NO: 23); a HIV RRE (SEQ ID NO: 24); and a rabbit beta globin poly A (SEQ ID NO: 26).

The Rev plasmid includes a RSV promoter (SEQ ID NO: 80); a HIV Rev (SEQ ID NO: 25); and a rabbit beta globin poly A (SEQ ID NO: 26).

The Envelope plasmid includes a CMV promoter (SEQ ID NO: 27); a beta globin intron (SEQ ID NO: 28); a VSV-G (SEQ ID NO: 29); and a rabbit beta globin poly A (SEQ ID NO: 30).

Synthesis of a 4-Vector System, which Includes a 3-Vector Lentiviral Packaging System Consisting of Helper, Rev, and Envelope Plasmids.

Materials and Methods:

Construction of the Helper Plasmid without Rev:

The Helper plasmid without Rev was constructed by inserting a DNA fragment containing the RRE and rabbit beta globin poly A sequence. This sequence was synthesized by MWG Operon with flanking XbaI and XmaI restriction sites. The RRE/rabbit poly A beta globin sequence was then inserted into the Helper plasmid at the XbaI and XmaI restriction sites. The DNA sequence is as follows:

```
                                      (SEQ ID NO: 34)
TCTAGAAGGAGCTTTGTTCCTTGGGTTCTTGGGAGCAGCAGGAAGCAC

TATGGGCGCAGCGTCAATGACGCTGACGGTACAGGCCAGACAATTATT
```

```
GTCTGGTATAGTGCAGCAGCAGAACAATTTGCTGAGGGCTATTGAGGC

GCAACAGCATCTGTTGCAACTCACAGTCTGGGGCATCAAGCAGCTCCA

GGCAAGAATCCTGGCTGTGGAAAGATACCTAAAGGATCAACAGCTCCT

AGATCTTTTTCCCTCTGCCAAAAATTATGGGGACATCATGAAGCCCCT

TGAGCATCTGACTTCTGGCTAATAAAGGAAATTTATTTTCATTGCAAT

AGTGTGTTGGAATTTTTTGTGTCTCTCACTCGGAAGGACATATGGGAG

GGCAAATCATTTAAAACATCAGAATGAGTATTTGGTTTAGAGTTTGGC

AACATATGCCATATGCTGGCTGCCATGAACAAAGGTGGCTATAAAGAG

GTCATCAGTATATGAAACAGCCCCCTGCTGTCCATTCCTTATTCCATA

GAAAAGCCTTGACTTGAGGTTAGATTTTTTTATATTTTGTTTTGTGT

TATTTTTTTCTTTAACATCCCTAAAATTTTCCTTACATGTTTTACTAG

CCAGATTTTTCCTCCTCTCCTGACTACTCCCAGTCATAGCTGTCCCTC

TTCTCTTATGAAGATCCCTCGACCTGCAGCCCAAGCTTGGCGTAATCA

TGGTCATAGCTGTTTCCTGTGTGAAATTGTTATCCGCTCACAATTCCA

CACAACATACGAGCCGGAAGCATAAAGTGTAAAGCCTGGGGTGCCTAA

TGAGTGAGCTAACTCACATTAATTGCGTTGCGCTCACTGCCCGCTTTC

CAGTCGGGAAACCTGTCGTGCCAGCGGATCCGCATCTCAATTAGTCAG

CAACCATAGTCCCGCCCCTAACTCCGCCCATCCCGCCCCTAACTCCGC

CCAGTTCCGCCCATTCTCCGCCCCATGGCTGACTAATTTTTTTATTT

ATGCAGAGGCCGAGGCCGCCTCGGCCTCTGAGCTATTCCAGAAGTAGT

GAGGAGGCTTTTTGGAGGCCTAGGCTTTTGCAAAAAGCTAACTTGTT

TATTGCAGCTTATAATGGTTACAAATAAAGCAATAGCATCACAAATTT

CACAAATAAAGCATTTTTTTCACTGCATTCTAGTTGTGGTTTGTCCA

AACTCATCAATGTATCTTATCACCCGGG
```

Construction of the Rev Plasmid.

The RSV promoter and HIV Rev sequences were synthesized as a single DNA fragment by MWG Operon with flanking MfeI and XbaI restriction sites. The DNA fragment was then inserted into the pCDNA3.1 plasmid (Invitrogen) at the MfeI and XbaI restriction sites in which the CMV promoter is replaced with the RSV promoter. The DNA sequence was as follows:

```
                                              (SEQ ID NO: 36)
CAATTGCGATGTACGGGCCAGATATACGCGTATCTGAGGGGACTAGGG

TGTGTTAGGCGAAAAGCGGGGCTTCGGTTGTACGCGGTTAGGAGTCC

CCTCAGGATATAGTAGTTTCGCTTTTGCATAGGGAGGGGGAAATGTAGT

CTTATGCAATACACTTGTAGTCTTGCAACATGGTAACGATGAGTTAGCA

ACATGCCTTACAAGGAGAGAAAAGCACCGTGCATGCCGATTGGTGGAA

GTAAGGTGGTACGATCGTGCCTTATTAGGAAGGCAACAGACAGGTCTGA

CATGGATTGGACGAACCACTGAATTCCGCATTGCAGAGATAATTGTATT

TAAGTGCCTAGCTCGATACAATAAACGCCATTTGACCATTCACCACATT

GGTGTGCACCTCCAAGCTCGAGCTCGTTTAGTGAACCGTCAGATCGCCT

GGAGACGCCATCCACGCTGTTTTGACCTCCATAGAAGACACCGGGACCG

ATCCAGCCTCCCCTCGAAGCTAGCGATTAGGCATCTCCTATGGCAGGAA

GAAGCGGAGACAGCGACGAAGAACTCCTCAAGGCAGTCAGACTCATCAA

GTTTCTCTATCAAAGCAACCCACCTCCCAATCCCGAGGGGACCCGACAG

GCCCGAAGGAATAGAAGAAGAAGGTGGAGAGAGAGACAGAGACAGATCC

ATTCGATTAGTGAACGGATCCTTAGCACTTATCTGGGACGATCTGCGGA

GCCTGTGCCTCTTCAGCTACCACCGCTTGAGAGACTTACTCTTGATTGT

AACGAGGATTGTGGAACTTCTGGGACGCAGGGGGTGGGAAGCCCTCAAA

TATTGGTGGAATCTCCTACAATATTGGAGTCAGGAGCTAAAGAATAGTC

TAGA
```

The plasmids used in the packaging systems can be modified with similar elements, and the intron sequences can potentially be removed without loss of vector function. For example, the following elements can replace similar elements in the packaging system:

Promoters: Elongation Factor-1 (EF-1) (SEQ ID NO: 37), phosphoglycerate kinase (PGK) (SEQ ID NO: 38), and ubiquitin C (UbC) (SEQ ID NO: 39) can replace the CMV (SEQ ID NO: 27) or CAG promoter (SEQ ID NO: 19). These sequences can also be further varied by addition, substitution, deletion or mutation.

Poly A sequences: SV40 poly A (SEQ ID NO: 40) and bGH poly A (SEQ ID NO: 41) can replace the rabbit beta globin poly A (SEQ ID NO: 26). These sequences can also be further varied by addition, substitution, deletion or mutation.

HIV Gag, Pol, and Integrase sequences: The HIV sequences in the Helper plasmid can be constructed from different HIV strains or clades. For example, HIV Gag (SEQ ID NO: 21); HIV Pol (SEQ ID NO: 22); and HIV Int (SEQ ID NO: 23) from the Bal strain can be interchanged with the gag, pol, and int sequences contained in the helper/helper plus Rev plasmids as outlined herein. These sequences can also be further varied by addition, substitution, deletion or mutation.

Envelope: The VSV-G glycoprotein can be substituted with membrane glycoproteins from feline endogenous virus (RD114) (SEQ ID NO: 42), gibbon ape leukemia virus (GALV) (SEQ ID NO: 43), Rabies (FUG) (SEQ ID NO: 44), lymphocytic choriomeningitis virus (LCMV) (SEQ ID NO: 45), influenza A fowl plague virus (FPV) (SEQ ID NO: 46), Ross River alphavirus (RRV) (SEQ ID NO: 47), murine leukemia virus 10A1 (MLV) (SEQ ID NO: 81), or Ebola virus (EboV) (SEQ ID NO: 48). Sequences for these envelopes are identified in the sequence portion herein. Further, these sequences can also be further varied by addition, substitution, deletion or mutation.

In summary, the 3-vector versus 4-vector systems can be compared and contrasted as follows. The 3-vector lentiviral vector system contains: 1. Helper plasmid: HIV Gag, Pol, Integrase, and Rev/Tat; 2. Envelope plasmid: VSV-G/FUG envelope; and 3. Therapeutic vector: RSV 5'LTR, Psi Packaging Signal, Gag fragment, RRE, Env fragment, cPPT, WPRE, and 3'S LTR. The 4-vector lentiviral vector system contains: 1. Helper plasmid: HIV Gag, Pol, and Integrase; 2. Rev plasmid: Rev; 3. Envelope plasmid: VSV-G/FUG envelope; and 4. Therapeutic vector: RSV 5'LTR, Psi Packaging Signal, Gag fragment, RRE, Env fragment, cPPT, WPRE, and 3'delta LTR. Sequences corresponding with the above elements are identified in the sequence listings portion herein.

Example 2. Therapeutic Vectors

Exemplary therapeutic vectors have been designed and developed as shown, for example, in FIG. 3.

Referring first to FIG. 3A, from left to right, the key genetic elements are as follows: hybrid 5' long terminal repeat (RSV/LTR), Psi sequence (RNA packaging site), RRE (Rev-response element), cPPT (polypurine tract), H1 promoter, an FDPS shRNA sequence including the FDPS shRNA sequences detailed herein, Woodchuck Post-Transcriptional Regulatory Element (WPRE), and LTR with a deletion in the U3 region.

Referring next to FIG. 3B, from left to right, the key genetic elements are as follows: hybrid 5' long terminal repeat (RSV/LTR), Psi sequence (RNA packaging site), RRE (Rev-response element), cPPT (polypurine tract), EF-1 alpha (EF-1 alpha promoter of gene transcription), a FDPS miR (miRNA) including the FDPS miRNA sequences detailed herein, Woodchuck Post-Transcriptional Regulatory Element (WPRE), and LTR with a deletion in the U3 region.

To produce the vectors outlined generally in FIGS. 3A and 3B, the following methods and materials were employed.

Inhibitory RNA Design: The sequence of *Homo sapiens* Farnesyl diphosphate synthase (FDPS) (NM_002004.3) mRNA was used to search for potential siRNA or shRNA candidates to knockdown FDPS levels in human cells. Potential RNA interference sequences were chosen from candidates selected by siRNA or shRNA design programs such as from GPP Web Portal hosted by the Broad Institute (portals.broadinstitute.org/gpp/public/) or the BLOCK-iT RNAi Designer from Thermo Scientific (rnaidesigner.thermofisher.com/rnaiexpress/). Individual selected shRNA sequences were inserted into a lentiviral vector immediately 3 prime to a RNA polymerase III promoter H1 (SEQ ID NO: 15) to regulate shRNA expression. These lentivirus shRNA constructs were used to transduce cells and measure the change in specific mRNA levels. The shRNA most potent for reducing mRNA levels were embedded individually within a microRNA backbone to allow for expression by either the EF-1 alpha or CMV RNA polymerase II promoters. The microRNA backbone was selected from mirbase.org. RNA sequences were also synthesized as synthetic siRNA oligonucleotides and introduced directly into cells without using a lentiviral vector.

Vector Construction: For FDPS shRNA, oligonucleotide sequences containing BamHI and EcoRI restriction sites were synthesized by Eurofins MWG Operon. Overlapping sense and antisense oligonucleotide sequences were mixed and annealed during cooling from 70 degrees Celsius to room temperature. The lentiviral vector was digested with the restriction enzymes BamHI and EcoRI for one hour at 37 degrees Celsius. The digested lentiviral vector was purified by agarose gel electrophoresis and extracted from the gel using a DNA gel extraction kit from Thermo Scientific. The DNA concentrations were determined and vector to oligo (3:1 ratio) were mixed, allowed to anneal, and ligated. The ligation reaction was performed with T4 DNA ligase for 30 minutes at room temperature. 2.5 microliters of the ligation mix were added to 25 microliters of STBL3 competent bacterial cells. Transformation was achieved after heat-shock at 42 degrees Celsius. Bacterial cells were spread on agar plates containing ampicillin and drug-resistant colonies (indicating the presence of ampicillin-resistance plasmids) were recovered and expanded in LB broth. To check for insertion of the oligo sequences, plasmid DNA was extracted from harvested bacteria cultures with the Thermo Scientific DNA mini prep kit. Insertion of shRNA sequences in the lentiviral vector was verified by DNA sequencing using a specific primer for the promoter used to regulate shRNA expression. Using the following target sequences, exemplary shRNA sequences were determined to knockdown FDPS: GTCCTGGAGTACAATGCCATT (FDPS target sequence; SEQ ID NO: 49); GTCCTGGAGTACAATGCCATTCTCGAGAATGGCATTGTACTCCAGGACTTTTT (FDPS shRNA sequence #1; SEQ ID NO: 1); GCAGGATTTCGTTCAGCACTT (FDPS target sequence #2; SEQ ID NO: 50); GCAGGATTCGTTCAGCACTTCTCGAGAAGTGCTGAACGAAATCCTGCTTTTTT (FDPS shRNA sequence #2; SEQ ID NO: 2); GCCATGTACATGGCAGGAATT (FDPS target sequence #3; SEQ ID NO: 51); GCCATGTACATGGCAGGAATTCTCGAGAATTCCTGCCATGTACATGGCTTTTT (FDPS shRNA sequence #3; SEQ ID NO: 3); GCAGAAGGAGGCTGAGAAAGT (FDPS target sequence #4; SEQ ID NO: 52); and GCAGAAGGAGGCTGAGAAAGTCTCGAGACTTTCTCAGCCTCCTTCTGCTTTTT (FDPS shRNA sequence #4; SEQ ID NO: 4).

shRNA sequences were then assembled into a synthetic microRNA (miR) under control of the EF-1 alpha promoter. Briefly, a miR hairpin sequences, such as miR30, miR21, or miR185 as detailed below, was obtained from mirbase.org. The 19-22mer shRNA target sequence was used to construct the synthetic miR sequence. The miR sequence was arranged as an anti-sense-target-sequence-hairpin loop sequence (specific for each microRNA)-sense target sequence.

The following miR sequences were developed:

```
AAGGTATATTGCTGTTGACAGTGAGCGACACTTTCTCAGCCTCCTTCT
GCGTGAAGCCACAGATGGCAGAAGGAGGCTGAGAAAGTGCTGCCTACT
GCCTCGGACTTCAAGGGGCT (miR30 FDPS sequence #1; SEQ
ID NO: 53)

AAGGTATATTGCTGTTGACAGTGAGCGACACTTTCTCAGCCTCCTTCT
GCGTGAAGCCACAGATGGCAGAAGGGCTGAGAAAGTGCTGCCTACTGC
CTCGGACTTCAAGGGGCT (miR30 FDPS sequence #2; SEQ
ID NO: 54)

TGCTGTTGACAGTGAGCGACTTTCTCAGCCTCCTTCTGCGTGAAGCCA
CAGATGGCAGAAGGAGGCTGAGAAAGTTGCCTACTGCCTCGGA
(miR30 FDPS sequence #3; SEQ ID NO: 55)

CCTGGAGGCTTGCTGAAGGCTGTATGCTGACTTTCTCAGCCTCCTTCT
GCTTTTGGCCACTGACTGAGCAGAAGGGCTGAGAAAGTCAGGACACAA
GGCCTGTTACTAGCACTCA (miR155 FDPS sequence #1; SEQ
ID NO: 56)
```

CATCTCCATGGCTGTACCACCTTGTCGGGACTTTCTCAGCCTCCTTCT

GCCTGTTGAATCTCATGGCAGAAGGAGGCGAGAAAGTCTGACATTTTG

GTATCTTTCATCTGACCA (miR21 FDPS sequence #1; SEQ ID NO: 57)

GGGCCTGGCTCGAGCAGGGGGCGAGGGATACTTTCTCAGCCTCCTTCTG

CTGGTCCCCTCCCCGCAGAAGGAGGCTGAGAAAGTCCTTCCCTCCCAAT

GACCGCGTCTTCGTCG (miR185 FDPS sequence #1; SEQ ID NO: 58)

Combination vectors, as shown generally in FIG. 3C are also capable of being produced based on the development of the single-target vectors outlined above. An exemplary therapeutic combination vectors is shown in FIG. 3C, and includes from left to right: hybrid 5' long terminal repeat (RSV/LTR), Psi sequence (RNA packaging site), RRE (Rev-response element), cPPT (polypurine tract), EF-1alpha (EF-1alpha promoter of gene transcription), miR30-FDPS, miR155-CD47, miR21-cMyc, Woodchuck Post-Transcriptional Regulatory Element (WPRE), and LTR with a deletion in the U3 region. The therapeutic vector detailed in FIG. 3C can be produced using the materials and methods described using the following target sequences:

miR30 FDPS sequence #1:

(SEQ ID NO: 53)
AAGGTATATTGCTGTTGACAGTGAGCGACACTTTCTCAGCCTCCTT

CTGCGTGAAGCCACAGATGGCAGAAGGAGGCTGAGAAAGTGCTGCC

TACTGCCTCGGACTTCAAGGGGCT miR155 CD47 target sequence #1:

(SEQ ID NO: 82)
CCTGGAGGCTTGCTGAAGGCTGTATGCTGTTATCCATCTTCAAAGA

GGCAGTTTTGGCCACTGACTGACTGCCTCTTAAGATGGATAACAGG

ACACAAGGCCTGTTACTAGCACTCA miR21 cMyc sequence:

(SEQ ID NO: 83)
CATCTCCATGGCTGTACCACCTTGTCGGGTGTTCGCCTCTTGACAT

TCTCCTGTTGAATCTCATGGAGAATGTCAAGGGCGAACACTGACAT

TTTGGTATCTTTCATCTGACCA

Example 3. Materials and Methods for FDPS

Inhibitory RNA Design: The sequence of *Homo sapiens* farnesyl diphosphate synthase (FDPS), transcript variant 1, mRNA (NM_002004.3) was used to search for potential siRNA or shRNA candidates to knockdown FDPS levels in human cells. Potential RNA interference sequences were chosen from candidates selected by siRNA or shRNA design programs such as from the Broad Institute or the BLOCK-iT™ RNAi Designer from Thermo Scientific. A shRNA sequence may be inserted into a lentiviral vector after a RNA polymerase III promoter such as H1, U6, or 7SK to regulate shRNA expression. The RNA sequence may also be embedded within a microRNA backbone to allow for expression by a RNA polymerase II promoter such as CMV or EF-1 alpha. The RNA sequence may also be synthesized as a siRNA oligonucleotide and utilized independently of a lentiviral vector.

Vector Construction: For FDPS shRNA, oligonucleotide sequences containing BamHI and EcoRI restriction sites were synthesized by MWG operon. Oligonucleotide sequences were annealed by incubation at 70 degrees Celsius and cooling to room temperature. Annealed oligonucleotides were digested with the restriction enzymes BamHI and EcoRI for one hour at 37 degrees Celsius and then the enzymes were heat-inactivated at 70 degrees Celsius for 20 minutes. In parallel, the lentiviral vector was digested with the restriction enzymes BamHI and EcoRI for one hour at 37 degrees Celsius. The digested lentiviral vector was purified by agarose gel electrophoresis and extracted from the gel using a DNA gel extraction kit from Invitrogen. The DNA concentration was determined and the vector to oligo sequence was ligated in the ratio 3:1 insert to vector. The ligation reaction was carried out with T4 DNA ligase for 30 minutes at room temperature. 2.5 microliters of the ligation mix was added to 25 microliters of STBL3 competent bacterial cells. Transformation was carried out by heat-shock at 42 degrees Celsius. Bacterial cells were streaked onto agar plates containing ampicillin and then colonies were expanded in LB broth. To check for insertion of the oligo sequences, plasmid DNA was extracted from harvested bacteria cultures with the Invitrogen DNA mini prep kit. Insertion of the shRNA sequence in the lentiviral vector was verified by DNA sequencing using a specific primer for which every promoter is used to regulate shRNA expression. The lentiviral vectors containing a correct FDPS sequence were then used to package lentiviral particles to test for their ability to knockdown FDPS. Mammalian cells were transduced with lentiviral particles either in the presence or absence of polybrene. Cells were collected after 2-4 days and protein and RNA was analyzed for FDPS expression.

Functional Assay for mRNA reduction: The effect of different FDPS short homology RNA (shRNA) targeting sequences on FDPS expression was determined by measuring mRNA expression. HepG2 hepatocellular carcinoma cells were transduced with a lentiviral vector containing FDPS shRNA sequences. After 48 hours, cells were lysed and RNA was extracted using the RNeasy mini kit from Qiagen. cDNA was then synthesized from RNA using SuperScript VILO from Invitrogen. The samples were then analyzed by quantitative RT-PCR using an Applied Biosystems StepOne PCR machine. FDPS expression was detected with SYBR Green from Invitrogen using the forward primer (5'-AGGAATTGATGGCGAGAAGG-3') (SEQ ID NO: 59) and reverse primer (5'-CCCAAAGAGGT-CAAGGTAATCA-3') (SEQ ID NO: 60) with standard conditions for polymerase chain reaction analysis. The samples were normalized to the mRNA for beta-actin gene expression using the forward primer (5'-AGCGCGGCTA-CAGCTTCA-3') (SEQ ID NO: 61) and reverse primer (5'-GGCGACGTAGCACAGCTTCT-3') (SEQ ID NO: 62) with standard conditions for polymerase chain reaction analysis. The relative expression of FDPS was determined by its Ct value normalized to the level of actin for each sample.

Functional Assay for tumor cells modified by LV-FDPS and used to activate cytokine production in human gamma delta T cells: The LV-FDPS vector was also used to treat tumor cells that were then exposed to primary human gamma delta T cells from healthy donors. Combined treatment of tumor cell line with both aminobisphosphonate and vector that suppresses farnesyl pyrophosphate synthase (FDPS) has a synergistic effect on gamma delta T cell production of TNF-alpha. THP1 monocytoid tumor cell line (A) or HepG2 monocytoid tumor cell line (B) were treated with lentiviral control vectors (LV-Control), lentiviral vectors expressing shRNA to down regulate FDPS (LV-FDPS), zoledronic acid (Zol), zoledronic acid plus lentiviral control (Zol+LV-Control), or zoledronic acid plus lentiviral vectors expressing shRNA to down regulate FDPS (Zol+LV-FDPS). Treated cells were mixed with gamma delta T cells at 1:1 ratio for 4 hours. TNF-alpha production by gamma delta T cells was detected by intracellular staining and flow cytometry.

Functional Assay for tumor cells modified by LV-FDPS and used to activate tumor cell killing by human gamma delta T cells: Monocytoid tumor cells (THP-1) were transduced with lentivirus vector that suppresses FDPS mRNA, then used to activate tumor cell cytotoxicity in normal human gamma delta T cells. The activated gamma delta T cells were recovered after 4 hours of exposure to transduced THP-1 cells, then used in a cytotoxicity assay to kill unmodified THP-1. When gamma delta T cells were stimulated with a combination of transduced THP-1 cells and 10 micromolar zoledronic acid, >70% killing of THP-1 was observed at a ratio of 4 gamma delta T cells to 1 THP-1 cell.

Experimental Data for FDPS

The FDPS shRNA sequences depicted in Table 2 were utilized in the experiments described herein. Further, the sequences detailed in Table 2 can be used in the therapeutic vectors detailed herein.

TABLE 2

FDPS shRNA sequences

| Description | shRNA oligonucleotide (sense sequence - loop - antisense sequence | SEQ ID NO |
|---|---|---|
| FDPS-1 | GTCCTGGAGTACAATGCCATTCTCGAGAATGGCATTGTACTCCAGGACTTTTT | 1 |
| FDPS-2 | GCAGGATTTCGTTCAGCACTTCTCGAGAAGTGCTGAACGAAATCCTGCTTTTT | 2 |
| FDPS-3 | GCCATGTACATGGCAGGAATTCTCGAGAATTCCTGCCATGTACATGGCTTTTT | 3 |
| FDPS-4 | GCAGAAGGAGGCTGAGAAAGTCTCGAGACTTTCTCAGCCTCCTTCTGCTTTTT | 4 |

Figure 4A:
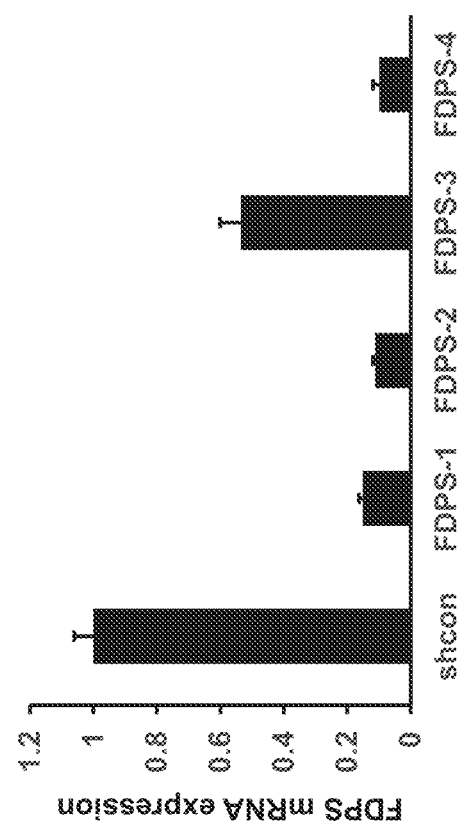
FIGS. 4A-4B depict.

As shown in FIG. 4A, the relative expression level of human FDPS following administration of the four different FDPS shRNA sequences was determined. The most significant inhibition of human FDPS expression was found in the FDPS-2 and FDPS-4 samples (as shown in FIG. 4A, herein).

Figure 4B:
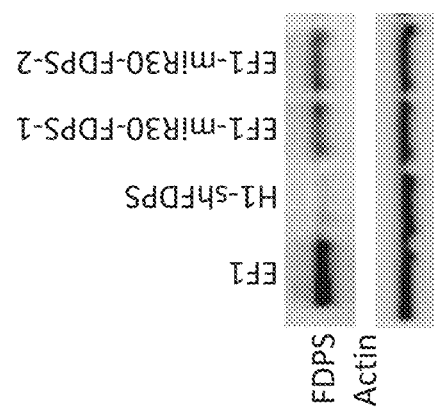

Further, as shown in FIG. 4B, a lentiviral-based delivery system was used to target FDPS expression. HepG2 human hepatocellular carcinoma cells were infected with lentiviral vectors containing either the H1 promoter and a FDPS shRNA (SEQ ID NO: 4) sequence or the EF-1alpha promoter and the following miR30-based FDPS sequences: miR30 FDPS sequence #1:

(SEQ ID NO: 53)
AAGGTATATTGCTGTTGACAGTGAGCGACACTTTCTCAGCCTCCT

TCTGCGTGAAGCCACAGATGGCAGAAGGAGGCTGAGAAAGTGCTG

CCTACTGCCTCGGACTTCAAGGGGCT miR30 FDPS sequence #2:

(SEQ ID NO: 54)
AAGGTATATTGCTGTTGACAGTGAGCGACACTTTCTCAGCCTCCT

TCTGCGTGAAGCCACAGATGGCAGAAGGGCTGAGAAAGTGCTGCC

TACTGCCTCGGACTTCAAGGGGCT

After 48 hours, cells were lysed and an immunoblot was performed using an anti-FDPS (Thermo Scientific) and an anti-actin (Sigma) antibody for a protein loading control. As shown in FIG. 4B, treatment with the FDPS shRNA significantly decreased FDPS protein expression. Treatment with the miR30-based FDPS sequences decreased FDPS expression.

Figure 5A:
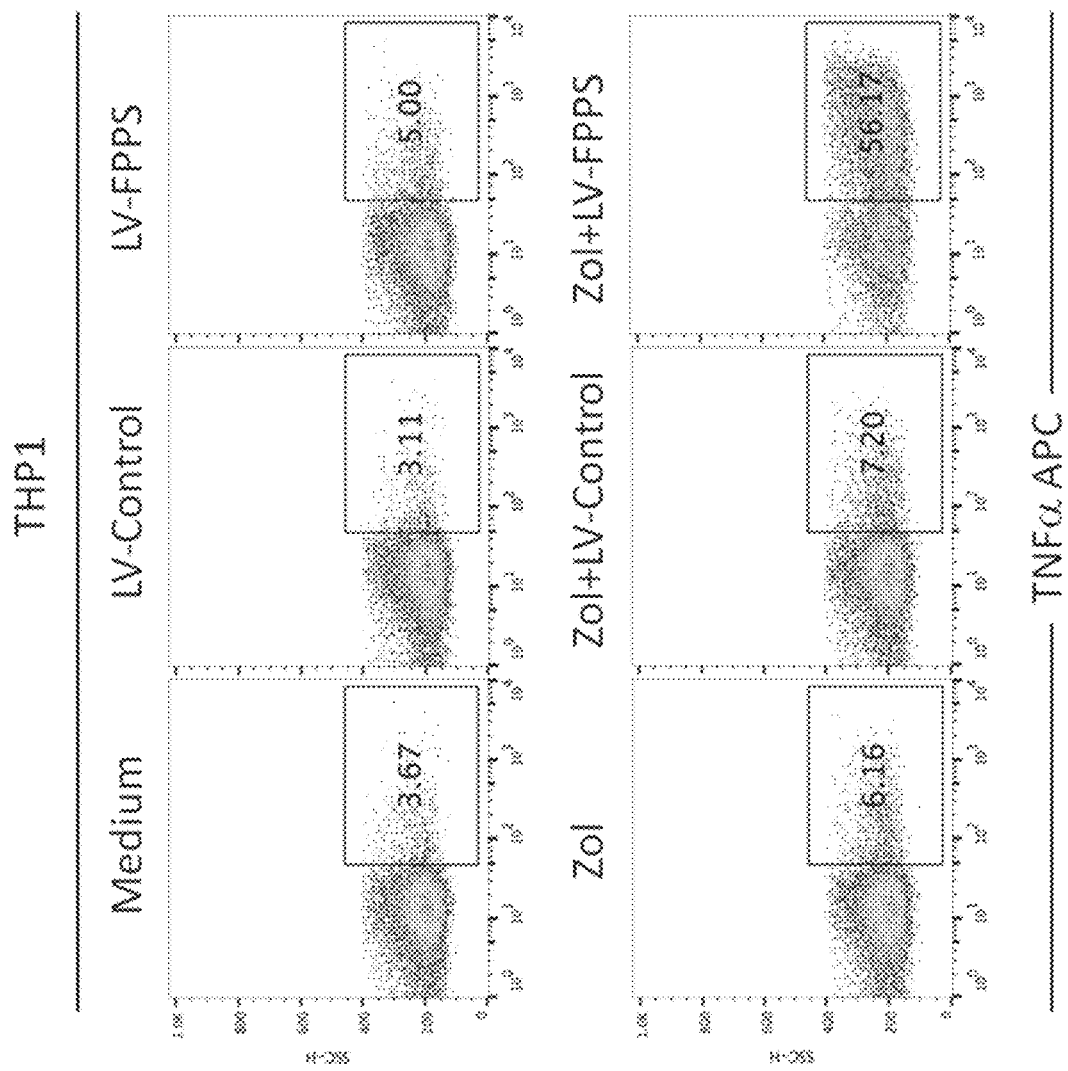
FIGS. 5A-5B depict cytokine expression levels in human peripheral blood gamma delta T cells after exposure to (FIG. 5A) THP1 or (FIG. 5B) HepG2 cells that have been transduced with lentivirus to suppress FDPS.
Figure 5B:
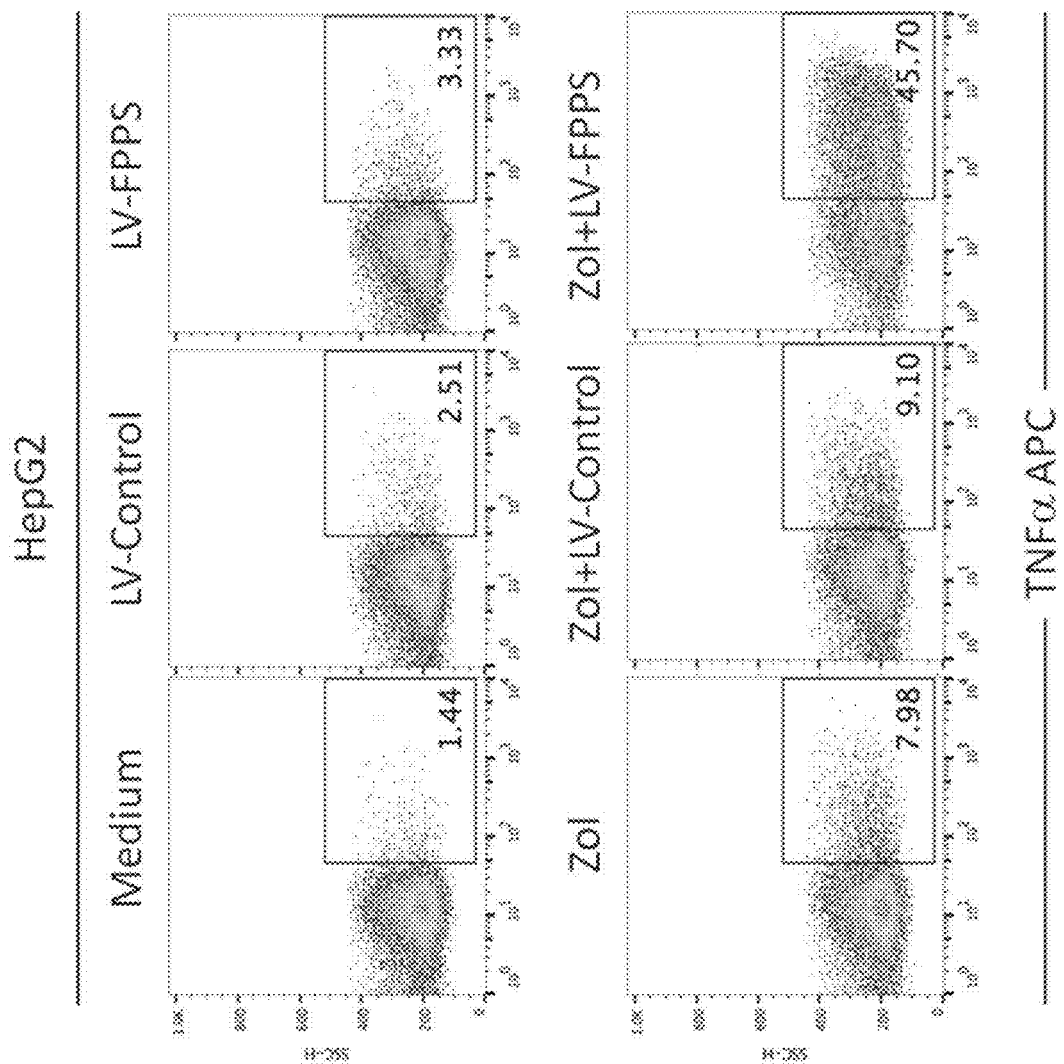

As shown in FIG. 5, monocytoid (THP-1) (FIG. 5A) or hepatocellular (HepG2) (FIG. 5B) cancer cells transduced with lentivirus containing shRNA capable of suppressing FDPS mRNA activated cytokine expression in human gamma delta T cells.

This portion of the Example illustrates that knock-down of FDPS in THP1 monocytic leukemia cells by lentiviral (LV)-expressing FDPS shRNA (SEQ ID NO: 4; which is also referred to herein as LV-FDPS shRNA #4) stimulates TNF-α expression in gamma delta T cells, as shown in FIG. 5A.

THP1 cells ($1\times10^5$ cells) were transduced with LV-control or LV-FDPS shRNA #4 for 3 days. Two days after transduction, cells were treated with or without 1p M zoledronic acid. After 24 hours, the transduced THP-1 cells were co-cultured with $5\times10^5$ PBMC cells and IL-2 in a round bottom 96 well plate for 4 hours. The PBMC cells were pre-stimulated with zoledronic acid and IL-2 for 11 days to expand Vy9V62 T cells. After staining for Vy9VS2 and TNF-α using fluorophore-conjugated anti TCR-VS2 and anti-TNF-α antibody, cells were analyzed via flow cytometry. Live cells were gated, and VS2+ and TNF-α+ cells were selected on a dot blot. The activated cytotoxic Vy9VS2 T cells appeared in the upper right quadrant of flow cytograms. Without zoledronic acid, LV-control stimulated 3.11% of TNF-α expressing Vy9VS2 T cells and LV-FDPS shRNA #4 stimulated 5%. With zoledronic acid treatment, LV-control stimulated 7.2% of TNF-α expressing Vy9VS2 T cells and LV-FDPS shRNA #4 stimulated 56.17%.

The same conditions were used with HepG2 cells and the following data was generated. Without zoledronic acid, LV-control stimulated 2.5% of TNF-α expressing V79VS2 T cells and LV-FDPS shRNA #4 stimulated 3.33%. With zoledronic acid treatment, LV-control stimulated 9.1% of TNF-α expressing Vy9VS2 T cells and LV-FDPS shRNA #4 stimulated 45.7%.

Figure 6:
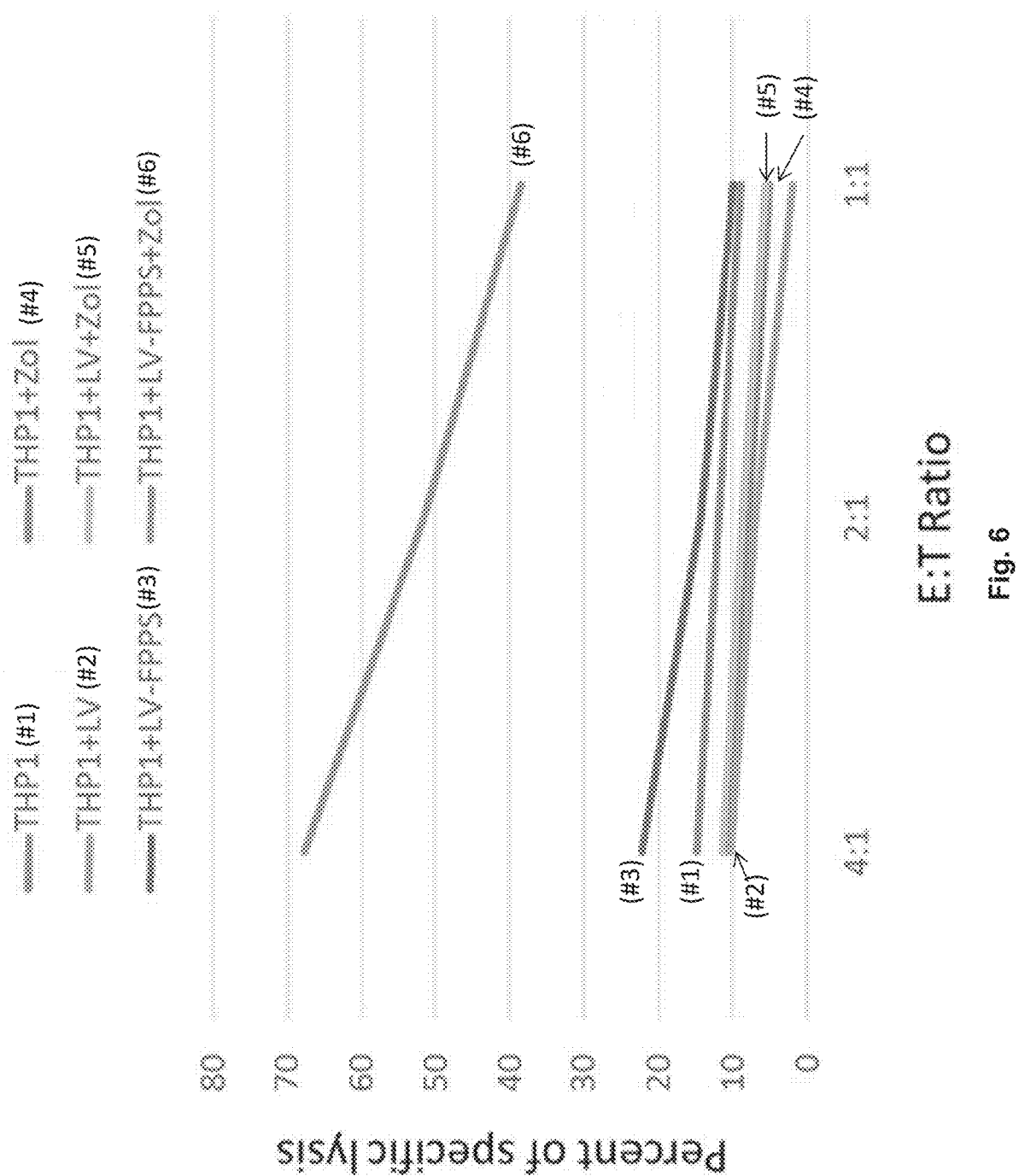
FIG. 6 depicts percent specific lysis of THP-1 tumor cell line that was modified by lentiviral transduction to suppress FDPS then mixed with normal human gamma delta T cells under a variety of experimental conditions as described herein.

Further as shown in FIG. 6, monocytoid (THP-1) tumor cells transduced with lentivirus capable of suppressing FDPS mRNA activate tumor cell cytotoxicity in normal human gamma delta T cells.

This portion of the Example demonstrates results from mixing treated THP-1 monocytoid tumor cells with cultured human GD T cells, as shown in FIG. 6.

The monocytoid cell line THP-1 was treated with control lentivirus vector (LV), LV suppressing farnesyl diphosphate synthase gene expression (LV-FDPS), zoledronic acid (Zol) or combinations. The legend, as shown in FIG. 6, was: lentiviral control vectors (LV-Control), lentiviral vectors expressing microRNA to down regulate FDPS (LV-FDPS), Zometa (Zol), Zometa plus lentiviral control (Zol+LV-Control), or Zometa plus lentiviral vectors expressing microRNA to down regulate FDPS (Zol+LV-FDPS).

Human GD T cells were cultured from an anonymous donor and added to treated THP-1 cells in 4:1. 2:1 or 1:1 ratios (GD T:THP-1) for 4 hours. Cell killing was measured by a fluorescence assay. When THP-1 cells were treated with a combination of LV-FDPS and Zol, cytotoxic T cell killing by GD T cells was increased greatly compared to either treatment alone. When LV-FDPS treatment alone was compared to Zol treatment alone, the LV-FDPS lead to greater killing but was >3-fold below tumor cell killing after combination treatment. The combined LV-FDPS plus Zol treatment caused nearly 70% tumor cell killing with 4:1 ratio; this was more than 3-fold higher than the second best treatment (LV-FDPS alone).

Example 4. Materials and Methods for CD47

Inhibitory RNA Selection: The sequence of *Homo sapiens* CD47 molecule (CD47) mRNA (NM_001777) was used to search for potential siRNA or shRNA candidates capable of reducing CD47 levels in human cells. Potential RNA interference sequences were chosen from candidates selected by siRNA or shRNA design programs such as from the Broad Institute or the BLOCK-iT™ RNAi Designer from Thermo Scientific. Initially, individual selected shRNA sequences were inserted into lentiviral vectors immediately 3' to a RNA polymerase III promoter such as H1, U6, or 7SK to regulate shRNA expression. These lentivirus-shRNA constructs were used to transduce cells and measure the change in specific mRNA levels. The shRNA most potent for reducing mRNA levels were embedded individually within a microRNA backbone to allow for expression by either the CMV or EF-1alpha RNA polymerase II promoters. RNA sequences have also been synthesized as synthetic siRNA oligonucleotides and introduced directly into cells without using a lentiviral vector.

Vector Construction: For CD47 shRNA, oligonucleotide sequences containing BamHI and EcoRI restriction sites were synthesized by Eurofins MWG Operon, LLC. Overlapping sense and antisense oligonucleotide sequences were mixed and annealed during incubation at 70 degrees Celsius before being cooled to room temperature and extending the unpaired ends with DNA polymerase before cooling to room temperature. The extension reaction created double stranded sequences at each end of the oligonucleotide that contain restriction enzyme sites BamHI and EcoRI. The double stranded oligonucleotides were digested with the restriction enzymes BamHI and EcoRI for one hour at 37 degrees Celsius and the enzymes were heat-inactivated at 70 degrees Celsius for 20 minutes. In parallel, the lentiviral vector was digested with the restriction enzymes BamHI and EcoRI for one hour at 37 degrees Celsius. The digested lentiviral vector was purified by agarose gel electrophoresis and extracted from the gel using a DNA gel extraction kit from Invitrogen. The DNA concentrations were determined and vector to oligo (3:1 ratio) were mixed, allowed to anneal, and ligated. The ligation reaction was performed with T4 DNA ligase for 30 minutes at room temperature. 2.5 microliters of the ligation mix were added to 25 microliters of STBL3 competent bacterial cells. Transformation was achieved after heat-shock at 42 degrees Celsius. Bacterial cells were spread on agar plates containing ampicillin and drug-resistant colonies (indicating the presence of ampicillin-resistance plasmids) were recovered, purified and expanded in LB broth. To check for insertion of the oligo sequences, plasmid DNA were extracted from harvested bacteria cultures with the Invitrogen DNA mini prep kit. Insertion of the shRNA sequence in the lentiviral vector was verified by DNA sequencing using a specific primer for the promoter used to regulate shRNA expression.

Functional Assay: The effect of different CD47 shRNA targeting sequences on CD47 expression was determined by measuring mRNA expression. Hep3B hepatocellular carcinoma cells were transduced with a lentiviral vector containing CD47 shRNA sequences. After 48 hours, cells were lysed and RNA was extracted using the RNeasy mini kit from Qiagen. cDNA was then synthesized from RNA using SuperScript VILO from Invitrogen. The samples were then analyzed by quantitative RT-PCR using an Applied Biosystems StepOne PCR machine. CD47 expression was detected with SYBR Green from Invitrogen using the forward primer (5'-CACTGTCGTCATTCCATGCT-3') (SEQ ID NO: 63) and reverse primer (5'-GCCTCTTGACATTCTCCTC-3') (SEQ ID NO: 64). The samples were normalized by measuring actin expression using the forward primer (5'-AGCGCGGCTACAGCTTCA-3') (SEQ ID NO: 61) and reverse primer (5'-AAAGTCAGTGGGGACAGTGG-3') (SEQ ID NO: 65). The relative expression of CD47 was determined by its Ct value normalized to the level of actin for each sample.

Experimental Data for CD47

The non-limiting examples of CD47 shRNA target sequences depicted in Table 3 were utilized in the experiments described herein. Further, the sequences detailed in Table 3 can be used in the therapeutic vectors detailed herein.

TABLE 3

CD47 shRNA sequences

| Description | shRNA oligonucleotide (sense sequence - loop - antisense sequence | SEQ ID NO |
|---|---|---|
| CD47 sequence 1 | GGTGAAACGATCATCGAGCCTCGAGGCT CGATGATCGTTTCACCTTTTT | 5 |
| CD47 sequence 2 | GCTACTGGCCTTGGTTTAACTCGAGTTA AACCAAGGCCAGTAGCTTTTT | 6 |
| CD47 sequence 3 | CCTCCTTCGTCATTGCCATCTCGAGATG GCAATGACGAAGGAGGTTTTT | 7 |
| CD47 sequence 4 | GCATGGCCCTCTTCTGATTCTCGAGAAT CAGAAGAGGGCCATGCTTTTT | 8 |
| CD47 sequence 5 | TGATCGTGGTGAAACGATCATCGAGCTA CTCGAGTAGCTCGATTCACCTTTTT | 9 |

Figure 7A:
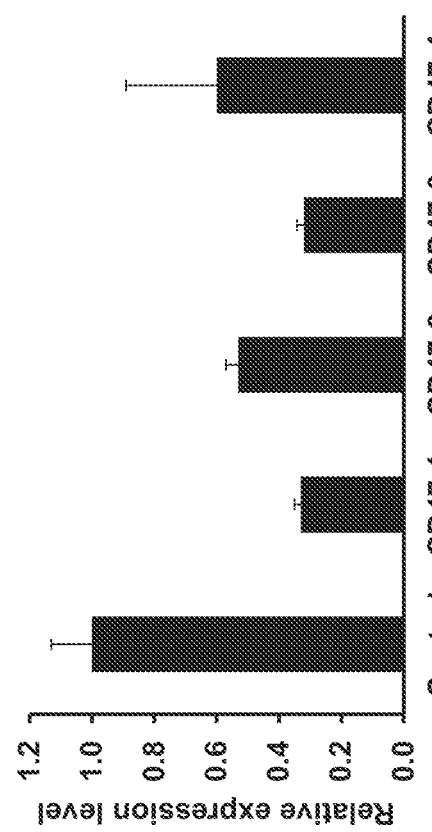
FIGS. 7A-7B depict.

As shown in FIG. 7A, the relative expression level of human CD47 following administration of the four different CD47 shRNA sequences was determined. The most significant inhibition of human CD47 expression was found in the shCD47-1 and shCD47-3 samples (as shown in FIG. 7A, herein).

Figure 7B:
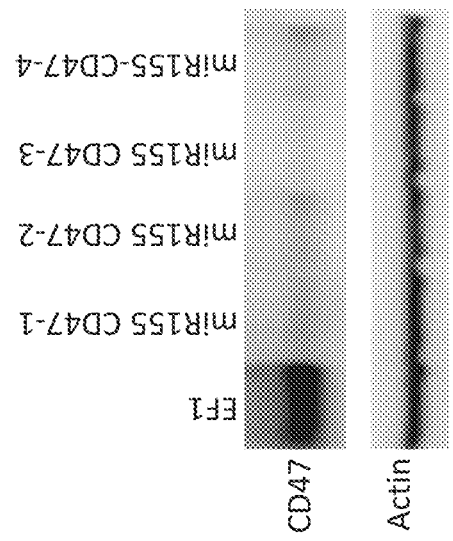

Further, as shown in FIG. 7B, a lentiviral-based delivery system was used to target CD47 expression. SNU449 human hepatocellular carcinoma cells were infected with lentiviral vectors containing the following miR155-based CD47 sequences:

miR155 CD47 target sequence #1:

(SEQ ID NO: 82)
CCTGGAGGCTTGCTGAAGGCTGTATGCTGTTATCCATCTTCAAAG

AGGCAGTTTTGGCCACTGACTGACTGCCTCTTAAGATGGATAACA

GGACACAAGGCCTGTTACTAGCACTCA miR155 CD47 target sequence #2:

(SEQ ID NO: 66)
CCTGGAGGCTTGCTGAAGGCTGTATGCTGTTAGCTCGATGATCGTTT

CACGTTTTGGCCACTGACTGACGTGAAACGCATCGAGCTAACAGGAC

ACAAGGCCTGTTACTAGCACTCA miR155 CD47 target sequence #3:

(SEQ ID NO: 67)
CCTGGAGGCTTGCTGAAGGCTGTATGCTGAAGAATGGCTCCAACAAT

GACGTTTTGGCCACTGACTGACGTCATTGTGAGCCATTCTTCAGGAC

ACAAGGCCTGTTACTAGCACTCA miR155 CD47 target sequence #4:

(SEQ ID NO: 68)
CCTGGAGGCTTGCTGAAGGCTGTATGCTGTATACACGCCGCAATACA

GAGGTTTTGGCCACTGACTGACCTCTGTATCGGCGTGTATACAGGAC

ACAAGGCCTGTTACTAGCACTCA

As shown in FIG. 7B, treatment with the CD47 shRNA significantly decreased FDPS protein expression. Treatment with the miR155-based CD47 sequences significant decreased CD47 expression.

Example 5. Materials and Methods for cMyc

Inhibitory RNA Design: The mRNA sequence of *Homo sapiens* v-myc avian myelocytomatosis viral oncogene homolog (MYC) (NM_002467.4) was used to screen for potential shRNA candidates to knock-down MYC expression in hepatocellular cell lines. We obtained five MYC shRNA sequences which can reduce MYC expression. Potential RNA interference sequences were chosen from candidates selected by siRNA or shRNA design programs such as from the Broad Institute or the BLOCK-iT™ RNAi Designer from Thermo Scientific. A shRNA sequence may be inserted into a lentiviral vector after a RNA polymerase III promoter such as H1, U6, or 7SK to regulate shRNA expression. The RNA sequence may also be embedded within a microRNA backbone to allow for expression by a RNA polymerase II promoter such as CMV or EF-1 alpha. The RNA sequence may also be synthesized as a siRNA oligonucleotide and utilized independently of a lentiviral vector.

Vector Construction: For cMyc shRNA, oligonucleotide sequences containing BamHI and EcoRI restriction sites were synthesized by MWG operon. Oligonucleotide sequences were annealed by incubation at 70 degrees Celsius and cooling to room temperature. Annealed oligonucleotides were digested with the restriction enzymes BamHI and EcoRI for one hour at 37 degrees Celsius and then the enzymes were heat-inactivated at 70 degrees Celsius for 20 minutes. In parallel, the lentiviral vector was digested with the restriction enzymes BamHI and EcoRI for one hour at 37 degrees Celsius. The digested lentiviral vector was purified by agarose gel electrophoresis and extracted from the gel using a DNA gel extraction kit from Invitrogen. The DNA concentration was determined and the vector to oligo sequence was ligated in the ratio 3:1 insert to vector. The ligation reaction was carried out with T4 DNA ligase for 30 minutes at room temperature. 2.5 microliters of the ligation mix was added to 25 microliters of STBL3 competent bacterial cells. Transformation was carried out by heat-shock at 42 degrees Celsius. Bacterial cells were streaked onto agar plates containing ampicillin and then colonies were expanded in LB broth. To check for insertion of the oligo sequences, Plasmid DNA was extracted from harvested bacteria cultures with the Invitrogen DNA mini prep kit. Insertion of the shRNA sequence in the lentiviral vector was verified by DNA sequencing using a specific primer for which ever promoter is used to regulate shRNA expression. The lentiviral vectors containing a correct cMyc sequence were then used to package lentiviral particles to test for their ability to knockdown FDPS. Mammalian cells were transduced with lentiviral particles either in the presence or absence of polybrene. Cells were collected after 2-4 days and protein and RNA was analyzed for cMyc expression.

Functional Assay: The effect of different cMyc shRNA targeting sequences on cMyc expression was determined by measuring mRNA expression. HepG2 hepatocellular carcinoma cells were transduced with a lentiviral vector containing cMyc shRNA sequences. After 48 hours, cells were lysed and RNA was extracted using the RNeasy mini kit from Qiagen. cDNA was then synthesized from RNA using SuperScript VILO from Invitrogen. The samples were then analyzed by quantitative PCR using an Applied Biosystems StepOne PCR machine. cMyc expression was detected with SYBR Green from Invitrogen using the forward primer (5'-GGACTATCCTGCTGCCAA-3') (SEQ ID NO: 69) and reverse primer (5'-GCCTCTTGACATTCTCCTC-3') (SEQ ID NO: 64). The samples were normalized by measuring actin expression using the forward primer (5'-AGCGCGGC-TACAGCTTCA-3') (SEQ ID NO: 61) and reverse primer (5'-GGCGACGTAGCACAGCTTCT-3') (SEQ ID NO: 62). The relative expression of cMyc was determined by its Ct value normalized to the level of actin for each sample.

Experimental Data for cMyc

The non-limiting examples of cMyc shRNA sequences depicted in Table 4 below were utilized in the experiments described herein.

TABLE 4

| cMyc shRNA sequences | | |
|---|---|---|
| Description | shRNA oligonucleotide (sense sequence - loop - antisense sequence | SEQ ID NO |
| cMyc shRNA Sequence 1 | GCTTCACCAACAGGAACTATGCTCGAGC ATAGTTCCTGTTGGTGAAGCTTTT | 10 |
| cMyc shRNA Sequence 2 | GCGAACACACAACGTCTTGGACTCGAGT CCAAGACGTTGTGTGTTCGCTTTT | 11 |
| cMyc shRNA Sequence 3 | GACATGGTGAACCAGAGTTTCCTCGAGG AAACTCTGGTTCACCATGTCTTTTT | 12 |
| cMyc shRNA Sequence 4 | GAGAATGTCAAGAGGCGAACACTCGAGT GTTCGCCTCTTGACATTCTCTTTTT | 13 |

TABLE 4-continued cMyc shRNA sequences

| Description | shRNA oligonucleotide (sense sequence - loop - antisense sequence | SEQ ID NO |
|---|---|---|
| cMyc shRNA Sequence 5 | GCTCATTTCTGAAGAGGACTTCTCGAGAAGTCCTCTTCAGAAATGAGCTTTTT | 14 |

Figure 8A:
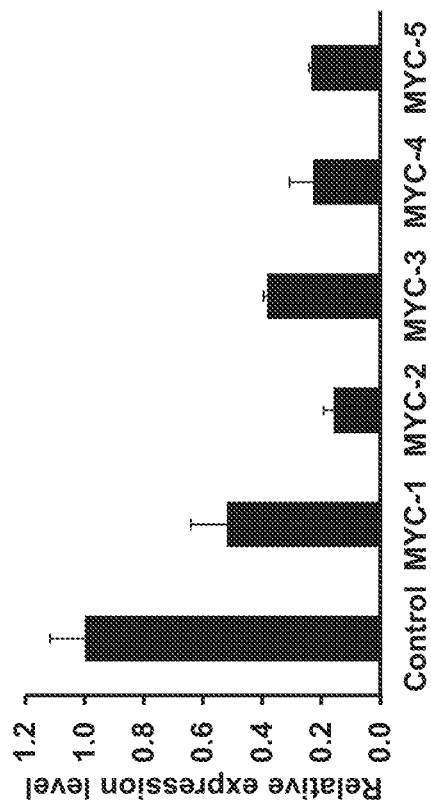
FIGS. 8A-8B depict.

As shown in FIG. 8A, the relative expression level of human cMyc following administration of the five different cMyc shRNA sequences was determined. The most significant inhibition of human cMyc expression was found in the myc-2 sample (as shown in FIG. 8A, herein).

Figure 8B:
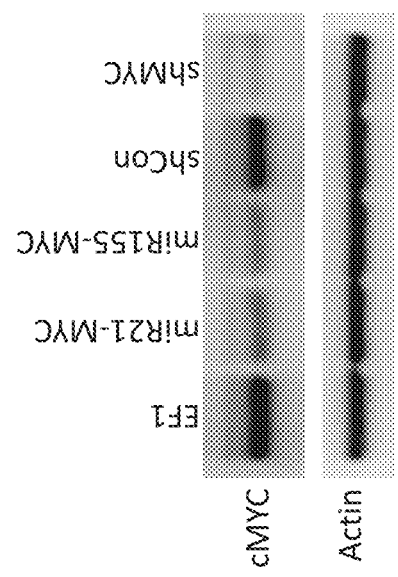

Further, as shown in FIG. 8B, SNU449 human hepatocellular carcinoma cells were infected with lentiviral vectors containing either the following miR-based cMYC sequences or a cMyc shRNA:

miR155 cMyc sequence:

(SEQ ID NO: 70)
CCTGGAGGCTTGCTGAAGGCTGTATGCTGTGTTCGCCTCTTGACATTC

CTTTTGGCCACTGACTGAGAGAATGTAGAGGCGAACACAGGACACAAG

GCCTGTTACTAGCACTCA miR21 cMyc sequence:

(SEQ ID NO: 83)
CATCTCCATGGCTGTACCACCTTGTCGGGTGTTCGCCTCTTGACATTCT

CCTGTTGAATCTCATGGAGAATGTCAAGGGCGAACACTGACATTTTGGT

ATCTTTCATCTGACCA

The above two cMyc sequences were generated using the below target sequence:
cMyc target sequence:
GAGAATGTCAAGAGGCGAACA (SEQ ID NO: 71)
cMyc shRNA sequence:
GAGAATGT-CAAGAGGCGAACACTCGAGTGTTCGCCTCTTGA-CATTCTCTTTTT (SEQ ID NO: 13)

After 48 hours, cells were lysed and an immunoblot was performed using an anti-cMyc (Santa Cruz) and an anti-actin (Sigma) antibody for a protein loading control. As shown in FIG. 8B, treatment with the cMyc shRNA significantly decreased cMyc protein expression. Treatment with the miR-based cMyc sequences also decreased cMyc expression.

Example 6. In Vivo Treatment with FDPS-shRNA and Zoledronic Acid

Protocol overview for co-administration of LV-shRNA-FDPS (farnesyl diphosphate synthase) with or without zoledronic acid in mice implanted with human prostate cancer cell line PC3. Tumor cells were cultured in vitro, then transduced with lentivirus vector control with a scrambled sequence (nonfunctional) shRNA insert and an expression cassette for firefly luciferase, or LV-FDPS with a shRNA capable of reducing expression of FDPS mRNA and an expression cassette for firefly luciferase. The transduced tumor cells were implanted on the flank of immune deficient mice by subcutaneous injection. Once tumors reached approximately 200 mm$^3$ volume, all mice receive a single dose of zoledronic acid (100 micrograms per kilogram body weight, which is similar to a standard human dose) in saline. 7 days after zoledronic acid injection, an imaging study was repeated to measure volume and photon intensity of individual tumors.

Figure 9:
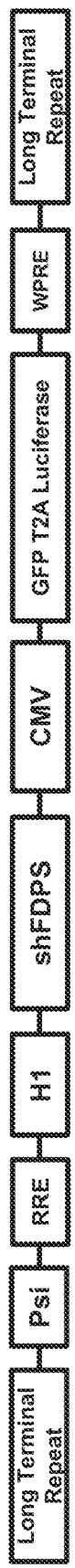
FIG. 9 depicts a linear map of a lentiviral vector encoding a FDPS shRNA targeting sequence as used in Example 6 herein.

The LV-FDPS vector designed, developed, and utilized in this Example is shown diagrammatically in FIG. 9. The LV-FDPS vector was developed using the methods and materials described herein. The following sequences were used and, as described below, a CMV GFP T2A luciferase sequence was generated and introduced into the therapeutic vector.

CMV promoter sequence:

(SEQ ID NO: 72)
ATTATGCCCAGTACATGACCTTATGGGACTTTCCTACTTGGCAGTACA

TCTACGTATTAGTCATCGCTATTACCATGGTGATGCGGTTTTGGCAGT

ACATCAATGGGCGTGGATAGCGGTTTGACTCACGGGGATTTCCAAGTC

TCCACCCCATTGACGTCAATGGGAGTTTGTTTTGGCACCAAAATCAAC

GGGACTTTCCAAAATGTCGTAACAACTCCGCCCCATTGACGCAAATGG

GCGGTAGGCGTGTACGGTGGGAGGTTTATATAAGCAGAGCTCGTTTAG

TGAACCGTCAGATCGCCTGGAGACGCCATCCACGCTGTTTT

GFP T2A Luciferase sequence:

(SEQ ID NO: 73)
ATGCCCGCCATGAAGATCGAGTGCCGCATCACCGGCACCCTGAACGGCGTGGAGTT

CGAGCTGGTGGGCGGCGGAGAGGGCACCCCCGAGCAGGGCCGCATGACCAACAAG

ATGAAGAGCACCAAAGGCGCCCTGACCTTCAGCCCCTACCTGCTGAGCCACGTGAT

GGGCTACGGCTTCTACCACTTCGGCACCTACCCCAGCGGCTACGAGAACCCCTTCCT

GCACGCCATCAACAACGGCGGCTACACCAACACCCGCATCGAGAAGTACGAGGACG

GCGGCGTGCTGCACGTGAGCTTCAGCTACCGCTACGAGGCCGGCCGCGTGATCGGC

GACTTCAAGGTGGTGGGCACCGGCTTCCCCGAGGACAGCGTGATCTTCACCGACAA

GATCATCCGCAGCAACGCCACCGTGGAGCACCTGCACCCCATGGGCGATAACGTGC

TGGTGGGCAGCTTCGCCCGCACCTTCAGCCTGCGCGACGGCGGCTACTACAGCTTCG

TGGTGGACAGCCACATGCACTTCAAGAGCGCCATCCACCCCAGCATCCTGCAGAAC

```
GGGGGCCCCATGTTCGCCTTCCGCCGCGTGGAGGAGCTGCACAGCAACACCGAGCT

GGGCATCGTGGAGTACCAGCACGCCTTCAAGACCCCCATCGCCTTCGCCAGATCTCG

AGATATCAGCCATGGCTTCCCGCCGGCGGTGGCGGCGCAGGATGATGGCACGCTGC

CCATGTCTTGTGCCCAGGAGAGCGGGATGGACCGTCACCCTGCAGCCTGTGCTTCTG

CTAGGATCAATGTGACCGGTGAGGGCAGAGGAAGTCTTCTAACATGCGGTGACGTG

GAGGAGAATCCCGGCCCTTCCGGTATGGAAGACGCCAAAAACATAAAGAAAGGCCC

GGCGCCATTCTATCCGCTAGAGGATGGAACCGCTGGAGAGCAACTGCATAAGGCTA

TGAAGAGATACGCCCTGGTTCCTGGAACAATTGCTTTTACAGATGCACATATCGAGG

TGAACATCACGTACGCGGAATACTTCGAAATGTCCGTTCGGTTGGCAGAAGCTATGA

AACGATATGGGCTGAATACAAATCACAGAATCGTCGTATGCAGTGAAAACTCTCTTC

AATTCTTTATGCCGGTGTTGGGCGCGTTATTTATCGGAGTTGCAGTTGCGCCCGCGA

ACGACATTTATAATGAACGTGAATTGCTCAACAGTATGAACATTTCGCAGCCTACCG

TAGTGTTTGTTTCCAAAAAGGGGTTGCAAAAAATTTTGAACGTGCAAAAAAAATTAC

CAATAATCCAGAAAATTATTATCATGGATTCTAAAACGGATTACCAGGGATTTCAGT

CGATGTACACGTTCGTCACATCTCATCTACCTCCCGGTTTTAATGAATACGATTTTGT

ACCAGAGTCCTTTGATCGTGACAAAACAATTGCACTGATAATGAACTCCTCTGGATC

TACTGGGTTACCTAAGGGTGTGGCCCTTCCGCATAGAACTGCCTGCGTCAGATTCTC

GCATGCCAGAGATCCTATTTTTGGCAATCAAATCATTCCGGATACTGCGATTTTAAG

TGTTGTTCCATTCCATCACGGTTTTGGAATGTTTACTACACTCGGATATTTGATATGT

GGATTTCGAGTCGTCTTAATGTATAGATTTGAAGAAGAGCTGTTTTTACGATCCCTTC

AGGATTACAAAATTCAAAGTGCGTTGCTAGTACCAACCCTATTTTCATTCTTCGCCA

AAAGCACTCTGATTGACAAATACGATTTATCTAATTTACACGAAATTGCTTCTGGGG

GCGCACCTCTTTCGAAAGAAGTCGGGGAAGCGGTTGCAAAACGCTTCCATCTTCCAG

GGATACGACAAGGATATGGGCTCACTGAGACTACATCAGCTATTCTGATTACACCCG

AGGGGGATGATAAACCGGGCGCGGTCGGTAAAGTTGTTCCATTTTTTGAAGCGAAG

GTTGTGGATCTGGATACCGGGAAAACGCTGGGCGTTAATCAGAGAGGCGAATTATG

TGTCAGAGGACCTATGATTATGTCCGGTTATGTAAACAATCCGGAAGCGACCAACGC

CTTGATTGACAAGGATGGATGGCTACATTCTGGAGACATAGCTTACTGGGACGAAG

ACGAACACTTCTTCATAGTTGACCGCTTGAAGTCTTTAATTAAATACAAAGGATACC

AGGTGGCCCCCGCTGAATTGGAGTCGATATTGTTACAACACCCCAACATCTTCGACG

CGGGCGTGGCAGGTCTTCCCGACGATGACGCCGGTGAACTTCCCGCCGCCGTTGTTG

TTTTGGAGCACGGAAAGACGATGACGGAAAAAGAGATCGTGGATTACGTCGCCAGT

CAAGTAACAACCGCGAAAAAGTTGCGCGGAGGAGTTGTGTTTGTGGACGAAGTACC

GAAAGGTCTTACCGGAAAACTCGACGCAAGAAAAATCAGAGAGATCCTCATAAAGG

CCAAGAAGGGCGGAAAGTCCAAATTGTAA
```

H1 promoter sequence:

(SEQ ID NO: 15)
```
GAACGCTGACGTCATCAACCCGCTCCAAGGAATCGCGGGCCCAGTGT

CACTAGGCGGGAACACCCAGCGCGCGTGCGCCCTGGCAGGAAGATGG

CTGTGAGGGACAGGGGAGTGGCGCCCTGCAATATTTGCATGTCGCTA

TGTGTTCTGGGAAATCACCATAAACGTGAAATGTCTTTGGATTTGGG

AATCTTATAAGTTCTGTATGAGACCACTT
```

LV FDPS GFP T2A Luc construction:

The pGF-1 plasmid (System Biosciences) containing the CMV GFP T2A luciferase sequence was digested with ClaI and KPN1 and the LV-H1-shFDPS plasmid was digested with BstBI and KpnI restriction enzymes (NEB). The DNA was electrophoresed on a 1% agarose gel and the DNA fragments were extracted with a DNA gel extraction kit (Thermo Scientific). The two fragments were ligated with T4 DNA ligase (NEB) and transformed into STBL3 bacteria (Thermo Scientific). Plasmid DNA was extracted from bacteria with a plasmid DNA mini prep kit (Thermo Scientific) and the sequence was verified by DNA sequencing (Eurofins Genomics).

Detailed Experimental Protocol:

Day −19: 175 ml flask grown confluently yields $1.87 \times 10^7$ ml of PC3 cells; 75 ml flask grown confluently yields $7.5 \times 10^6$ ml of PC3 cells.

Day −7. Thaw and grow PC3 cells

Day −4: Material Preparation and Delivery. Prepare lenti-vector control and lenti-shRNA-FDPS transduced PC3 cells.
1. In a 75 ml of flask, 50% confluent PC3 cells, add 12 μl of lenti-control+8 μl of polybrene, incubate for 5 min. then mix with 4 ml of RPMI-10, and cover the surface of PC3 cells.
2. In a 75 ml of flask, 50% confluent PC3 cell, add 20 μl of lenti-FDPS+8 μl of polybrene, incubate for 5 min. then mix with 4 ml of RPMI-10, and cover the surface of PC3 cells.
3. Incubate transduced cells at 37° C. for 8 hr. Add 6 ml of RPMI-10 for overnight culture.

Day −2: Trypsinize 75 ml transduced PC3 cells (confluent $7.5 \times 10^6$ cells) and transfer to 175 ml Flask.

Day 0: Material Preparation and Delivery
1. Trypsinize the 80% confluent lenti-vector and lenti-FDPS transduced PC3 cells separately and count cells. lenti-vector: $1.5 \times 10^8$ cells ($50 \times 3 \times 10^6/5$ ml) 15 flask lenti-FDPS: $1.5 \times 10^8$ cells ($50 \times 3 \times 10^6/5$ ml) 20 flask
2. Resuspend lenti-vector and lenti-FDPS transduced PC3 cells in RPMI without FBS, make the final concentration in $3 \times 10^6$ cells/100 μl
    Material: I) 5 ml of PC3-Lenti-vector cells (total $150 \times 10^6$ cells) in RPMI without FBS; II) 5 ml of PC3-Lenti-FDPS cells (total $150 \times 10^6$ cells) in RPMI without FBS.

Day 0: Subcutaneous injection of PC3 cells. Group I (2 NOD/SCID mice): 0.15 ml of PC3-Lenti-vector cells (0.1 mL of $3 \times 10^6$ Lenti-vector in RPMI without FBS+0.05 mL of Matrigel) are subcutaneously inoculated into either the right or left flanks of mice (total 5 ml enough for 50 mice). Group II (3 NOD/SCID mice): 0.15 ml of PC3-Lenti-FDPS KD (0.1 mL of $3 \times 10^6$ Lenti-vector in DMEM without FBS+0.05 mL of Matrigel) are subcutaneously inoculated either the right or left flanks of mice (total 5 ml enough for 50 mice).

Day 8: Monitor tumor. Tumor is palpable in the first few days after implantation. Determine tumor size by measuring the perpendicular diameters of tumor with calipers. Tumor size is calculating by following measurement: Tumor volume (mm³)=$d^2$ (d=the shortest diameter)×D/2 (D=the longest diameter). Perform bioluminescence imaging to demonstrate tumor location, size and photon intensity as a measure of lentivirus expression of the firefly luciferase gene.

Day 14: Intraperitoneal injection of 100 μg/ml of zoledronic acid (Zol) or PBS to mice when tumor size reaches 200-300 mm³.

Day 22: Imaging study to measure tumor size.

Figure 10A:
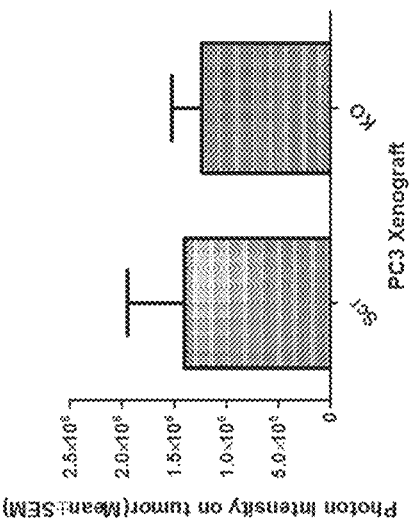
FIGS. 10A-10D depict the effect of zoledronic acid treatment of NOD/SCID mice implanted with PC3 cells transduced with LV-shFDPS or control LV as described herein.
Figure 10B:
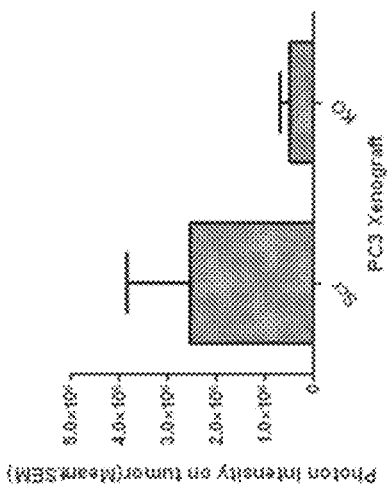

Effects of LV-shRNA-FDPS with or without zoledronic acid on PC3 tumor growth in NOD/SCID mice. Mice were designated Scr (for scrambled vector control) or KO for LV-shRNA-FDPS. LV used for this study all express the bioluminescence marker firefly luciferase to enable direct visualization of transduced cells and their growth. A bioluminescence imaging study on Day 8 determined the average tumor sizes prior to zoledronic acid treatment (FIG. 10A). The photon intensity for tumors was measured with a CCD light capture system. The average size of tumor in the Scr animals was slightly larger than was found in the KO animals (FIG. 10B) but differences were not significant.

Figure 10C:
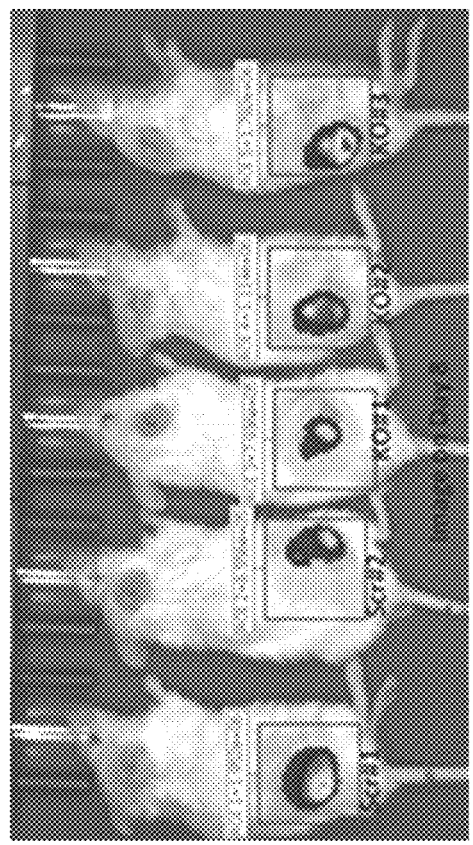
Figure 10D:
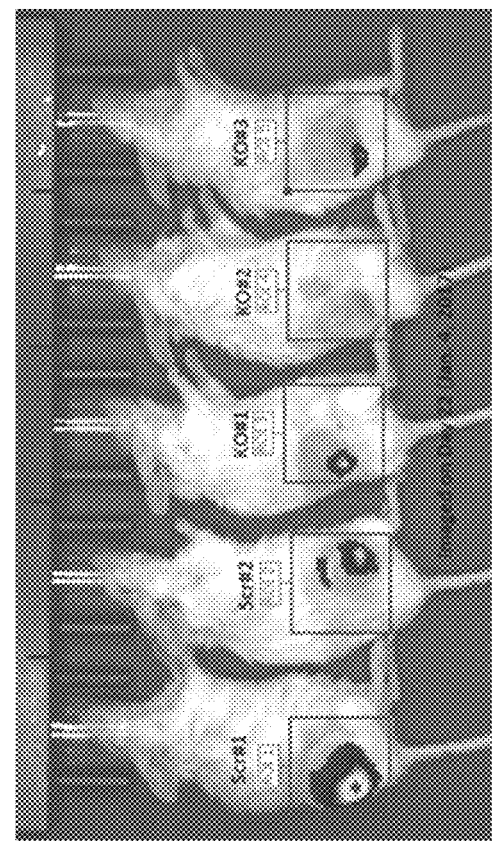

6 days after treatment with zoledronic acid (all animals received zoledronic acid by intraperitoneal injection), the imaging study was repeated. Tumor size and location for Scr animals (FIG. 10C) was similar to earlier observations but there were notable differences in tumor size for animals in the KO group. Tumor volume was reduced sharply in KO#1 and KO#3, and tumor was no longer present in KO#2. Comparing the average photon intensities for Scr and KO groups (FIG. 10D) revealed a substantial difference with the greatest change seen in the KO group.

These data show that LV-shRNA-FDPS has a small but detectable impact on growth of PC3 tumors in NOD/SCID mice. When combined with a single dose of zoledronic acid, the effect was magnified and eradication of LV-shRNA-FDPS transduced cells was achieved in one case. Thus, light-emitting transduced cells decreased by zoledronic acid only if the LV expressed a shRNA-FDPS. The reduction in tumor mass was not attributable to zoledronic acid treatment because animals with tumors transduced with scrambled control LV showed little or no change in tumor mass after zoledronic acid treatment.

The key to tumor reduction was the combined effect of LV-shRNA-FDPS reducing the levels of FDPS enzyme expression and zoledronic acid inhibiting any residual FDPS activity. As expected, the zoledronic acid was not toxic or mice and had no apparent effects other than reducing tumor mass when combined with LV-shRNA-FDPS. Zoledronic acid is a safe and effective treatment in humans where it is given in high bolus doses or as a chronic therapy for bone demineralization disorders including osteoporosis.

The disclosure of the example embodiments is intended to be illustrative, but not limiting, of the scope of the inventions, which are set forth in the following claims and their equivalents. Although example embodiments of the inventions have been described in some detail for purposes of clarity of understanding, it will be apparent that certain changes and modifications can be practiced within the scope of the following claims. In the following claims, elements and/or steps do not imply any particular order of operation, unless explicitly stated in the claims or implicitly required by the disclosure.

Sequences

The following sequences are referred to herein:

| SEQ ID NO: | Description | Sequence |
| --- | --- | --- |
| 1 | FDPS shRNA sequence #1 | GTCCTGGAGTACAATGCCATTCTCGAGAATGGCATTGTACTCCAGGACTTTTT |
| 2 | FDPS shRNA sequence #2 | GCAGGATTTCGTTCAGCACTTCTCGAGAAGTGCTGAACGAAATCCTGCTTTTT |

| SEQ ID NO: | Description | Sequence |
|---|---|---|
| 3 | FDPS shRNA sequence #3 | GCCATGTACATGGCAGGAATTCTCGAGAATTCCTGCCATG TACATGGCTTTTT |
| 4 | FDPS shRNA sequence #4 | GCAGAAGGAGGCTGAGAAAGTCTCGAGACTTTCTCAGCCT CCTTCTGCTTTTT |
| 5 | CD47 shRNA sequence #1 | GGTGAAACGATCATCGAGCCTCGAGGCTCGATGATCGTTT CACCTTTTT |
| 6 | CD47 shRNA sequence #2 | GCTACTGGCCTTGGTTTAACTCGAGTTAAACCAAGGCCAG TAGCTTTTT |
| 7 | CD47 shRNA sequence #3 | CCTCCTTCGTCATTGCCATCTCGAGATGGCAATGACGAAG GAGGTTTTT |
| 8 | CD47 shRNA sequence #4 | GCATGGCCCTCTTCTGATTCTCGAGAATCAGAAGAGGGCC ATGCTTTTT |
| 9 | CD47 shRNA sequence #5 | GGTGAAACGATCATCGAGCTACTCGAGTAGCTCGATGATC GTTTCACCTTTTT |
| 10 | cMyc shRNA sequence #1 | GCTTCACCAACAGGAACTATGCTCGAGCATAGTTCCTGTT GGTGAAGCTTTT |
| 11 | cMyc shRNA sequence #2 | GCGAACACACAACGTCTTGGACTCGAGTCCAAGACGTTGT GTGTTCGCTTTT |
| 12 | cMyc shRNA sequence #3 | GACATGGTGAACCAGAGTTTCCTCGAGGAAACTCTGGTTC ACCATGTCTTTTT |
| 13 | cMyc shRNA sequence #4 | GAGAATGTCAAGAGGCGAACACTCGAGTGTTCGCCTCTTG ACATTCTCTTTTT |
| 14 | cMyc shRNA sequence #5 | GCTCATTTCTGAAGAGGACTTCTCGAGAAGTCCTCTTCAG AAATGAGCTTTTT |
| 15 | H1 promoter | GAACGCTGACGTCATCAACCCGCTCCAAGGAATCGCGGGC CCAGTGTCACTAGGCGGGAACACCCAGCGCGCGTGCGCCC TGGCAGGAAGATGGCTGTGAGGGACAGGGGAGTGGCGCC CTGCAATATTTGCATGTCGCTATGTGTTCTGGGAAATCACC ATAAACGTGAAATGTCTTTGGATTTGGGAATCTTATAAGTT CTGTATGAGACCACTT |
| 16 | U6 promoter | GAGGGCCTATTTCCCATGATTCCTTCATATTTGCATATACG ATACAAGGCTGTTAGAGAGATAATTGGAATTAATTTGACT GTAAACACAAAGATATTAGTACAAAATACGTGACGTAGA AAGTAATAATTTCTTGGGTAGTTTGCAGTTTTAAAATTATG TTTTAAAATGGACTATCATATGCTTACCGTAACTTGAAAGT ATTTCGATTTCTTGGCTTTATATATCTTGTGGAAAGGACGA AACACC |
| 17 | 7SK promoter | CTGCAGTATTTAGCATGCCCCACCCATCTGCAAGGCATTCT GGATAGTGTCAAAACAGCCGGAAATCAAGTCCGTTTATCT CAAACTTTAGCATTTTGGGAATAAATGATATTTGCTATGCT GGTTAAATTAGATTTTAGTTAAATTTCCTGCTGAAGCTCTA GTACGATAAGCAACTTGACCTAAGTGTAAAGTTGAGATTT CCTTCAGGTTTATATAGCTTGTGCGCCGCCTGGCTACCTC |
| 18 | CAG enhancer | TAGTTATTAATAGTAATCAATTACGGGGTCATTAGTTCATA GCCCATATATGGAGTTCCGCGTTACATAACTTACGGTAAA TGGCCCGCCTGGCTGACCGCCCAACGACCCCCGCCCATTG ACGTCAATAATGACGTATGTTCCCATAGTAACGCCAATAG GGACTTTCCATTGACGTCAATGGGTGGACTATTTACGGTA AACTGCCCACTTGGCAGTACATCAAGTGTATCATATGCCA AGTACGCCCCCTATTGACGTCAATGACGGTAAATGGCCCG CCTGGCATTATGCCCAGTACATGACCTTATGGGACTTTCCT ACTTGGCAGTACATCTACGTATTAGTCATC |
| 19 | CAG promoter | GCTATTACCATGGGTCGAGGTGAGCCCCACGTTCTGCTTC ACTCTCCCCATCTCCCCCCCCTCCCCACCCCCAATTTTGTA TTTATTTATTTTTTAATTATTTTGTGCAGCGATGGGGGCGG GGGGGGGGGGCGCGCGCCAGGCGGGGCGGGGCGGGGC GAGGGGCGGGGCGGGGCGAGGCGGAGAGGTGCGGCGGCA GCCAATCAGAGCGGCGCGCTCCGAAAGTTTCCTTTTATGG CGAGGCGGCGGCGGCGGCGGCCCTATAAAAAGCGAAGCG CGCGGCGGGCG |

-continued

| SEQ ID NO: | Description | Sequence |
|---|---|---|
| 20 | chicken beta actin intron | GGAGTCGCTGCGTTGCCTTCGCCCCGTGCCCCGCTCCGCGC<br>CGCCTCGCGCCGCCCGCCCCGGCTCTGACTGACCGCGTTA<br>CTCCCACAGGTGAGCGGGCGGGACGGCCCTTCTCCTCCGG<br>GCTGTAATTAGCGCTTGGTTTAATGACGGCTCGTTTCTTTT<br>CTGTGGCTGCGTGAAAGCCTTAAAGGGCTCCGGGAGGGCC<br>CTTTGTGCGGGGGGAGCGGCTCGGGGGGTGCGTGCGTGT<br>GTGTGTGCGTGGGGAGCGCCGCGTGCGGCCCGCGCTGCCC<br>GGCGGCTGTGAGCGCTGCGGGCGCGGCGCGGGGCTTTGTG<br>CGCTCCGCGTGTGCGCGAGGGGAGCGCGGCCGGGGGCGG<br>TGCCCCGCGGTGCGGGGGGGCTGCGAGGGGAACAAAGGC<br>TGCGTGCGGGGTGTGTGCGTGGGGGGGTGAGCAGGGGGT<br>GTGGGCGCGGCGGTCGGGCTGTAACCCCCCCCTGCACCCC<br>CCTCCCCGAGTTGCTGAGCACGGCCCGGCTTCGGGTGCGG<br>GGCTCCGTGCGGGGCGTGGCGCGGGGCTCGCCGTGCCGGG<br>CGGGGGGTGGCGGCAGGTGGGGGTGCCGGGCGGGGCGGG<br>GCCGCCTCGGGCCGGGGAGGGCTCGGGGGAGGGGCGCGG<br>CGGCCCCGGAGCGCCGGCGGCTGTCGAGGCGCGGCGAGC<br>CGCAGCCATTGCCTTTTATGGTAATCGTGCGAGAGGGCGC<br>AGGGACTTCCTTTGTCCCAAATCTGGCGGAGCCGAAATCT<br>GGGAGGCGCCGCCGCACCCCCTCTAGCGGGCGCGGGCGA<br>AGCGGTGCGGCGCCGGCAGGAAGGAAATGGGCGGGGAGG<br>GCCTTCGTGCGTCGCCGCGCCGCCGTCCCCTTCTCCATCTC<br>CAGCCTCGGGGCTGCCGCAGGGGGACGGCTGCCTTCGGGG<br>GGGACGGGGCAGGGCGGGGTTCGGCTTCTGGCGTGTGACC<br>GGCGG |
| 21 | HIV gag | ATGGGTGCGAGAGCGTCAGTATTAAGCGGGGGAGAATTA<br>GATCGATGGGAAAAAATTCGGTTAAGGCCAGGGGGAAAG<br>AAAAAATATAAATTAAAACATATAGTATGGGCAAGCAGG<br>GAGCTAGAACGATTCGCAGTTAATCCTGGCCTGTTAGAAA<br>CATCAGAAGGCTGTAGACAAATACTGGGACAGCTACAACC<br>ATCCCTTCAGACAGGATCAGAAGAACTTAGATCATTATAT<br>AATACAGTAGCAACCCTCTATTGTGTGCATCAAAGGATAG<br>AGATAAAAGACACCAAGGAAGCTTTAGACAAGATAGAGG<br>AAGAGCAAAACAAAAGTAAGAAAAAAGCACAGCAAGCA<br>GCAGCTGACACAGGACACAGCAATCAGGTCAGCCAAAAT<br>TACCCTATAGTGCAGAACATCCAGGGGCAAATGGTACATC<br>AGGCCATATCACCTAGAACTTTAAATGCATGGGTAAAAGT<br>AGTAGAAGAGAAGGCTTTCAGCCCAGAAGTGATACCCATG<br>TTTTCAGCATTATCAGAAGGAGCCACCCCACAAGATTTAA<br>ACACCATGCTAAACACAGTGGGGGGACATCAAGCAGCCA<br>TGCAAATGTTAAAAGAGACCATCAATGAGGAAGCTGCAG<br>AATGGGATAGAGTGCATCCAGTGCATGCAGGGCCTATTGC<br>ACCAGGCCAGATGAGAGAACCAAGGGGAAGTGACATAGC<br>AGGAACTACTAGTACCCTTCAGGAACAAATAGGATGGATG<br>ACACATAATCCACCTATCCCAGTAGGAGAAATCTATAAAA<br>GATGGATAATCCTGGGATTAAATAAAATAGTAAGAATGTA<br>TAGCCCTACCAGCATTCTGGACATAAGACAAGGACCAAAG<br>GAACCCTTTAGAGACTATGTAGACCGATTCTATAAAACTC<br>TAAGAGCCGAGCAAGCTTCACAAGAGGTAAAAAATTGGA<br>TGACAGAAACCTTGTTGGTCCAAAATGCGAACCCAGATTG<br>TAAGACTATTTTAAAAGCATTGGGACCAGGAGCGACACTA<br>GAAGAAATGATGACAGCATGTCAGGGAGTGGGGGGACCC<br>GGCCATAAAGCAAGAGTTTTGGCTGAAGCAATGAGCCAA<br>GTAACAAATCCAGCTACCATAATGATACAGAAAGGCAATT<br>TTAGGAACCAAAGAAAGACTGTTAAGTGTTTCAATTGTGG<br>CAAAGAAGGGCACATAGCCAAAAATTGCAGGGCCCCTAG<br>GAAAAAGGGCTGTTGGAAATGTGGAAAGGAAGGACACCA<br>AATGAAAGATTGTACTGAGAGACAGGCTAATTTTTTAGGG<br>AAGATCTGGCCTTCCCACAAGGGAAGGCCAGGGAATTTTC<br>TTCAGAGCAGACCAGAGCCAACAGCCCCACCAGAAGAGA<br>GCTTCAGGTTTGGGGAAGAGACAACAACTCCCTCTCAGAA<br>GCAGGAGCCGATAGACAAGGAACTGTATCCTTTAGCTTCC<br>CTCAGATCACTCTTTGGCAGCGACCCCTCGTCACAATAA |
| 22 | HIV Pol | ATGAATTTGCCAGGAAGATGGAAACCAAAAATGATAGGG<br>GGAATTGGAGGTTTTATCAAAGTAGGACAGTATGATCAGA<br>TACTCATAGAAATCTGCGGACATAAAGCTATAGGTACAGT<br>ATTAGTAGGACCTACACCTGTCAACATAATTGGAAGAAAT<br>CTGTTGACTCAGATTGGCTGCACTTTAAATTTTCCCATTAG<br>TCCTATTGAGACTGTACCAGTAAAATTAAAGCCAGGAATG<br>GATGGCCCAAAAGTTAAACAATGGCCATTGACAGAAGAA<br>AAAATAAAAGCATTAGTAGAAATTTGTACAGAAATGGAA<br>AAGGAAGGAAAATTTCAAAAATTGGGCCTGAAAATCCA<br>TACAATACTCCAGTATTTGCCATAAAGAAAAAAGACAGTA<br>CTAAATGGAGAAAATTAGTAGATTTCAGAGAACTTAATAA |

| SEQ ID NO: | Description | Sequence |
|---|---|---|
| | | GAGAACTCAAGATTTCTGGGAAGTTCAATTAGGAATACCA
CATCCTGCAGGGTTAAAACAGAAAAAATCAGTAACAGTAC
TGGATGTGGGCGATGCATATTTTTCAGTTCCCTTAGATAAA
GACTTCAGGAAGTATACTGCATTTACCATACCTAGTATAA
ACAATGAGACACCAGGGATTAGATATCAGTACAATGTGCT
TCCACAGGGATGGAAAGGATCACCAGCAATATTCCAGTGT
AGCATGACAAAAATCTTAGAGCCTTTTAGAAAACAAAATC
CAGACATAGTCATCTATCAATACATGGATGATTTGTATGT
AGGATCTGACTTAGAAATAGGGCAGCATAGAACAAAAAT
AGAGGAACTGAGACAACATCTGTTGAGGTGGGGATTTACC
ACACCAGACAAAAAACATCAGAAAGAACCTCCATTCCTTT
GGATGGGTTATGAACTCCATCCTGATAAATGGACAGTACA
GCCTATAGTGCTGCCAGAAAAGGACAGCTGGACTGTCAAT
GACATACAGAAATTAGTGGGAAAATTGAATTGGGCAAGTC
AGATTTATGCAGGGATTAAAGTAAGGCAATTATGTAAACT
TCTTAGGGGAACCAAAGCACTAACAGAAGTAGTACCACTA
ACAGAAGAAGCAGAGCTAGAACTGGCAGAAAACAGGGAG
ATTCTAAAAGAACCGGTACATGGAGTGTATTATGACCCAT
CAAAAGACTTAATAGCAGAAATACAGAAGCAGGGGCAAG
GCCAATGGACATATCAAATTTATCAAGAGCCATTTAAAAA
TCTGAAAACAGGAAAATATGCAAGAATGAAGGGTGCCCA
CACTAATGATGTGAAACAATTAACAGAGGCAGTACAAAA
AATAGCCACAGAAAGCATAGTAATATGGGGAAAGACTCC
TAAATTTAAATTACCCATACAAAAGGAAACATGGGAAGCA
TGGTGGACAGAGTATTGGCAAGCCACCTGGATTCCTGAGT
GGGAGTTTGTCAATACCCCTCCCTTAGTGAAGTTATGGTAC
CAGTTAGAGAAAGAACCCATAATAGGAGCAGAAACTTTCT
ATGTAGATGGGGCAGCCAATAGGGAAACTAAATTAGGAA
AAGCAGGATATGTAACTGACAGAGGAAGACAAAAAGTTG
TCCCCCTAACGGACACAACAAATCAGAAGACTGAGTTACA
AGCAATTCATCTAGCTTTGCAGGATTCGGGATTAGAAGTA
AACATAGTGACAGACTCACAATATGCATTGGGAATCATTC
AAGCACAACCAGATAAGAGTGAATCAGAGTTAGTCAGTC
AAATAATAGAGCAGTTAATAAAAAAGGAAAAAGTCTACC
TGGCATGGGTACCAGCACACAAAGGAATTGGAGGAAATG
AACAAGTAGATGGGTTGGTCAGTGCTGGAATCAGGAAAGT
ACTA |
| 23 | HIV Int | TTTTTAGATGGAATAGATAAGGCCCAAGAAGAACATGAGA
AATATCACAGTAATTGGAGAGCAATGGCTAGTGATTTTAA
CCTACCACCTGTAGTAGCAAAAGAAATAGTAGCCAGCTGT
GATAAATGTCAGCTAAAAGGGGAAGCCATGCATGGACAA
GTAGACTGTAGCCCAGGAATATGGCAGCTAGATTGTACAC
ATTTAGAAGGAAAAGTTATCTTGGTAGCAGTTCATGTAGC
CAGTGGATATATAGAAGCAGAAGTAATTCCAGCAGAGAC
AGGGCAAGAAACAGCATACTTCCTCTTAAAATTAGCAGGA
AGATGGCCAGTAAAAACAGTACATACAGACAATGGCAGC
AATTTCACCAGTACTACAGTTAAGGCCGCCTGTTGGTGGG
CGGGGATCAAGCAGGAATTTGGCATTCCCTACAATCCCCA
AAGTCAAGGAGTAATAGAATCTATGAATAAAGAATTAAA
GAAAATTATAGGACAGGTAAGAGATCAGGCTGAACATCTT
AAGACAGCAGTACAAATGGCAGTATTCATCCACAATTTTA
AAAGAAAAGGGGGGATTGGGGGGTACAGTGCAGGGGAAA
GAATAGTAGACATAATAGCAACAGACATACAAACTAAAG
AATTACAAAAACAATTACAAAAATTCAAAATTTTCGGGT
TTATTACAGGGACAGCAGAGATCCAGTTTGGAAAGGACCA
GCAAAGCTCCTCTGGAAAGGTGAAGGGGCAGTAGTAATA
CAAGATAATAGTGACATAAAAGTAGTGCCAAGAAGAAAA
GCAAAGATCATCAGGGATTATGGAAAACAGATGGCAGGT
GATGATTGTGTGGCAAGTAGACAGGATGAGGATTAA |
| 24 | HIV RRE | AGGAGCTTTGTTCCTTGGGTTCTTGGGAGCAGCAGGAAGC
ACTATGGGCGCAGCGTCAATGACGCTGACGGTACAGGCCA
GACAATTATTGTCTGGTATAGTGCAGCAGCAGAACAATTT
GCTGAGGGCTATTGAGGCGCAACAGCATCTGTTGCAACTC
ACAGTCTGGGGCATCAAGCAGCTCCAGGCAAGAATCCTGG
CTGTGGAAAGATACCTAAAGGATCAACAGCTCCT |
| 25 | HIV Rev | ATGGCAGGAAGAAGCGGAGACAGCGACGAAGAACTCCTC
AAGGCAGTCAGACTCATCAAGTTTCTCTATCAAAGCAACC
CACCTCCCAATCCCGAGGGGACCCGACAGGCCCGAAGGA
ATAGAAGAAGAAGGTGGAGAGAGAGACAGAGACAGATCC
ATTCGATTAGTGAACGGATCCTTAGCACTTATCTGGGACG
ATCTGCGGAGCCTGTGCCTCTTCAGCTACCACCGCTTGAG
AGACTTACTCTTGATTGTAACGAGGATTGTGGAACTTCTG
GGACGCAGGGGGTGGGAAGCCCTCAAATATTGGTGGAAT
CTCCTACAATATTGGAGTCAGGAGCTAAAGAATAG |

| SEQ ID NO: | Description | Sequence |
| --- | --- | --- |
| 26 | rabbit beta globin poly A | AGATCTTTTTCCCTCTGCCAAAAATTATGGGGACATCATGA AGCCCCTTGAGCATCTGACTTCTGGCTAATAAAGGAAATT TATTTTCATTGCAATAGTGTGTTGGAATTTTTTGTGTCTCTC ACTCGGAAGGACATATGGGAGGGCAAATCATTTAAAACAT CAGAATGAGTATTTGGTTTAGAGTTTGGCAACATATGCCA TATGCTGGCTGCCATGAACAAAGGTGGCTATAAAGAGGTC ATCAGTATATGAAACAGCCCCCTGCTGTCCATTCCTTATTC CATAGAAAAGCCTTGACTTGAGGTTAGATTTTTTTTATATT TTGTTTTGTGTTATTTTTTCTTTAACATCCCTAAAATTTTC CTTACATGTTTTACTAGCCAGATTTTCCTCCTCTCCTGACT ACTCCCAGTCATAGCTGTCCCTCTTCTCTTATGAAGATC |
| 27 | CMV Promoter | ACATTGATTATTGACTAGTTATTAATAGTAATCAATTACGG GGTCATTAGTTCATAGCCCATATATGGAGTTCCGCGTTACA TAACTTACGGTAAATGGCCCGCCTGGCTGACCGCCCAACG ACCCCCGCCCATTGACGTCAATAATGACGTATGTTCCCAT AGTAACGCCAATAGGGACTTTCCATTGACGTCAATGGGTG GAGTATTTACGGTAAACTGCCCACTTGGCAGTACATCAAG TGTATCATATGCCAAGTACGCCCCCTATTGACGTCAATGA CGGTAAATGGCCCGCCTGGCATTATGCCCAGTACATGACC TTATGGGACTTTCCTACTTGGCAGTACATCTACGTATTAGT CATCGCTATTACCATGGTGATGCGGTTTTGGCAGTACATCA ATGGGCGTGGATAGCGGTTTGACTCACGGGGATTTCCAAG TCTCCACCCCATTGACGTCAATGGGAGTTTGTTTTGGCACC AAAATCAACGGGACTTTCCAAAATGTCGTAACAACTCCGC CCCATTGACGCAAATGGGCGGTAGGCGTGTACGGTGGGAG GTCTATATAAGC |
| 28 | beta globin intron | GTGAGTTTGGGGACCCTTGATTGTTCTTTCTTTTTCGCTATT GTAAAATTCATGTTATATGGAGGGGGCAAAGTTTTCAGGG TGTTGTTTAGAATGGGAAGATGTCCCTTGTATCACCATGG ACCCTCATGATAATTTTGTTTCTTTCACTTTCTACTCTGTTG ACAACCATTGTCTCCTCTTATTTTCTTTTCATTTTCTGTAAC TTTTTCGTTAAACTTTAGCTTGCATTTGTAACGAATTTTTA AATTCACTTTTGTTTATTTGTCAGATTGTAAGTACTTTCTCT AATCACTTTTTTTTCAAGGCAATCAGGGTATATTATATTGT ACTTCAGCACAGTTTTAGAGAACAATTGTTATAATTAAAT GATAAGGTAGAATATTTCTGCATATAAATTCTGGCTGGCG TGGAAATATTCTTATTGGTAGAAACAACTACACCCTGGTC ATCATCCTGCCTTTCTCTTTATGGTTACAATGATATACACT GTTTGAGATGAGGATAAAATACTCTGAGTCCAAACCGGGC CCCTCTGCTAACCATGTTCATGCCTTCTTCTCTTTCCTACAG |
| 29 | VSV-G/DNA fragment containing VSV-G | GAATTCATGAAGTGCCTTTTGTACTTAGCCTTTTTATTCAT TGGGGTGAATTGCAAGTTCACCATAGTTTTTCCACACAAC CAAAAAGGAAACTGGAAAAATGTTCCTTCTAATTACCATT ATTGCCCGTCAAGCTCAGATTTAAATTGGCATAATGACTT AATAGGCACAGCCTTACAAGTCAAAATGCCCAAGAGTCAC AAGGCTATTCAAGCAGACGGTTGGATGTGTCATGCTTCCA AATGGGTCACTACTTGTGATTTCCGCTGGTATGGACCGAA GTATATAACACATTCCATCCGATCCTTCACTCCATCTGTAG AACAATGCAAGGAAAGCATTGAACAAACGAAACAAGGAA CTTGGCTGAATCCAGGCTTCCCTCCTCAAAGTTGTGGATAT GCAACTGTGACGGATGCCGAAGCAGTGATTGTCCAGGTGA CTCCTCACCATGTGCTGGTTGATGAATACACAGGAGAATG GGTTGATTCACAGTTCATCAACGGAAAATGCAGCAATTAC ATATGCCCCACTGTCCATAACTCTACAACCTGGCATTCTGA CTATAAGGTCAAAGGGCTATGTGATTCTAACCTCATTTCCA TGGACATCACCTTCTTCTCAGAGGACGGAGAGCTATCATC CCTGGGAAAGGAGGGCACAGGGTTCAGAAGTAACTACTTT GCTTATGAAACTGGAGGCAAGGCCTGCAAAATGCAATACT GCAAGCATTGGGGAGTCAGACTCCCATCAGGTGTCTGGTT CGAGATGGCTGATAAGGATCTCTTTGCTGCAGCCAGATTC CCTGAATGCCCAGAAGGGTCAAGTATCTCTGCTCCATCTC AGACCTCAGTGGATGTAAGTCTAATTCAGGACGTTGAGAG GATCTTGGATTATTCCCTCTGCCAAGAAACCTGGAGCAAA ATCAGAGCGGGTCTTCCAATCTCTCCAGTGGATCTCAGCT ATCTTGCTCCTAAAAACCCAGGAACCGGTCCTGCTTTCACC ATAATCAATGGTACCCTAAAATACTTTGAGACCAGATACA TCAGAGTCGATATTGCTGCTCCAATCCTCTCAAGAATGGTC GGAATGATCAGTGGAACTACCACAGAAAGGGAACTGTGG GATGACTGGGCACCATATGAAGACGTGGAAATTGGACCCA ATGGAGTTCTGAGGACCAGTTCAGGATATAAGTTTCCTTT ATACATGATTGGACATGGTATGTTGGACTCCGATCTTCATC TTAGCTCAAAGGCTCAGGTGTTCGAACATCCTCACATTCA AGACGCTGCTTCGCAACTTCCTGATGATGAGAGTTTATTTT |

| SEQ ID NO: | Description | Sequence |
|---|---|---|
| | | TTGGTGATACTGGGCTATCCAAAAATCCAATCGAGCTTGT<br>AGAAGGTTGGTTCAGTAGTTGGAAAAGCTCTATTGCCTCT<br>TTTTTCTTTATCATAGGGTTAATCATTGGACTATTCTTGGTT<br>CTCCGAGTTGGTATCCATCTTTGCATTAAATTAAAGCACAC<br>CAAGAAAAGACAGATTTATACAGACATAGAGATGAGAAT<br>TC |
| 30 | rabbit beta globin poly A | AGATCTTTTTCCCTCTGCCAAAAATTATGGGGACATCATGA<br>AGCCCCTTGAGCATCTGACTTCTGGCTAATAAAGGAAATT<br>TATTTTCATTGCAATAGTGTGTTGGAATTTTTTGTGTCTCTC<br>ACTCGGAAGGACATATGGGAGGGCAAATCATTTAAAACAT<br>CAGAATGAGTATTTGGTTTAGAGTTTGGCAACATATGCCC<br>ATATGCTGGCTGCCATGAACAAAGGTTGGCTATAAAGAGG<br>TCATCAGTATATGAAACAGCCCCTGCTGTCCATTCCTTAT<br>TCCATAGAAAAGCCTTGACTTGAGGTTAGATTTTTTTATA<br>TTTTGTTTTGTGTTATTTTTTCTTTAACATCCCTAAAATTT<br>TCCTTACATGTTTTACTAGCCAGATTTTTCCTCCTCTCCTGA<br>CTACTCCCAGTCATAGCTGTCCCTCTTCTCTTATGGAGATC |
| 31 | Primer | TAAGCAGAATTCATGAATTTGCCAGGAAGAT |
| 32 | Primer | CCATACAATGAATGGACACTAGGCGGCCGCACGAAT |
| 33 | Gag, Pol, Integrase fragment | GAATTCATGAATTTGCCAGGAAGATGGAAACCAAAAATG<br>ATAGGGGGAATTGGAGGTTTTATCAAAGTAAGACAGTATG<br>ATCAGATACTCATAGAAATCTGCGGACATAAAGCTATAGG<br>TACAGTATTAGTAGGACCTACACCTGTCAACATAATTGGA<br>AGAAATCTGTTGACTCAGATTGGCTGCACTTTAAATTTTCC<br>CATTAGTCCTATTGAGACTGTACCAGTAAAATTAAAGCCA<br>GGAATGGATGGCCCAAAAGTTAAACAATGGCCATTGACA<br>GAAGAAAAAATAAAAGCATTAGTAGAAATTTGTACAGAA<br>ATGGAAAAGGAAGGAAAAATTTCAAAAATTGGGCCTGAA<br>AATCCATACAATACTCCAGTATTTGCCATAAAGAAAAAAG<br>ACAGTACTAAATGGAGAAAATTAGTAGATTTCAGAGAACT<br>TAATAAGAGAACTCAAGATTTCTGGGAAGTTCAATTAGGA<br>ATACCACATCCTGCAGGGTTAAAACAGAAAAAATCAGTAA<br>CAGTACTGGATGTGGGCGATGCATATTTTTCAGTTCCCTTA<br>GATAAAGACTTCAGGAAGTATACTGCATTTACCATACCTA<br>GTATAAACAATGAGACACCAGGGATTAGATATCAGTACAA<br>TGTGCTTCCACAGGGATGGAAAGGATCACCAGCAATATTC<br>CAGTGTAGCATGACAAAAATCTTAGAGCCTTTTAGAAAAC<br>AAAATCCAGACATAGTCATCTATCAATACATGGATGATTT<br>GTATGTAGGATCTGACTTAGAAATAGGGCAGCATAGAACA<br>AAAATAGAGGAACTGAGACAACATCTGTTGAGGTGGGGA<br>TTTACCACACCAGACAAAAAACATCAGAAAGAACCTCCAT<br>TCCTTTGGATGGGTTATGAACTCCATCCTGATAAATGGAC<br>AGTACAGCCTATAGTGCTGCCAGAAAAGGACAGCTGGACT<br>GTCAATGACATACAGAAATTAGTGGGAAAATTGAATTGGG<br>CAAGTCAGATTTATGCAGGGATTAAAGTAAGGCAATTATG<br>TAAACTTCTTAGGGGAACCAAAGCACTAACAGAAGTAGTA<br>CCACTAACAGAAGAAGCAGAGCTAGAACTGGCAGAAAAC<br>AGGGAGATTCTAAAAGAACCGGTACATGGAGTGTATTATG<br>ACCCATCAAAAGACTTAATAGCAGAAATACAGAAGCAGG<br>GGCAAGGCCAATGGACATATCAAATTTATCAAGAGCCATT<br>TAAAAATCTGAAAACAGGAAAGTATGCAAGAATGAAGGG<br>TGCCCACACTAATGATGTGAAACAATTAACAGAGGCAGTA<br>CAAAAAATAGCCACAGAAAGCATAGTAATATGGGGAAAG<br>ACTCCTAAATTTAAATTACCCATACAAAAGGAAACATGGG<br>AAGCATGGTGGACAGAGTATTGGCAAGCCACCTGGATTCC<br>TGAGTGGGAGTTTGTCAATACCCCTCCCTTAGTGAAGTTAT<br>GGTACCAGTTAGAGAAAGAACCCATAATAGGAGCAGAAA<br>CTTTCTATGTAGATGGGGCAGCCAATAGGGAAACTAAATT<br>AGGAAAAGCAGGATATGTAACTGACAGAGGAAGACAAAA<br>AGTTGTCCCCCTAACGGACACAACAAATCAGAAGACTGAG<br>TTACAAGCAATTCATCTAGCTTTGCAGGATTCGGGATTAG<br>AAGTAAACATAGTGACAGACTCACAATATGCATTGGGAAT<br>CATTCAAGCACAACCAGATAAGAGTGAATCAGAGTTAGTC<br>AGTCAAATAATAGAGCAGTTAATAAAAAAGGAAAAAGTC<br>TACCTGGCATGGGTACCAGCACACAAAGGAATTGGAGGA<br>AATGAACAAGTAGATAAATTGGTCAGTGCTGGAATCAGGA<br>AAGTACTATTTTTAGATGGAATAGATAAGGCCCAAGAAGA<br>ACATGAGAAATATCACAGTAATTGGAGAGCAATGGCTAGT<br>GATTTTAACCTACCACCTGTAGTAGCAAAGAAATAGTAG<br>CCAGCTGTGATAAATGTCAGCTAAAAGGGGAAGCCATGCA<br>TGGACAAGTAGACTGTAGCCCAGGAATATGGCAGCTAGAT<br>TGTACACATTTAGAAGGAAAAGTTATCTTGGTAGCAGTTC<br>ATGTAGCCAGTGGATATATAGAAGCAGAAGTAATTCCAGC<br>AGAGACAGGGCAAGAAACAGCATACTTCCTCTTAAAATTA |

| SEQ ID NO: | Description | Sequence |
|---|---|---|
| | | GCAGGAAGATGGCCAGTAAAAACAGTACATACAGACAAT<br>GGCAGCAATTTCACCAGTACTACAGTTAAGGCCGCCTGTT<br>GGTGGGCGGGGATCAAGCAGGAATTTGGCATTCCCTACAA<br>TCCCCAAAGTCAAGGAGTAATAGAATCTATGAATAAAGAA<br>TTAAAGAAAATTATAGGACAGGTAAGAGATCAGGCTGAA<br>CATCTTAAGACAGCAGTACAAATGGCAGTATTCATCCACA<br>ATTTTAAAAGAAAAGGGGGGATTGGGGGGTACAGTGCAG<br>GGGAAGAATAGTAGACATAATAGCAACAGACATACAAA<br>CTAAAGAATTACAAAAACAATTACAAAAATTCAAAATTT<br>TCGGGTTTATTACAGGGACAGCAGAGATCCAGTTTGGAAA<br>GGACCAGCAAAGCTCCTCTGGAAAGGTGAAGGGGCAGTA<br>GTAATACAAGATAATAGTGACATAAAAGTAGTGCCAAGA<br>AGAAAAGCAAAGATCATCAGGGATTATGGAAAACAGATG<br>GCAGGTGATGATTGTGTGGCAAGTAGACAGGATGAGGATT<br>AA |
| 34 | DNA Fragment containing Rev, RRE and rabbit beta globin poly A | TCTAGAATGGCAGGAAGAAGCGGAGACAGCGACGAAGAG<br>CTCATCAGAACAGTCAGACTCATCAAGCTTCTCTATCAAA<br>GCAACCCACCTCCCAATCCCGAGGGGACCCGACAGGCCCG<br>AAGGAATAGAAGAAGAAGGTGGAGAGAGAGACAGAGAC<br>AGATCCATTCGATTAGTGAACGGATCCTTGGCACTTATCTG<br>GGACGATCTGCGGAGCCTGTGCCTCTTCAGCTACCACCGC<br>TTGAGAGACTTACTCTTGATTGTAACGAGGATTGTGGAAC<br>TTCTGGGACGCAGGGGGTGGGAAGCCCTCAAATATTGGTG<br>GAATCTCCTACAATATTGGAGTCAGGAGCTAAAGAATAGA<br>GGAGCTTTGTTCCTTGGGTTCTTGGGAGCAGCAGGAAGCA<br>CTATGGGCGCAGCGTCAATGACGCTGACGGTACAGGCCAG<br>ACAATTATTGTCTGGTATAGTGCAGCAGCAGAACAATTTG<br>CTGAGGGCTATTGAGGCGCAACAGCATCTGTTGCAACTCA<br>CAGTCTGGGGCATCAAGCAGCTCCAGGCAAGAATCCTGGC<br>TGTGGAAAGATACCTAAAGGATCAACAGCTCCTAGATCTT<br>TTTCCCTCTGCCAAAAATTATGGGGACATCATGAAGCCCC<br>TTGAGCATCTGACTTCTGGCTAATAAAGGAAATTTATTTTC<br>ATTGCAATAGTGTGTTGGAATTTTTTGTGTCTCTCACTCGG<br>AAGGACATATGGGAGGGCAAATCATTTAAAACATCAGAA<br>TGAGTATTTGGTTTAGAGTTTGGCAACATATGCCATATGCT<br>GGCTGCCATGAACAAAGGTGGCTATAAAGAGGTCATCAGT<br>ATATGAAACAGCCCCCTGCTGTCCATTCCTTATTCCATAGA<br>AAAGCCTTGACTTGAGGTTAGATTTTTTTTATATTTTGTTTT<br>GTGTTATTTTTTCTTTAACATCCCTAAAATTTTCCTTACAT<br>GTTTTACTAGCCAGATTTTTCCTCCTCTCCTGACTACTCCC<br>AGTCATAGCTGTCCCTCTTCTCTTATGAAGATCCCTCGACC<br>TGCAGCCCAAGCTTGGCGTAATCATGGTCATAGCTGTTTCC<br>TGTGTGAAATTGTTATCCGCTCACAATTCCACACAACATAC<br>GAGCCGGAAGCATAAAGTGTAAAGCCTGGGGTGCCTAAT<br>GAGTGAGCTAACTCACATTAATTGCGTTGCGCTCACTGCC<br>CGCTTTCCAGTCGGGAAACCTGTCGTGCCAGCGGATCCGC<br>ATCTCAATTAGTCAGCAACCATAGTCCCGCCCCTAACTCC<br>GCCCATCCCGCCCCTAACTCCGCCCAGTTCCGCCCATTCTC<br>CGCCCCATGGCTGACTAATTTTTTTTATTTATGCAGAGGCC<br>GAGGCCGCCTCGGCCTCTGAGCTATTCCAGAAGTAGTGAG<br>GAGGCTTTTTTGGAGGCCTAGGCTTTTGCAAAAAGCTAAC<br>TTGTTTATTGCAGCTTATAATGGTTACAAATAAAGCAATA<br>GCATCACAAATTTCACAAATAAAGCATTTTTTTCACTGCAT<br>TCTAGTTGTGGTTTGTCCAAACTCATCAATGTATCTTATCA<br>GCGGCCGCCCCGGG |
| 35 | DNA fragment containing the enhancer/promoter/intron sequence | ACGCGTTAGTTATTAATAGTAATCAATTACGGGGTCATTA<br>GTTCATAGCCCATATATGGAGTTCCGCGTTACATAACTTAC<br>CAGGGTAAATGGCCCGCCTGGCTGACCGCCCAACGACCCCCGC<br>CCATTGACGTCAATAATGACGTATGTTCCCATAGTAACGC<br>CAATAGGGACTTTCCATTGACGTCAATGGGTGGACTATTT<br>ACGGTAAACTGCCCACTTGGCAGTACATCAAGTGTATCAT<br>ATGCCAAGTACGCCCCCTATTGACGTCAATGACGGTAAAT<br>GGCCCGCCTGGCATTATGCCCAGTACATGACCTTATGGGA<br>CTTTCCTACTTGGCAGTACATCTACGTATTAGTCATCGCTA<br>TTACCATGGGTCGAGGTGAGCCCCACGTTCTGCTTCACTCT<br>CCCCATCTCCCCCCCCTCCCCACCCCCAATTTTGTATTTATT<br>TATTTTTTAATTATTTTGTGCAGCGATGGGGGCGGGGGG<br>GGGGGGGCGCGCGCCAGGCGGGGCGGGGCGGGGCGAGGG<br>GCGGGGCGGGGCGAGGCGGAGAGGTGCGGCGGCAGCCAA<br>TCAGAGCGGCGCGCTCCGAAAGTTTCCTTTTATGGCGAGG<br>CGGCGCGGCGGCGGCCCTATAAAAAGCGAAGCGCGCGG<br>CGGGCGGGAGTCGCTGCGTTGCCTTCGCCCCGTGCCCCGC<br>TCCGCGCCGCCTCGCGCCGCCCGCCCCGGCTCTGACTGAC<br>CGCGTTACTCCCACAGGTGAGCGGGCGGGACGGCCCTTCT<br>CCTCCGGGCTGTAATTAGCGCTTGGTTTAATGACGGCTCGT |

| SEQ ID NO: | Description | Sequence |
|---|---|---|
| | | TTCTTTTCTGTGGCTGCGTGAAAGCCTTAAAGGGCTCCGGG<br>AGGGGCCCTTTGTGCGGGGGGGAGCGGCTCGGGGGGTGCGT<br>GCGTGTGTGTGTGCGTGGGGAGCGCCGCGTGCGGCCCGCG<br>CTGCCCGGCGGCTGTGAGCGCTGCGGGCGCGGCGCGGGC<br>TTTGTGCGCTCCGCGTGTGCGCGAGGGGAGCGCGGCCGGG<br>GGCGGTGCCCCGCGGTGCGGGGGGCTGCGAGGGGAACA<br>AAGGCTGCGTGCGGGTGTGTGCGTGGGGGGTGAGCAG<br>GGGGTGTGGGCGCGGCGGTCGGGCTGTAACCCCCCCCTGC<br>ACCCCCCTCCCCGAGTTGCTGAGCACGGCCCGGCTTCGGG<br>TGCGGGGCTCCGTGCGGGGCGTGGCGCGGGGCTCGCCGTG<br>CCGGGCGGGGGTGGCGGCAGGTGGGGGTGCCGGGCGGG<br>GCGGGGCCGCCTCGGGCGGGGAGGGCTCGGGGGAGGGG<br>CGCGGCGGCCCCGGAGCGCCGGCGGCTGTCGAGGCGCGG<br>CGAGCCGCAGCCATTGCCTTTTATGGTAATCGTGCGAGAG<br>GGCGCAGGGACTTCCTTTGTCCCAAATCTGGCGGAGCCGA<br>AATCTGGGAGGCGCCGCCGCACCCCCTCTAGCGGGCGCGG<br>GCGAAGCGGTGCGGCGCCGGCAGGAAGGAAATGGGCGGG<br>GAGGGCCTTCGTGCGTCGCCGCGCCGCCGTCCCCTTCTCCA<br>TCTCCAGCCTCGGGGCTGCCGCAGGGGGACGGCTGCCTTC<br>GGGGGGACGGGGCAGGGCGGGGTTCGGCTTCTGGCGTG<br>TGACCGGCGGGAATTC |
| 36 | RSV promoter<br>and HIV Rev | CAATTGCGATGTACGGGCCAGATATACGCGTATCTGAGGG<br>GACTAGGGTGTGTTTAGGCGAAAAGCGGGGCTTCGGTTGT<br>ACGCGGTTAGGAGTCCCCTCAGGATATAGTAGTTTCGCTTT<br>TGCATAGGGAGGGGGAAATGTAGTCTTATGCAATACACTT<br>GTAGTCTTGCAACATGGTAACGATGAGTTAGCAACATGCC<br>TTACAAGGAGAGAAAAAGCACCGTGCATGCCGATTGGTG<br>GAAGTAAGGTGGTACGATCGTGCCTTATTAGGAAGGCAAC<br>AGACAGGTCTGACATGGATTGGACGAACCACTGAATTCCG<br>CATTGCAGAGATAATTGTATTTAAGTGCCTAGCTCGATAC<br>AATAAACGCCATTTGACCATTCACCACATTGGTGTGCACC<br>TCCAAGCTCGAGCTCGTTTAGTGAACCGTCAGATCGCCTG<br>GAGACGCCATCCACGCTGTTTTGACCTCCATAGAAGACAC<br>CGGGACCGATCCAGCCTCCCCTCGAAGCTAGCGATTAGGC<br>ATCTCCTATGGCAGGAAGAAGCGGAGACAGCGACGAAGA<br>ACTCCTCAAGGCAGTCAGACTCATCAAGTTTCTCTATCAA<br>AGCAACCCACCTCCCAATCCCGAGGGGACCCGACAGGCCC<br>GAAGGAATAGAAGAAGAAGGTGGAGAGAGAGACAGAGA<br>CAGATCCATTCGATTAGTGAACGGATCCTTAGCACTTATCT<br>GGGACGATCTGCGGAGCCTGTGCCTCTTCAGCTACCACCG<br>CTTGAGAGACTTACTCTTGATTGTAACGAGGATTGTGGAA<br>CTTCTGGGACGCAGGGGGTGGGAAGCCCTCAAATATTGGT<br>GGAATCTCCTACAATATTGGAGTCAGGAGCTAAAGAATAG<br>TCTAGA |
| 37 | Elongation<br>Factor-1 alpha<br>(EF 1-alpha)<br>promoter | CCGGTGCCTAGAGAAGGTGGCGCGGGGTAAACTGGGAAA<br>GTGATGTCGTGTACTGGCTCCGCCTTTTTCCCGAGGGTGGG<br>GGAGAACCGTATATAAGTGCAGTAGTCGCCGTGAACGTTC<br>TTTTTCGCAACGGGTTTGCCGCCAGAACACAGGTAAGTGC<br>CGTGTGTGGTTCCCGCGGGCCTGGCCTCTTTACGGGTTATG<br>GCCCTTGCGTGCCTTGAATTACTTCCACGCCCCTGGCTGCA<br>GTACGTGATTCTTGATCCCGAGCTTCGGGTTGGAAGTGGG<br>TGGGAGAGTTCGAGGCCTTGCGCTTAAGGAGCCCCCTTCGC<br>CTCGTGCTTGAGTTGAGGCCTGGCCTGGGCGCTGGGGCCG<br>CCGCGTGCGAATCTGGTGGCACCTTCGCGCCTGTCTCGCTG<br>CTTTCGATAAGTCTCTAGCCATTTAAAATTTTTGATGACCT<br>GCTGCGACGCTTTTTTTCTGGCAAGATAGTCTTGTAAATGC<br>GGGCCAAGATCTGCACACTGGTATTTCGGTTTTTGGGGCC<br>GCGGGCGGCGACGGGCCCGTGCGTCCCAGCGCACATGTT<br>CGGCGAGGCGGGGCCTGCGAGCGCGGCCACCGAGAATCG<br>GACGGGGGTAGTCTCAAGCTGGCCGGCCTGCTCTGGTGCC<br>TGGCCTCGCGCCGCCGTGTATCGCCCCGCCCTGGGCGGCA<br>AGGCTGGCCCGGTCGGCACCAGTTGCGTGAGCGGAAAGAT<br>GGCCGCTTCCCGGCCCTGCTGCAGGGAGCTCAAAATGGAG<br>GACGCGGCGCTCGGGAGAGCGGGCGGGTGAGTCACCCAC<br>ACAAAGGAAAAGGGCCTTTCCGTCCTCAGCCGTCGCTTCA<br>TGTGACTCCACGGAGTACCGGGCGCCGTCCAGGCACCTCG<br>ATTAGTTCTCGAGCTTTTGGAGTACGTCGTCTTTAGGTTGG<br>GGGGAGGGGTTTTATGCGATGGAGTTTCCCCACACTGAGT<br>GGGTGGAGACTGAAGTTAGGCCAGCTTGGCACTTGATGTA<br>ATTCTCCTTGGAATTTGCCCTTTTTGAGTTTGGATCTTGGTT<br>CATTCTCAAGCCTCAGACAGTGGTTCAAAGTTTTTTTCTTC<br>CATTTCAGGTGTCGTGA |
| 38 | Promoter;<br>PGK | GGGGTTGGGGTTGCGCCTTTTCCAAGGCAGCCCTGGGTTT<br>GCGCAGGGACGCGGCTGCTCTGGGCGTGGTTCCGGGAAAC |

| SEQ ID NO: | Description | Sequence |
|---|---|---|
| | | GCAGCGGCGCCGACCCTGGGTCTCGCACATTCTTCACGTC<br>CGTTCGCAGCGTCACCCGGATCTTCGCCGCTACCCTTGTGG<br>GCCCCCCGGCGACGCTTCCTGCTCCGCCCCTAAGTCGGGA<br>AGGTTCCTTGCGGTTCGCGGCGTGCCGGACGTGACAAACG<br>GAAGCCGCACGTCTCACTAGTACCCTCGCAGACGGACAGC<br>GCCAGGGAGCAATGGCAGCGCGCCGACCGCGATGGGCTG<br>TGGCCAATAGCGGCTGCTCAGCAGGGCGCGCCGAGAGCA<br>GCGGCCGGGAAGGGGCGGTGCGGGAGGCGGGGTGTGGGG<br>CGGTAGTGTGGGCCCTGTTCCTGCCCGCGCGGTGTTCCGC<br>ATTCTGCAAGCCTCCGGAGCGCACGTCGGCAGTCGGCTCC<br>CTCGTTGACCGAATCACCGACCTCTCTCCCCAG |
| 39 | Promoter; UbC | GCGCCGGGTTTTGGCGCCTCCCGCGGGCGCCCCCCTCCTC<br>ACGGCGAGCGCTGCCACGTCAGACGAAGGGCGCAGGAGC<br>GTTCCTGATCCTTCCGCCCGGACGCTCAGGACAGCGGCCC<br>GCTGCTCATAAGACTCGGCCTTAGAACCCCAGTATCAGCA<br>GAAGGACATTTTAGGACGGGACTTGGGTGACTCTAGGGCA<br>CTGGTTTTCTTTCCAGAGAGCGGAACAGGCGAGGAAAAGT<br>AGTCCCTTCTCGGCGATTCTGCGGAGGGATCTCCGTGGGG<br>CGGTGAACGCCGATGATTATATAAGGACGCGCCGGGTGTG<br>GCACAGCTAGTTCCGTCGCAGCCGGGATTTGGGTCGCGGT<br>TCTTGTTTGTGGATCGCTGTGATCGTCACTTGGTGAGTTGC<br>GGGCTGCTGGGCTGGCCGGGGCTTTCGTGGCCGCCGGGCC<br>GCTCGGTGGGACGGAAGCGTGTGGAGAGACCGCCAAGGG<br>CTGTAGTCTGGGTCCGCGAGCAAGGTTGCCCTGAACTGGG<br>GGTTGGGGGGAGCGCACAAAATGGCGGCTGTTCCCGAGTC<br>TTGAATGGAAGACGCTTGTAAGGCGGGCTGTGAGGTCGTT<br>GAAACAAGGTGGGGGGCATGGTGGGCGGCAAGAACCCAA<br>GGTCTTGAGGCCTTCGCTAATGCGGGAAAGCTCTTATTCG<br>GGTGAGATGGGCTGGGGCACCATCTGGGGACCCTGACGTG<br>AAGTTTGTCACTGACTGGAGAACTCGGGTTTGTCGTCTGGT<br>TGCGGGGGCGGCAGTTATGCGGTGCCGTTGGGCAGTGCAC<br>CCGTACCTTTGGGAGCGCGCGCCTCGTCGTGTCGTGACGT<br>CACCCGTTCTGTTGGCTTATAATGCAGGGTGGGGCCACCT<br>GCCGGTAGGTGTGCGGTAGGCTTTTCTCCGTCGCAGGACG<br>CAGGGTTCGGGCCTAGGGTAGGCTCTCCTGAATCGACAGG<br>CGCCGGACCTCTGGTGAGGGGAGGGATAAGTGAGGCGTC<br>AGTTTCTTTGGTCGGTTTTATGTACCTATCTTCTTAAGTAG<br>CTGAAGCTCCGGTTTTGAACTATGCGCTCGGGGTTGGCGA<br>GTGTGTTTTGTGAAGTTTTTTAGGCACCTTTTGAAATGTAA<br>TCATTTGGGTCAATATGTAATTTTCAGTGTTAGACTAGTAA<br>A |
| 40 | Poly A; SV40 | GTTTATTGCAGCTTATAATGGTTACAAATAAAGCAATAGC<br>ATCACAAATTTCACAAATAAAGCATTTTTTTCACTGCATTC<br>TAGTTGTGGTTTGTCCAAACTCATCAATGTATCTTATCA |
| 41 | Poly A; bGH | GACTGTGCCTTCTAGTTGCCAGCCATCTGTTGTTTGCCCCT<br>CCCCCGTGCCTTCCTTGACCCTGGAAGGTGCCACTCCCACT<br>GTCCTTTCCTAATAAAATGAGGAAATTGCATCGCATTGTCT<br>GAGTAGGTGTCATTCTATTCTGGGGGGTGGGGTGGGGCAG<br>GACAGCAAGGGGGAGGATTGGGAAGACAATAGCAGGCAT<br>GCTGGGGATGCGGTGGGCTCTATGG |
| 42 | Envelope;<br>RD 114 | ATGAAACTCCCAACAGGAATGGTCATTTTATGTAGCCTAA<br>TAATAGTTCGGGCAGGGTTTGACGACCCCCGCAAGGCTAT<br>CGCATTAGTACAAAAACAACATGGTAAACCATGCGAATGC<br>AGCGGAGGGCAGGTATCCGAGGCCCCACCGAACTCCATCC<br>AACAGGTAACTTGCCCAGGCAAGACGGCCTACTTAATGAC<br>CAACCAAAAATGGAAATGCAGAGTCACTCCAAAAAATCTC<br>ACCCCTAGCGGGGAGAACTCCAGAACTGCCCCTGTAACA<br>CTTTCCAGGACTCGATGCACAGTTCTTGTTATACTGAATAC<br>CGGCAATGCAGGGCGAATAATAAGACATACTACACGGCC<br>ACCTTGCTTAAAATACGGTCTGGGAGCCTCAACGAGGTAC<br>AGATATTACAAAACCCCAATCAGCTCCTACAGTCCCCTTG<br>TAGGGGCTCTATAAATCAGCCCGTTTGCTGGAGTGCCACA<br>GCCCCCATCCATATCTCCGATGGTGGAGGACCCCTCGATA<br>CTAAGAGAGTGTGGACAGTCCAAAAAAGGCTAGAACAAA<br>TTCATAAGGCTATGCATCCTGAACTTCAATACCACCCCTTA<br>GCCCTGCCCAAAGTCAGAGATGACCTTAGCCTTGATGCAC<br>GGACTTTTGATATCCTGAATACCACTTTTAGGTTACTCCAG<br>ATGTCCAATTTTAGCCTTGCCCAAGATTGTTGGCTCTGTTT<br>AAAACTAGGTACCCCTACCCCTCTTGCGATACCCACTCCCT<br>CTTTAACCTACTCCCTAGCAGACTCCCTAGCGAATGCCTCC<br>TGTCAGATTATACCTCCCCTCTTGGTTCAACCGATGCAGTT<br>CTCCAACTCGTCCTGTTTATCTTCCCCTTTCATTAACGATA<br>CGGAACAAATAGACTTAGGTGCAGTCACCTTTACTAACTG |

| SEQ ID NO: | Description | Sequence |
|---|---|---|
|  |  | CACCTCTGTAGCCAATGTCAGTAGTCCTTTATGTGCCCTAA ACGGGTCAGTCTTCCTCTGTGGAAATAACATGGCATACAC CTATTTACCCCAAAACTGGACAGGACTTTGCGTCCAAGCC TCCCTCCTCCCCGACATTGACATCATCCCGGGGGATGAGC CAGTCCCCATTCCTGCCATTGATCATTATATACATAGACCT AAACGAGCTGTACAGTTCATCCCTTTACTAGCTGGACTGG GAATCACCGCAGCATTCACCACCGGAGCTACAGGCCTAGG TGTCTCCGTCACCCAGTATACAAAATTATCCCATCAGTTAA TATCTGATGTCCAAGTCTTATCCGGTACCATACAAGATTTA CAAGACCAGGTAGACTCGTTAGCTGAAGTAGTTCTCCAAA ATAGGAGGGGACTGGACCTACTAACGGCAGAACAAGGAG GAATTTGTTTAGCCTTACAAGAAAATGCTGTTTTTATGCT AACAAGTCAGGAATTGTGAGAAACAAAATAAGAACCCTA CAAGAAGAATTACAAAAACGCAGGGAAAGCCTGGCATCC AACCCTCTCTGGACCGGGCTGCAGGGCTTTCTTCCGTACCT CCTACCTCTCCTGGGACCCCTACTCACCCTCCTACTCATAC TAACCATTGGGCCATGCGTTTTCAATCGATTGGTCCAATTT GTTAAAGACAGGATCTCAGTGGTCCAGGCTCTGGTTTTGA CTCAGCAATATCACCAGCTAAAACCCATAGAGTACGAGCC ATGA |
| 43 | Envelope; GALV | ATGCTTCTCACCTCAAGCCCGCACCACCTTCGGCACCAGA TGAGTCCTGGGAGCTGGAAAAGACTGATCATCCTCTTAAG CTGCGTATTCGGAGACGGCAAAACGAGTCTGCAGAATAAG AACCCCCACCAGCCTGTGACCCTCACCTGGCAGGTACTGT CCCAAACTGGGGACGTTGTCTGGGACAAAAAGGCAGTCCA GCCCCTTTGGACTTGGTGGCCCTCTCTTACACCTGATGTAT GTGCCCTGGCGGCCGGTCTTGAGTCCTGGGATATCCCGGG ATCCGATGTATCGTCCTCTAAAAGAGTTAGACCTCCTGATT CAGACTATACTGCCGCTTATAAGCAAATCACCTGGGGAGC CATAGGGTGCAGCTACCCTCGGGCTAGGACCAGGATGGCA AATTCCCCCTTCTACGTGTGTCCCCGAGCTGGCCGAACCCA TTCAGAAGCTAGGAGGTGTGGGGGGCTAGAATCCCTATAC TGTAAAGAATGGAGTTGTGAGACCACGGGTACCGTTTATT GGCAACCCAAGTCCTCATGGGACCTCATAACTGTAAAATG GGACCAAAATGTGAAATGGGAGCAAAAATTTCAAAAGTG TGAACAAACCGGCTGGTGTAACCCCCTCAAGATAGACTTC ACAGAAAAAGGAAAACTCTCCAGAGATTGGATAACGGAA AAAACCTGGGAATTAAGGTTCTATGTATATGGACACCCAG GCATACAGTTGACTATCCGCTTAGAGGTCACTAACATGCC GGTTGTGGCAGTGGGCCCAGACCCTGTCCTTGCGGAACAG GGACCTCCTAGCAAGCCCCTCACTCTCCCTCTCTCCCCACG GAAAGCGCCGCCCACCCCTCTACCCCCGGCGGCTAGTGAG CAAACCCCTGCGGTGCATGGAGAAACTGTTACCCTAAACT CTCCGCCTCCCACCAGTGGCGACCGACTCTTTGGCCTTGTG CAGGGGGCCTTCCTAACCTTGAATGCTACCAACCCAGGG CCACTAAGTCTTGCTGGCTCTGTTTGGGCATGAGCCCCCCT TATTATGAAGGGATAGCCTCTTCAGGAGAGGTCGCTTATA CCTCCAACCATACCCGATGCCACTGGGGGGCCCAAGGAAA GCTTACCCTCACTGAGGTCTCCGGACTCGGGTCATGCATA GGGAAGGTGCCTCTTACCCATCAACATCTTTGCAACCAGA CCTTACCCATCAATTCCTCTAAAAACCATCAGTATCTGCTC CCCTCAAACCATAGCTGGTGGGCCTGCAGCACTGGCCTCA CCCCCTGCCTCTCCACCTCAGTTTTTAATCAGTCTAAAGAC TTCTGTGTCCAGGTCCAGCTGATCCCCCGCATCTATTACCA TTCTGAAGAAACCTTGTTACAAGCCTATGACAAATCACCC CCCAGGTTTAAAAGAGAGCCTGCCTCACTTACCCTAGCTG TCTTCCTGGGGTTAGGGATTGCGGCAGGTATAGGTACTGG CTCAACCGCCCTAATTAAAGGGCCCATAGACCTCCAGCAA GGCCTAACCAGCCTCCAAATCGCCATTGACGCTGACCTCC GGGCCCTTCAGGACTCAATCAGCAAGCTAGAGGACTCACT GACTTCCCTATCTGAGGTAGTACTCCAAAATAGGAGAGGC CTTGACTTACTATTCCTTAAAGAAGGAGGCCTCTGCGCGG CCCTAAAAGAAGAGTGCTGTTTTTATGTAGACCACTCAGG TGCAGTACGAGACTCCATGAAAAAACTTAAAGAAAGACT AGATAAAAGACAGTTAGAGCGCCAGAAAAACCAAACTG GTATGAAGGGTGGTTCAATAACTCCCCTTGGTTTACTACCC TACTATCAACCATCGCTGGGCCCCTATTGCTCCTCCTTTTG TTACTCACTCTTGGGCCCTGCATCATCAATAAATTAATCCA ATTCATCAATGATAGGATAAGTGCAGTCAAAATTTTAGTC CTTAGACAGAAATATCAGACCCTAGATAACGAGGAAAAC CTTTAA |
| 44 | Envelope; FUG | ATGGTTCCGCAGGTTCTTTTGTTTGTACTCCTTCTGGGTTTT TCGTTGTGTTTCGGGAAGTTCCCCATTTACACGATACCAGA CGAACTTGGTCCCTGGAGCCCTATTGACATACACCATCTC AGCTGTCCAAATAACCTGGTTGTGGAGGATGAAGGATGTA |

| SEQ ID NO: | Description | Sequence |
|---|---|---|
| | | CCAACCTGTCCGAGTTCTCCTACATGGAACTCAAAGTGGG
ATACATCTCAGCCATCAAAGTGAACGGGTTCACTTGCACA
GGTGTTGTGACAGAGGCAGAGACCTACACCAACTTTGTTG
GTTATGTCACAACCACATTCAAGAGAAAGCATTTCCGCCC
CACCCCAGACGCATGTAGAGCCGCGTATAACTGGAAGATG
GCCGGTGACCCCAGATATGAAGAGTCCCTACACAATCCAT
ACCCCGACTACCACTGGCTTCGAACTGTAAGAACCACCAA
AGAGTCCCTCATTATCATATCCCCAAGTGTGACAGATTTG
GACCCATATGACAAATCCCTTCACTCAAGGGTCTTCCCTG
GCGGAAAGTGCTCAGGAATAACGGTGTCCTCTACCTACTG
CTCAACTAACCATGATTACACCATTTGGATGCCCGAGAAT
CCGAGACCAAGGACACCTTGTGACATTTTTACCAATAGCA
GAGGGAAGAGAGCATCCAACGGGAACAAGACTTGCGGCT
TTGTGGATGAAAGAGGCCTGTATAAGTCTCTAAAAGGAGC
ATGCAGGCTCAAGTTATGTGGAGTTCTTGGACTTAGACTT
ATGGATGGAACATGGGTCGCGATGCAAACATCAGATGAG
ACCAAATGGTGCCCTCCAGATCAGTTGGTGAATTTGCACG
ACTTTCGCTCAGACGAGATCGAGCATCTCGTTGTGGAGGA
GTTAGTTAAGAAAAGAGAGGAATGTCTGGATGCATTAGAG
TCCATCATGACCACCAAGTCAGTAAGTTTCAGACGTCTCA
GTCACCTGAGAAAACTTGTCCCAGGGTTTGGAAAAGCATA
TACCATATTCAACAAAACCTTGATGGAGGCTGATGCTCAC
TACAAGTCAGTCCGGACCTGGAATGAGATCATCCCCTCAA
AAGGGTGTTTGAAAGTTGGAGGAAGGTGCCATCCTCATGT
GAACGGGTGTTTTTCAATGGTATAATATTAGGGCCTGAC
GACCATGTCCTAATCCCAGAGATGCAATCATCCCTCCTCC
AGCAACATATGGAGTTGTTGGAATCTTCAGTTATCCCCCTG
ATGCACCCCCTGGCAGACCCTTCTACAGTTTTCAAAGAAG
GTGATGAGGCTGAGGATTTTGTTGAAGTTCACCTCCCCGA
TGTGTACAAACAGATCTCAGGGGTTGACCTGGGTCTCCCG
AACTGGGGAAAGTATGTATTGATGACTGCAGGGGCCATGA
TTGGCCTGGTGTTGATATTTTCCCTAATGACATGGTGCAGA
GTTGGTATCCATCTTTGCATTAAATTAAAGCACACCAAGA
AAAGACAGATTTATACAGACATAGAGATGAACCGACTTGG
AAAGTAA |
| 45 | Envelope;
LCMV | ATGGGTCAGATTGTGACAATGTTTGAGGCTCTGCCTCACA
TCATCGATGAGGTGATCAACATTGTCATTATTGTGCTTATC
GTGATCACGGGTATCAAGGCTGTCTACAATTTTGCCACCT
GTGGGATATTCGCATTGATCAGTTTCCTACTTCTGGCTGGC
AGGTCCTGTGGCATGTACGGTCTTAAGGGACCCGACATTT
ACAAAGGAGTTTACCAATTTAAGTCAGTGGAGTTTGATAT
GTCACATCTGAACCTGACCATGCCCAACGCATGTTCAGCC
AACAACTCCCACCATTACATCAGTATGGGGACTTCTGGAC
TAGAATTGACCTTCACCAATGATTCCATCATCAGTCACAA
CTTTTGCAATCTGACCTCTGCCTTCAACAAAAAGACCTTTG
ACCACACACTCATGAGTATAGTTTCGAGCCTACACCTCAG
TATCAGAGGGAACTCCAACTATAAGGCAGTATCCTGCGAC
TTCAACAATGGCATAACCATCCAATACAACTTGACATTCT
CAGATCGACAAAGTGCTCAGAGCCAGTGTAGAACCTTCAG
AGGTAGAGTCCTAGATATGTTTAGAACTGCCTTCGGGGGG
AAATACATGAGGAGTGGCTGGGGCTGGACAGGCTCAGAT
GGCAAGACCACCTGGTGTAGCCAGACGAGTTACCAATACC
TGATTATACAAAATAGAACCTGGGAAAACCACTGCACATA
TGCAGGTCCTTTTGGGATGTCCAGGATTCTCCTTTCCCAAG
AGAAGACTAAGTTCTTCACTAGGAGACTAGCGGGCACATT
CACCTGGACTTTGTCAGACTCTTCAGGGGTGGAGAATCCA
GGTGGTTATTGCCTGACCAAATGGATGATTCTTGCTGCAG
AGCTTAAGTGTTTCGGGAACACAGCAGTTGCGAAATGCAA
TGTAAATCATGATGCCGAATTCTGTGACATGCTGCGACTA
ATTGACTACAACAAGGCTGCTTTGAGTAAGTTCAAAGAGG
ACGTAGAATCTGCCTTGCACTTATTCAAAACAACAGTGAA
TTCTTTGATTTCAGATCAACTACTGATGAGGAACCACTTGA
GAGATCTGATGGGGGTGCCATATTGCAATTACTCAAAGTT
TTGGTACCTAGAACATGCAAAGACCGGCGAAACTAGTGTC
CCCAAGTGCTGGCTTGTCACCAATGGTTCTTACTTAAATGA
GACCCACTTCAGTGATCAAATCGAACAGGAAGCCGATAAC
ATGATTACAGAGATGTTGAGGAAGGATTACATAAAGAGG
CAGGGGGAGTACCCCCCTAGCATTGATGGACCTTCTGATGT
TTTCCACATCTGCATATCTAGTCAGCATCTTCCTGCACCTT
GTCAAAATACCAACACACAGGCACATAAAAGGTGGCTCAT
GTCCAAAGCCACACCGATTAACCAACAAAGGAATTTGTAG
TTGTGGTGCATTTAAGGTGCCTGGTGTAAAAACCGTCTGG
AAAAGACGCTGA |
| 46 | Envelope;
FPV | ATGAACACTCAAATCCTGGTTTTCGCCCTTGTGGCAGTCAT
CCCCACAAATGCAGACAAAATTTGTCTTGGACATCATGCT |

| SEQ ID NO: | Description | Sequence |
|---|---|---|
| | | GTATCAAATGGCACCAAAGTAAACACACTCACTGAGAGA<br>GGAGTAGAAGTTGTCAATGCAACGGAAACAGTGGAGCGG<br>ACAAACATCCCCAAAATTTGCTCAAAAGGGAAAAGAACC<br>ACTGATCTTGGCCAATGCGGACTGTTAGGGACCATTACCG<br>GACCACCTCAATGCGACCAATTTCTAGAATTTTCAGCTGAT<br>CTAATAATCGAGAGACGAGAAGGAAATGATGTTTGTTACC<br>CGGGGAAGTTTGTTAATGAAGAGGCATTGCGACAAATCCT<br>CAGAGGATCAGGTGGGATTGACAAAGAAACAATGGGATT<br>CACATATAGTGGAATAAGGACCAACGGAACAACTAGTGC<br>ATGTAGAAGATCAGGGTCTTCATTCTATGCAGAAATGGAG<br>TGGCTCCTGTCAAATACAGAGACAATGCTGCTTTCCCACAA<br>TGACAAAATCATACAAAAACACAAGGAGAGAATCAGCTC<br>TGATAGTCTGGGGAATCCACCATTCAGGATCAACCACCGA<br>ACAGACCAAACTATATGGGAGTGGAAATAAACTGATAAC<br>AGTCGGGAGTTCCAAATATCATCAATCTTTTGTGCCGAGTC<br>CAGGAACACGACCGCAGATAAATGGCCAGTCCGGACGGA<br>TTGATTTTCATTGGTTGATCTTGGATCCCAATGATACAGTT<br>ACTTTTAGTTTCAATGGGGCTTTCATAGCTCCAAATCGTGC<br>CAGCTTCTTGAGGGGAAAGTCCATGGGGATCCAGAGCGAT<br>GTGCAGGTTGATGCCAATTGCGAAGGGGAATGCTACCACA<br>GTGGAGGGACTATAACAAGCAGATTGCCTTTTCAAAACAT<br>CAATAGCAGAGCAGTTGGCAAATGCCCAAGATATGTAAA<br>ACAGGAAAGTTTATTATTGGCAACTGGGATGAAGAACGTT<br>CCCGAACCTTCCAAAAAAAGGAAAAAAAGAGGCCTGTTT<br>GGCGCTATAGCAGGGTTTATTGAAAATGGTTGGGAAGGTC<br>TGGTCGACGGGTGGTACGGTTTCAGGCATCAGAATGCACA<br>AGGAGAAGGAACTGCAGCAGACTACAAAAGCACCCAATC<br>GGCAATTGATCAGATAACCGGAAAGTTAAATAGACTCATT<br>GAGAAAACCAACCAGCAATTTGAGCTAATAGATAATGAAT<br>TCACTGAGGTGGAAAAGCAGATTGGCAATTTAATTAACTG<br>GACCAAAGACTCCATCACAGAAGTATGGTCTTACAATGCT<br>GAACTTCTTGTGGCAATGGAAAACCAGCACACTATTGATT<br>TGGCTGATTCAGAGATGAACAAGCTGTATGAGCGAGTGAG<br>GAAACAATTAAGGGAAAATGCTGAAGAGGATGGCACTGG<br>TTGCTTTGAAATTTTTCATAAATGTGACGATGATTGTATGG<br>CTAGTATAAGGAACAATACTTATGATCACAGCAAATACAG<br>AGAAGAAGCGATGCAAAATAGAATACAAATTGACCCAGT<br>CAAATTGAGTAGTGGCTACAAAGATGTGATACTTTGGTTT<br>AGCTTCGGGGCATCATGCTTTTTGCTTCTTGCCATTGCAAT<br>GGGCCTTGTTTTCATATGTGTGAAGAACGGAAACATGCGG<br>TGCACTATTTGTATATAA |
| 47 | Envelope;<br>RRV | AGTGTAACAGAGCACTTTAATGTGTATAAGGCTACTAGAC<br>CATACCTAGCACATTGCGCCGATTGCGGGGACGGGTACTT<br>CTGCTATAGCCCAGTTGCTATCGAGGAGATCCGAGATGAG<br>GCGTCTGATGGCATGCTTAAGATCCAAGTCTCCGCCCAAA<br>TAGGTCTGGACAAGGCAGGCACCCACGCCCACACGAAGCT<br>CCGATATATGGCTGGTCATGATGTTCAGGAATCTAAGAGA<br>GATTCCTTGAGGGTGTACACGTCCGCAGCGTGCTCCATAC<br>ATGGGACGATGGGACACTTCATCGTCGCACACTGTCCACC<br>AGGCGACTACCTCAAGGTTTCGTTCGAGGACGCAGATTCG<br>CACGTGAAGGCATGTAAGGTCCAATACAAGCACAATCCAT<br>TGCCGGTGGGTAGAGAGAAGTTCGTGGTTAGACCACACTT<br>TGGCGTAGAGCTGCCATGCACCTCATACCAGCTGACAACG<br>GCTCCCACCGACGAGGAGATTGACATGCATACACCGCCAG<br>ATATACCGGATCGCACCCTGCTATCACAGACGGCGGGCAA<br>CGTCAAAATAACAGCAGGCGGCAGGACTATCAGGTACAA<br>CTGTACCTGCGGCCGTGACAACGTAGGCACTACCAGTACT<br>GACAAGACCATCAACACATGCAAGATTGACCAATGCCATG<br>CTGCCGTCACCAGCCATGACAAATGGCAATTTACCTCTCC<br>ATTTGTTCCCAGGGCTGATCAGACAGCTAGGAAAGGCAAG<br>GTACACGTTCCGTTCCCTCTGACTAACGTCACCTGCCGAGT<br>GCCGTTGGCTCGAGCGCCGGATGCCACCTATGGTAAGAAG<br>GAGGTGACCCTGAGATTACACCCAGATCATCCGACGCTCT<br>TCTCCTATAGGAGTTTAGGAGCCGAACCGCACCCGTACGA<br>GGAATGGGTTGACAAGTTCTCTGAGCGCATCATCCCAGTG<br>ACGGAAGAAGGGATTGAGTACCAGTGGGGCAACAACCCG<br>CCGGTCTGCCTGTGGGCGCAACTGACGACCGAGGGCAAAC<br>CCCATGGCTGGCCACATGAAATCATTCAGTACTATTATGG<br>ACTATACCCCGCCGCCACTATTGCCGCAGTATCCGGGGCG<br>AGTCTGATGGCCCTCCTAACTCTGGCGGCCACATGCTGCA<br>TGCTGGCCACCGCGAGGAGAAAGTGCCTAACACCGTACGC<br>CCTGACGCCAGGAGCGGTGGTACCGTTGACACTGGGGCTG<br>CTTTGCTGCGCACCGAGGGCGAATGCA |
| 48 | Envelope;<br>Ebola | ATGGGTGTTACAGGAATATTGCAGTTACCTCGTGATCGAT<br>TCAAGAGGACATCATTCTTTCTTTGGGTAATTATCCTTTTC |

| SEQ ID NO: | Description | Sequence |
|---|---|---|
| | | CAAAGAACATTTTCCATCCCACTTGGAGTCATCCACAATA<br>GCACATTACAGGTTAGTGATGTCGACAAACTGGTTTGCCG<br>TGACAAACTGTCATCCACAAATCAATTGAGATCAGTTGGA<br>CTGAATCTCGAAGGGAATGGAGTGGCAACTGACGTGCCAT<br>CTGCAACTAAAAGATGGGGCTTCAGGTCCGGTGTCCCACC<br>AAAGGTGGTCAATTATGAAGCTGGTAATGGGCTGAAAAC<br>TGCTACAATCTTGAAATCAAAAAACCTGACGGGAGTGAGT<br>GTCTACCAGCAGCGCCAGACGGGATTCGGGGCTTCCCCCG<br>GTGCCGGTATGTGCACAAAGTATCAGGAACGGGACCGTGT<br>GCCGGAGACTTTGCCTTCCACAAAGAGGGTGCTTTCTTCCT<br>GTATGACCGACTTGCTTCCACAGTTATCTACCGAGGAACG<br>ACTTTCGCTGAAGGTGTCGTTGCATTTCTGATACTGCCCCA<br>AGCTAAGAAGGACTTCTTCAGCTCACACCCCTTGAGAGAG<br>CCGGTCAATGCAACGGAGGACCCGTCTAGTGGCTACTATT<br>CTACCACAATTAGATATCAAGCTACCGGTTTTGGAACCAA<br>TGAGACAGAGTATTTGTTCGAGGTTGACAATTTGACCTAC<br>GTCCAACTTGAATCAAGATTCACACCACAGTTTCTGCTCCA<br>GCTGAATGAGACAATATATACAAGTGGGAAAAGGAGCAA<br>TACCACGGGAAAACTAATTTGGAAGGTCAACCCCGAAATT<br>GATACAACAATCGGGGAGTGGGCCTTCTGGGAAACTAAA<br>AAAACCTCACTAGAAAAATTCGCAGTGAAGAGTTGTCTTT<br>CACAGCTGTATCAAACAGAGCCAAAAACATCAGTGGTCAG<br>AGTCCGGCGCGAACTTCTTCCGACCCAGGGACCAACACAA<br>CAACTGAAGACCACAAAATCATGGCTTCAGAAAATTCCTC<br>TGCAATGGTTCAAGTGCACAGTCAAGGAAGGGAAGCTGC<br>AGTGTCGCATCTGACAACCCTTGCCACAATCTCCACGAGT<br>CCTCAACCCCCCACAACCAAACCAGGTCCGGACAACAGCA<br>CCCACAATACACCCGTGTATAAACTTGACATCTCTGAGGC<br>AACTCAAGTTGAACAACATCACCGCAGAACAGACAACGA<br>CAGCACAGCCTCCGACACTCCCCCCGCCACGACCGCAGCC<br>GGACCCCTAAAAGCAGAGAACACCAACACGAGCAAGGGT<br>ACCGACCTCCTGGACCCCGCCACCACAACAAGTCCCCAAA<br>ACCACAGCGAGACCGCTGGCAACAACAACACTCATCACCA<br>AGATACCGGAGAAGAGAGTGCCAGCAGCGGGAAGCTAGG<br>CTTAATTACCAATACTATTGCTGGAGTCGCAGGACTGATC<br>ACAGGCGGGAGGAGAGCTCGAAGAGAAGCAATTGTCAAT<br>GCTCAACCCAAATGCAACCCTAATTTACATTACTGGACTA<br>CTCAGGATGAAGGTGCTGCAATCGGACTGGCCTGGATACC<br>ATATTTCGGGCCAGCAGCCGAGGGAATTTACATAGAGGGG<br>CTGATGCACAATCAAGATGGTTTAATCTGTGGGTTGAGAC<br>AGCTGGCCAACGAGACGACTCAAGCTCTTCAACTGTTCCT<br>GAGAGCCACAACCGAGCTACGCACCTTTTCAATCCTCAAC<br>CGTAAGGCAATTGATTTCTTGCTGCAGCGATGGGGCGGCA<br>CATGCCACATTTTGGGACCGGACTGCTGTATCGAACCACA<br>TGATTGGACCAAGAACATAACAGACAAAATTGATCAGATT<br>ATTCATGATTTTGTTGATAAAACCCTTCCGGACCAGGGGG<br>ACAATGACAATTGGTGGACAGGATGGAGACAATGGATAC<br>CGGCAGGTATTGGAGTTACAGGCGTTATAATTGCAGTTAT<br>CGCTTTATTCTGTATATGCAAATTTGTCTTTTAG |
| 49 | FDPS target sequence #1 | GTCCTGGAGTACAATGCCATT |
| 50 | FDPS target sequence #2 | GCAGGATTTCGTTCAGCACTT |
| 51 | FDPS target sequence #3 | GCCATGTACATGGCAGGAATT |
| 52 | FDPS target sequence #4 | GCAGAAGGAGGCTGAGAAAGT |
| 53 | miR30 FDPS sequence #1 | AAGGTATATTGCTGTTGACAGTGAGCGACACTTTCTCAGC<br>CTCCTTCTGCGTGAAGCCACAGATGGCAGAAGGAGGCTGA<br>GAAAGTGCTGCCTACTGCCTCGGACTTCAAGGGGCT |
| 54 | miR30 FDPS sequence #2 | AAGGTATATTGCTGTTGACAGTGAGCGACACTTTCTCAGC<br>CTCCTTCTGCGTGAAGCCACAGATGGCAGAAGGGCTGAGA<br>AAGTGCTGCCTACTGCCTCGGACTTCAAGGGGCT |
| 55 | miR30 FDPS sequence #3 | TGCTGTTGACAGTGAGCGACTTTCTCAGCCTCCTTCTGCGT<br>GAAGCCACAGATGGCAGAAGGAGGCTGAGAAAGTTGCCT<br>ACTGCCTCGGA |
| 56 | miR155 FDPS sequence #1 | CCTGGAGGCTTGCTGAAGGCTGTATGCTGACTTTCTCAGCC<br>TCCTTCTGCTTTTGGCCACTGACTGAGCAGAAGGGCTGAG<br>AAAGTCAGGACACAAGGCCTGTTACTAGCACTCA |

-continued

| SEQ ID NO: | Description | Sequence |
|---|---|---|
| 57 | miR21 FDPS sequence #1 | CATCTCCATGGCTGTACCACCTTGTCGGGACTTTCTCAGCC TCCTTCTGCCTGTTGAATCTCATGGCAGAAGGAGGCGAGA AAGTCTGACATTTTGGTATCTTTCATCTGACCA |
| 58 | miR185 FDPS sequence #1 | GGGCCTGGCTCGAGCAGGGGCGAGGGATACTTTCTCAGC CTCCTTCTGCTGGTCCCCTCCCCGCAGAAGGAGGCTGAGA AAGTCCTTCCCTCCCAATGACCGCGTCTTCGTCG |
| 59 | Forward primer | AGGAATTGATGGCGAGAAGG |
| 60 | Reverse primer | CCCAAAGAGGTCAAGGTAATCA |
| 61 | Forward primer | AGCGCGGCTACAGCTTCA |
| 62 | Reverse primer | GGCGACGTAGCACAGCTTCT |
| 63 | Forward primer | CACTGTCGTCATTCCATGCT |
| 64 | Reverse primer | GCCTCTTGACATTCTCCTC |
| 65 | Reverse primer | AAAGTCAGTGGGACAGTGG |
| 66 | miR155 CD47 target sequence #2 | CCTGGAGGCTTGCTGAAGGCTGTATGCTGTTAGCTCGATG ATCGTTTCACGTTTTGGCCACTGACTGACGTGAAACGCATC GAGCTAACAGGACACAAGGCCTGTTACTAGCACTCA |
| 67 | miR155 CD47 target sequence #3 | CCTGGAGGCTTGCTGAAGGCTGTATGCTGAAGAATGGCTC CAACAATGACGTTTTGGCCACTGACTGACGTCATTGTGAG CCATTCTTCAGGACACAAGGCCTGTTACTAGCACTCA |
| 68 | miR155 CD47 target sequence #4 | CCTGGAGGCTTGCTGAAGGCTGTATGCTGTATACACGCCG CAATACAGAGGTTTTGGCCACTGACTGACCTCTGTATCGG CGTGTATACAGGACACAAGGCCTGTTACTAGCACTCA |
| 69 | Forward primer | GGACTATCCTGCTGCCAA |
| 70 | miR155 cMyc sequence | CCTGGAGGCTTGCTGAAGGCTGTATGCTGTGTTCGCCTCTT GACATTCTCTTTTGGCCACTGACTGAGAGAATGTAGAGGC GAACACAGGACACAAGGCCTGTTACTAGCACTCA |
| 71 | cMyc target sequence | GAGAATGTCAAGAGGCGAACA |
| 72 | CMV promoter sequence | ATTATGCCCAGTACATGACCTTATGGGACTTTCCTACTTGG CAGTACATCTACGTATTAGTCATCGCTATTACCATGGTGAT GCGGTTTTGGCAGTACATCAATGGGCGTGGATAGCGGTTT GACTCACGGGGATTTCCAAGTCTCCACCCCATTGACGTCA ATGGGAGTTTGTTTTGGCACCAAAATCAACGGGACTTTCC AAAATGTCGTAACAACTCCGCCCCATTGACGCAAATGGGC GGTAGGCGTGTACGGTGGGAGGTTTATATAAGCAGAGCTC GTTTAGTGAACCGTCAGATCGCCTGGAGACGCCATCCACG CTGTTTT |
| 73 | GFP T2A Luciferase sequence | ATGCCCGCCATGAAGATCGAGTGCCGCATCACCGGCACCC TGAACGGCGTGGAGTTCGAGCTGGTGGGCGGCGGAGAGG GCACCCCCGAGCAGGGCCGCATGACCAACAAGATGAAGA GCACCAAAGGCGCCCTGACCTTCAGCCCCTACCTGCTGAG CCACGTGATGGGCTACGGCTTCTACCACTTCGGCACCTAC CCCAGCGGCTACGAGAACCCCTTCCTGCACGCCATCAACA ACGGCGGCTACACCAACACCCGCATCGAGAAGTACGAGG ACGGCGGCGTGCTGCACGTGAGCTTCAGCTACCGCTACGA GGCCGGCCGCGTGATCGGCGACTTCAAGGTGGTGGGCACC GGCTTCCCCGAGGACAGCGTGATCTTCACCGACAAGATCA TCCGCAGCAACGCCACCGTGGAGCACCTGCACCCCATGGG CGATAACGTGCTGGTGGGCAGCTTCGCCCGCACCTTCAGC CTGCGCGACGGCGGCTACTACAGCTTCGTGGTGGACAGCC ACATGCACTTCAAGAGCGCCATCCACCCCAGCATCCTGCA GAACGGGGCCCCCATGTTCGCCTTCCGCCGCGTGGAGGAG CTGCACAGCAACACCGAGCTGGGCATCGTGGAGTACCAGC ACGCCTTCAAGACCCCCATCGCCTTCGCCAGATCTCGAGA TATCAGCCATGGCTTCCCGCCGGCGGTGGCGGCGCAGGAT GATGGCACGCTGCCCATGTCTTGTGCCCAGGAGAGCGGGA |

-continued

| SEQ ID NO: | Description | Sequence |
|---|---|---|
| | | TGGACCGTCACCCTGCAGCCTGTGCTTCTGCTAGGATCAAT<br>GTGACCGGTGAGGGCAGAGGAAGTCTTCTAACATGCGGTG<br>ACGTGGAGGAGAATCCCGGCCCTTCCGGTATGGAAGACGC<br>CAAAAACATAAAGAAAGGCCCGGCGCCATTCTATCCGCTA<br>GAGGATGGAACCGCTGGAGAGCAACTGCATAAGGCTATG<br>AAGAGATACGCCCTGGTTCCTGGAACAATTGCTTTTACAG<br>ATGCACATATCGAGGTGAACATCACGTACGCGGAATACTT<br>CGAAATGTCCGTTCGGTTGGCAGAAGCTATGAAACGATAT<br>GGGCTGAATACAAATCACAGAATCGTCGTATGCAGTGAAA<br>ACTCTCTTCAATTCTTTATGCCGGTGTTGGGCGCGTTATTT<br>ATCGGAGTTGCAGTTGCGCCCGCGAACGACATTTATAATG<br>AACGTGAATTGCTCAACAGTATGAACATTTCGCAGCCTAC<br>CGTAGTGTTTGTTTCCAAAAAGGGGTTGCAAAAAATTTTG<br>AACGTGCAAAAAAAATTACCAATAATCCAGAAAATTATTA<br>TCATGGATTCTAAAACGGATTACCAGGGATTTCAGTCGAT<br>GTACACGTTCGTCACATCTCATCTACCTCCCGGTTTTAATG<br>AATACGATTTTGTACCAGAGTCCTTTGATCGTGACAAAAC<br>AATTGCACTGATAATGAACTCCTCTGGATCTACTGGGTTAC<br>CTAAGGGTGTGGCCCTTCCGCATAGAACTGCCTGCGTCAG<br>ATTCTCGCATGCCAGAGATCCTATTTTTGGCAATCAAATCA<br>TTCCGGATACTGCGATTTTAAGTGTTGTTCCATTCCATCAC<br>GGTTTTGGAATGTTTACTACACTCGGATATTTGATATGTGG<br>ATTTCGAGTCGTCTTAATGTATAGATTTGAAGAAGAGCTG<br>TTTTTACGATCCCTTCAGGATTACAAAATTCAAAGTGCGTT<br>GCTAGTACCAACCCTATTTTCATTCTTCGCCAAAAGCACTC<br>TGATTGACAAATACGATTTATCTAATTTACACGAAATTGCT<br>TCTGGGGGCGCACCTCTTTCGAAAGAAGTCGGGGAAGCGG<br>TTGCAAAACGCTTCCATCTTCCAGGGATACGACAAGGATA<br>TGGGCTCACTGAGACTACATCAGCTATTCTGATTACACCC<br>GAGGGGGATGATAAACCGGGCGCGGTCGGTAAAGTTGTTC<br>CATTTTTTGAAGCGAAGGTTGTGGATCTGGATACCGGGAA<br>AACGCTGGGCGTTAATCAGAGAGGCGAATTATGTGTCAGA<br>GGACCTATGATTATGTCCGGTTATGTAAACAATCCGGAAG<br>CGACCAACGCCTTGATTGACAAGGATGGATGGCTACATTC<br>TGGAGACATAGCTTACTGGGACGAAGACGAACACTTCTTC<br>ATAGTTGACCGCTTGAAGTCTTTAATTAAATACAAAGGAT<br>ACCAGGTGGCCCCCGCTGAATTGGAGTCGATATTGTTACA<br>ACACCCCAACATCTTCGACGCGGGCGTGGCAGGTCTTCCC<br>GACGATGACGCCGGTGAACTTCCCGCCGCCGTTGTTGTTTT<br>GGAGCACGGAAAGACGATGACGGAAAAAGAGATCGTGGA<br>TTACGTCGCCAGTCAAGTAACAACCGCGAAAAAGTTGCGC<br>GGAGGAGTTGTGTTTGTGGACGAAGTACCGAAAGGTCTTA<br>CCGGAAAACTCGACGCAAGAAAAATCAGAGAGATCCTCA<br>TAAAGGCCAAGAAGGGCGGAAAGTCCAAATTGTAA |
| 74 | Rous Sarcoma virus (RSV) promoter | GTAGTCTTATGCAATACTCTTGTAGTCTTGCAACATGGTAA<br>CGATGAGTTAGCAACATGCCTTACAAGGAGAGAAAAAGC<br>ACCGTGCATGCCGATTGGTGGAAGTAAGGTGGTACGATCG<br>TGCCTTATTAGGAAGGCAACAGACGGGTCTGACATGGATT<br>GGACGAACCACTGAATTGCCGCATTGCAGAGATATTGTAT<br>TTAAGTGCCTAGCTCGATACAATAAACG |
| 75 | 5' Long terminal repeat (LTR) | GGTCTCTCTGGTTAGACCAGATCTGAGCCTGGGAGCTCTCT<br>GGCTAACTAGGGAACCCACTGCTTAAGCCTCAATAAAGCT<br>TGCCTTGAGTGCTTCAAGTAGTGTGTGCCCGTCTGTTGTGT<br>GACTCTGGTAACTAGAGATCCCTCAGACCCTTTTAGTCAGT<br>GTGGAAAATCTCTAGCA |
| 76 | Psi Packaging signal | TACGCCAAAAATTTTGACTAGCGGAGGCTAGAAGGAGAG<br>AG |
| 77 | Rev response element (RRE) | AGGAGCTTTGTTCCTTGGGTTCTTGGGAGCAGCAGGAAGC<br>ACTATGGGCGCAGCCTCAATGACGCTGACGGTACAGGCCA<br>GACAATTATTGTCTGGTATAGTGCAGCAGCAGAACAATTT<br>GCTGAGGGCTATTGAGGCGCAACAGCATCTGTTGCAACTC<br>ACAGTCTGGGGCATCAAGCAGCTCCAGGCAAGAATCCTGG<br>CTGTGGAAAGATACCTAAAGGATCAACAGCTCC |
| 78 | Central polypurine tract (cPPT) | TTTTAAAAGAAAAGGGGGGATTGGGGGGTACAGTGCAGG<br>GGAAAGAATAGTAGACATAATAGCAACAGACATACAAAC<br>TAAAGAATTACAAAAACAAATTACAAAATTCAAAATTTTA |
| 79 | Long WPRE sequence | AATCAACCTCTGATTACAAAATTTGTGAAAGATTGACTGG<br>TATTCTTAACTATGTTGCTCCTTTTACGCTATGTGGATACG<br>CTGCTTTAATGCCTTTGTATCATGCTATTGCTTCCCGTATG<br>GCTTTCATTTTCTCCTCCTTGTATAAATCCTGGTTGCTGTCT<br>CTTTATGAGGAGTTGTGGCCCGTTGTCAGGCAACGTGGCG |

| SEQ ID NO: | Description | Sequence |
|---|---|---|
| | | TGGTGTGCACTGTGTTTGCTGACGCAACCCCCACTGGTTGG
GGCATTGCCACCACCTGTCAGCTCCTTTCCGGGACTTTCGC
TTTCCCCCTCCCTATTGCCACGGCGGAACTCATCGCCGCCT
GCCTTGCCCGCTGCTGGACAGGGGCTCGGCTGTTGGGCAC
TGACAATTCCGTGGTGTTGTCGGGGAAATCATCGTCCTTTC
CTTGGCTGCTCGCCTGTGTTGCCACCTGGATTCTGCGCGGG
ACGTCCTTCTGCTACGTCCCTTCGGCCCTCAATCCAGCGGA
CCTTCCTTCCCGCGGCCTGCTGCCGGCTCTGCGGCCTCTTC
CGCGTCTTCGCCTTCGCCCTCAGACGAGTCGGATCTCCCTT
TGGGCCGCCTCCCCGCCT |
| 80 | 3' delta LTR | TGGAAGGGCTAATTCACTCCCAACGAAGATAAGATCTGCT
TTTTGCTTGTACTGGGTCTCTCTGGTTAGACCAGATCTGAG
CCTGGGAGCTCTCTGGCTAACTAGGGAACCCACTGCTTAA
GCCTCAATAAAGCTTGCCTTGAGTGCTTCAAGTAGTGTGT
GCCCGTCTGTTGTGTGACTCTGGTAACTAGAGATCCCTCAG
ACCCTTTTAGTCAGTGTGGAAAATCTCTAGCAGTAGTAGTT
CATGTCA |
| 81 | Envelope;
MLV 10A1 | ATGGAAGGTCCAGCGTTCTCAAAACCCCTTAAAGATAAGA
TTAACCCGTGGAAGTCCTTAATGGTCATGGGGGTCTATTTA
AGAGTAGGGATGGCAGAGAGCCCCCATCAGGTCTTTAATG
TAACCTGGAGAGTCACCAACCTGATGACTGGGCGTACCGC
CAATGCCACCTCCCTTTTAGGAACTGTACAAGATGCCTTCC
CAAGATTATATTTTGATCTATGTGATCTGGTCGGAGAAGA
GTGGGACCCTTCAGACCAGGAACCATATGTCGGGTATGGC
TGCAAATACCCCGGAGGGAGAAAGCGGACCCGGACTTTTG
ACTTTTACGTGTGCCCTGGGCATACCGTAAAATCGGGGTG
TGGGGGCCAAGAGAGGGCTACTGTGGTGAATGGGGTTGT
GAAACCACCGGACAGGCTTACTGGAAGCCCACATCATCAT
GGGACCTAATCTCCCTTAAGCGCGGTAACACCCCCTGGGA
CACGGGATGCTCCAAAATGGCTTGTGGCCCCTGCTACGAC
CTCTCCAAAGTATCCAATTCCTTCCAAGGGGCTACTCGAG
GGGGCAGATGCAACCCTCTAGTCCTAGAATTCACTGATGC
AGGAAAAAAGGCTAATTGGGACGGGCCCAAATCGTGGGG
ACTGAGACTGTACCGGACAGGAACAGATCCTATTACCATG
TTCTCCCTGACCCGCCAGGTCCTCAATATAGGGCCCCGCAT
CCCCATTGGGCCTAATCCCGTGATCACTGGTCAACTACCCC
CCTCCCGACCCGTGCAGATCAGGCTCCCCAGGCCTCCTCA
GCCTCCTCCTACAGGCGCAGCCTCTATAGTCCCTGAGACT
GCCCCACCTTCTCAACAACCTGGGACGGGAGACAGGCTGC
TAAACCTGGTAGAAGGAGCCTATCAGGCGCTTAACCTCAC
CAATCCCGACAAGACCCAAGAATGTTGGCTGTGCTTAGTG
TCGGGACCTCCTTATTACGAAGGAGTAGCGGTCGTGGGCA
CTTATACCAATCATTCTACCGCCCCGGCCAGCTGTACGCC
ACTTCCCAACATAAGCTTACCCTATCTGAAGTGACAGGAC
AGGGCCTATGCATGGGAGCACTACCTAAAACTCACCAGGC
CTTATGTAACACCACCCAAAGTGCCGGCTCAGGATCCTAC
TACCTTGCAGCACCCGCTGGAACAATGTGGGCTTGTAGCA
CTGGATTGACTCCCTGCTTGTCCACCACGATGCTCAATCTA
ACCACAGACTATTGTGTATTAGTTGAGCTCTGGCCCAGAA
TAATTTACCACTCCCCCGATTATATGTATGGTCAGCTTGAA
CAGCGTACCAAATATAAGAGGGAGCCAGTATCGTTGACCC
TGGCCCTTCTGCTAGGAGGATTAACCATGGGAGGGATTGC
AGCTGGAATAGGGACGGGGACCACTGCCCTAATCAAAAC
CCAGCAGTTTGAGCAGCTTCACGCCGCTATCCAGACAGAC
CTCAACGAAGTCGAAAAATCAATTACCAACCTAGAAAAGT
CACTGACCTCGTTGTCTGAAGTAGTCCTACAGAACCGAAG
AGGCCTAGATTTGCTCTTCCTAAAAGAGGGAGGTCTCTGC
GCAGCCCTAAAAGAAGAATGTTGTTTTTATGCAGACCACA
CGGGACTAGTGAGAGACAGCATGGCCAAACTAAGGGAAA
GGCTTAATCAGAGACAAAAACTATTTGAGTCAGGCCAAGG
TTGGTTCGAAGGGCAGTTTAATAGATCCCCCTGGTTTACCA
CCTTAATCTCCACCATCATGGGACCTCTAATAGTACTCTTA
CTGATCTTACTCTTTGGACCCTGCATTCTCAATCGATTGGT
CCAATTTGTTAAAGACAGGATCTCAGTGGTCCAGGCCTG
GTTTTGACTCAACAATATCACCAGCTAAAACCTATAGAGT
ACGAGCCATGA |
| 82 | miR155 CD47
target sequence
1 | CCTGGAGGCTTGCTGAAGGCTGTATGCTGTTATCCATCTTC
AAAGAGGCAGTTTTGGCCACTGACTGACTGCCTCTTAAGA
TGGATAACAGGACACAAGGCCTGTTACTAGCACTCA |
| 83 | miR21 cMyc
sequence | CATCTCCATGGCTGTACCACCTTGTCGGGTGTTCGCCTCTT
GACATTCTCCTGTTGAATCTCATGGAGAATGTCAAGGGCG
AACACTGACATTTGGTATCTTTCATCTGACCA |

While certain of the preferred embodiments of the present invention have been described and specifically exemplified above, it is not intended that the invention be limited to such embodiments. Various modifications may be made thereto without departing from the scope and spirit of the present invention.

What is claimed is:

1. A viral vector comprising a therapeutic cargo portion, wherein the therapeutic cargo portion comprises: a small RNA sequence that is capable of binding to a pre-determined complementary mRNA sequence, wherein the pre-determined complementary mRNA sequence comprises an FDPS sequence,
    wherein the small RNA sequence comprises a sequence having at least about 80%, or at least about 85%, or at least about 90%, or at least about 95% identity with SEQ ID NO: 1, SEQ ID NO: 2, SEQ ID NO: 3, or SEQ ID NO: 4.

2. The viral vector of claim 1, wherein the small RNA comprises SEQ ID NO: 1, SEQ ID NO: 2, SEQ ID NO: 3, or SEQ ID NO: 4.

3. A lentiviral particle capable of infecting a target cell, the lentiviral particle comprising:
    an envelope protein optimized for infecting the target cell; and
    the viral vector of claim 1.

4. A composition comprising:
    the lentiviral particle according to claim 3; and
    optionally comprising an aminobisphosphonate drug.

5. A method of treating cancer in a subject using an immunotherapy-based composition, the method comprising:
    administering to the subject a therapeutically effective amount of a lentiviral particle comprising the viral vector of claim 1.

6. The method of claim 5, further comprising administering to the subject an effective amount of an aminobisphosphonate drug.

7. The method of claim 6, wherein the aminobisphosphonate drug comprises zoledronic acid.

8. A viral vector comprising a therapeutic cargo portion, wherein the therapeutic cargo portion comprises:
    a first small RNA sequence that is capable of binding to a first pre-determined complementary mRNA sequence, wherein the first pre-determined complementary mRNA sequence comprises an FDPS mRNA sequence; and
    a second small RNA sequence that is capable of binding to a second pre-determined complementary mRNA sequence, wherein the second pre-determined complementary mRNA sequence comprises a CD47 mRNA sequence or a cMyc mRNA sequence,
    wherein a second small RNA sequence comprising CD47 comprises a sequence having at least about 80%, or at least about 85%, or at least about 90%, or at least about 95% identity with SEQ ID NO: 5, SEQ ID NO: 6, SEQ ID NO: 7, SEQ ID NO: 8, or SEQ ID NO: 9 and,
    wherein a second small RNA sequence comprising cMyc comprises a sequence having at least about 80%, or at least about 85%, or at least about 90%, or at least about 95% identity with SEQ ID NO: 10, SEQ ID NO: 11, SEQ ID NO: 12, SEQ ID NO: 13, or SEQ ID NO: 14.

9. The viral vector of claim 8, wherein the first small RNA sequence is under the control of a first promoter, and the second small RNA sequence is under the control of a second promoter.

10. The viral vector of claim 8, wherein the first small RNA sequence and the second small RNA sequence are under the control of a single promoter.

11. The viral vector of claim 8, wherein the second small RNA sequence comprising CD47 comprises SEQ ID NO: 5, SEQ ID NO: 6, SEQ ID NO: 7, SEQ ID NO: 8, or SEQ ID NO: 9, wherein the second small RNA sequence comprising cMyc comprises SEQ ID NO: 10, SEQ ID NO: 11, SEQ ID NO: 12, SEQ ID NO: 13, or SEQ ID NO: 14.

12. A method of treating cancer in a subject using an immunotherapy-based composition, the method comprising:

administering to the subject a therapeutically effective amount of a lentiviral particle comprising the viral vector of claim 8.

13. The method of claim 12, further comprising administering to the subject an effective amount of an aminobisphosphonate drug.

14. The method of claim 13, wherein the aminobisphosphonate drug comprises zoledronic acid.

15. A viral vector comprising a therapeutic cargo portion, wherein the therapeutic cargo portion comprises:
- a first small RNA sequence that is capable of binding to a first pre-determined complementary mRNA sequence, wherein the first pre-determined complementary mRNA sequence comprises a CD47 mRNA sequence; and
- a second small RNA sequence that is capable of binding to a second pre-determined complementary mRNA sequence, wherein the second pre-determined complementary mRNA sequence comprises a cMyc mRNA sequence,
- wherein the second small RNA sequence comprises a sequence having at least about 80%, or at least about 85%, or at least about 90%, or at least about 95% identity with SEQ ID NO: 10, SEQ ID NO: 11, SEQ ID NO: 12, SEQ ID NO: 13, or SEQ ID NO: 14.

16. The viral vector of claim 15, wherein the first small RNA sequence is under the control of a first promoter, and the second small RNA sequence is under the control of a second promoter.

17. The viral vector of claim 15, wherein the first small RNA sequence and the second small RNA sequence are under the control of a single promoter.

18. A method of treating cancer in a subject using an immunotherapy-based composition, the method comprising:
- administering to the subject a therapeutically effective amount of a lentiviral particle comprising the viral vector of claim 15; and
- administering to the subject a therapeutically effective amount of an aminobisphosphonate drug.

19. The method of claim 18, wherein the aminobisphosphonate drug comprises zoledronic acid.

* * * * *